United States Patent
Metcalf et al.

(10) Patent No.: US 8,372,601 B2
(45) Date of Patent: Feb. 12, 2013

(54) COMPOSITIONS AND METHODS FOR THE SYNTHESIS OF APPA-CONTAINING PEPTIDES

(75) Inventors: William W. Metcalf, Savoy, IL (US); Wilfred A. van der Donk, Champaign, IL (US); Junkal Zhang, Urbana, IL (US); Benjamin T. Circello, Maineville, OH (US); Svetlana A. Borisova, Champaign, IL (US)

(73) Assignee: University of Illinois at Urbana-Champaign, Urbana, IL (US)

(*) Notice: Subject to any disclaimer, the term of this patent is extended or adjusted under 35 U.S.C. 154(b) by 0 days.

(21) Appl. No.: 13/011,075

(22) Filed: Jan. 21, 2011

(65) Prior Publication Data

US 2011/0217734 A1    Sep. 8, 2011

Related U.S. Application Data

(60) Provisional application No. 61/296,993, filed on Jan. 21, 2010.

(51) Int. Cl.
    C12P 1/00      (2006.01)
    C12P 13/00     (2006.01)
    C12P 13/02     (2006.01)
    C12P 7/00      (2006.01)
    C12P 7/40      (2006.01)
    C12P 7/54      (2006.01)
    C12N 9/00      (2006.01)
    C12N 1/00      (2006.01)
    C12N 1/22      (2006.01)
    C12N 1/20      (2006.01)
    C12N 15/00     (2006.01)

(52) U.S. Cl. .......... 435/41; 435/128; 435/129; 435/132; 435/136; 435/183; 435/243; 435/252.2; 435/252.3; 435/252.5; 435/320.1

(58) Field of Classification Search .................. None
See application file for complete search history.

(56) References Cited

U.S. PATENT DOCUMENTS

2010/0064393 A1*  3/2010  Berka et al. ................... 800/298

* cited by examiner

*Primary Examiner* — Celine Qian
*Assistant Examiner* — Addison D Ault
(74) *Attorney, Agent, or Firm* — Ice Miller LLP

(57) ABSTRACT

The disclosure of the present application provides polypeptide sequences and nucleotide sequences coding for the polypeptide sequences of proteins used in the production of APPA-containing peptides. In at least one embodiment of the present disclosure, an isolated nucleic acid is disclosed which comprises a nucleotide sequence encoding a polypeptide having a sequence identity of 60 percent or greater to an amino acid sequence selected from the group consisting of SEQ ID NOS: 2-13, and 15-23.

19 Claims, 15 Drawing Sheets

SEQUENCE LISTING

```
<160> NUMBER OF SEQ ID NOS: 25

<210> SEQ ID NO 1
<211> LENGTH: 35265
<212> TYPE: DNA
<213> ORGANISM: Bacillus subtilis

<400> SEQUENCE: 1
gaagtttgag aatgtctcta ttaagactgt agggctgagc agctcgcaaa acattgaatt      60
tctagatcct gaatcgcaag cgatagacgt gacggctaaa ggctctcccg ccaatataaa     120
aaaactgaag aaatcagata ttgaattgta tgtgaatgtt tcagatttag atgacgggga     180
gcatagcgtg aagcttgaag taaacgggcc tcagaatgta acctggtcct tggggcagaa     240
aagcgccaaa atcaagctga cgtctaaaaa aagcaataca tcaactaatg acaacagcag     300
caatacatca gggaaccagg atgacacaga taagcaaacg aataatcaaa agaacaacca     360
gcaagaagat acaacgaaca ctgataaaga cagcaatgat caaaaacaag acgaaaataa     420
agatcaaaac caagatcagg atgaggacga atccactgcg gattcacaat ccacatcaga     480
```

```
ataaaaaagg agcgattata aaatgggcaa gtattttgga acagacggtg taagaggtgt      540
cgccaatagt gagcttacac ctgagctggc cttcaaagtc ggacgtttcg gcggatatgt      600
gctgacaaaa gacaaacaac gtccgaaagt gctgataggc cgcgatacac gcatctccgg      660
ccatatgctg gagggagccc ttgtcgccgg acttttatcc attggcgcag aagtcatgcg      720
cctgggtgtc atttctacac ctggtgtatc ttatttaaca aaagcgatgg atgcagaggc      780
aggcgtcatg atttctgctt ctcacaaccc agtgcaggat aacggcatca gttttttcgg      840
gggagacgga tttaagcttt ctgacgaaca ggaggctgaa attgagcgcc tgatggacga      900
accggaagat aggctgccaa ggccggtcgg agccgatctc ggtcttgtaa acgactattt      960
tgaaggtgga caaaaatatc tgcagttctt aaaacagact gctgatgaag atttcacagg     1020
cattcatgtg gcactggact cgcacatggt gcaacgtcg tccttggcga cacacctgtt     1080
tgctgattta gatgccgatg tttcaacaat ggggacttcc ccgaacggat aaacattaa     1140 tgacggcgtc ggatcgactc atcctgaagc gctcagcgcg tttgtcaaag agaaaaacgc     1200
cgatctcggt cttgcgtttg acggtgatgg cgaccgcctg attgctgtcg atgaaaaagg     1260
aaatatcgtt gacggcgacc aaatcatgta catatgctca aaacacctga atcagagggg     1320
ccgtttaaag gatgatacag tggtttcgac tgtaatgagc aaccttggct tctataaggc     1380
gcttgaaaaa gaaggcatca aaagcgtgca acggctgtc ggtgaccgtt acgtagtaga     1440
agcgatgaaa aaagacggct acaatgtcgg cggtgagcag tcaggacatc ttatttttcct     1500 tgattacaac acgacagggg acggattatt gtctgctatt atgctgatga acacattgaa     1560
agcgacaggc aagccgttgt cagagcttgc agctgaaatg cagaagttcc cgcagctgtt     1620
agtcaatgtg agagtaactg ataaatataa agtcgaagag aacgaaaag taaaagctgt     1680 tatttctgaa gttgaaaaag aaatgaacgg cgacggccgg attttggtcc gcccttcagg     1740
cactgaacca ctagtccgtg ttatggctga agcgaagacg aaagaactgt gcgatgagta     1800
tgtcaatcgc attgttgaag tcgtccggtc agaaatggga ttagagtaac gaagcctatt     1860
atcagagagt gaacaagaca agcgagtttt acatatgata attgtgagac atacggcaaa     1920 gttgttaaa aaacaattga ccgtttatgc cacatgctgt aaaatcaagc ttgtcttgtt     1980 cttatttct ctacaggaaa gaagacggga ttattgtttc acctataatt atagcgcccg     2040
aactaagcgc ccgaaaaaag gcttagttga cgaggatgga ggttatcgaa ttttcggcgg     2100 atgcctccg gctgattatg cagatcacag ccgtaaggat ttcttcaaac caaggggta     2160 actccttgaa caaagagaaa tcacatgatc ttccaaaaac atgtaggagg ggacgattga     2220 aagtccccctt gaaatttgac tttcttcgtc tccttttaca atcttaggag gaagaaaaat     2280
atgtgtggaa tcgtaggtta tatcggtcag cttgatgcga aggaaatttt actgaaaggg     2340
ttagaaaagc ttgagtaccg cggatatgat tctgctggta tcgctgttgc caacgaacag     2400
ggaatccatg tgttcaaaga aaaggacgc attgcggatc ttcgtgaagt tgtggatgcc     2460
aatatagaag cgaaagctgg aattggccat acgcgctggg caacacacgg cgaaccaagc     2520
tatctaaacg ctcacccgca tcaaagcgca ctgggccgtt ttacacttgt tcataacggc     2580
gtgatcgaga actatgttca gctgaaacaa gagtatttac aagatgtaga gctcaaaagt     2640
gacaccgata cagaggtagt cgttcaagta atcgagcaat tgtcaacgg aggtcttgat     2700 acagaagaag cgttccgcaa aacacttaca ctgttaaaag ctcttatgc aattgcttta     2760 ttcgacaaca aaaacagaga aacgattttt gtagcgaaaa acaaaagccc tctattagtc     2820
ggtcttggag atacattcaa tgtcgtagca tctgatgcga tggcaatgct tcaagtaacc     2880
```

```
aatgaatacg tagagctgat ggataaagaa atggtcatcg tcactgatga tcaagttgtc    2940
atcaaaaacc ttgatggtga cgtgatttca cgtgcttctt atattgctga gctggatgcc    3000
agcgatatcg aaaaggtac gtaccctcac tacatgttga agaaacgga tgagcagcct     3060 gttgtcatgc gcaaaatcat ccaaacgtat caagatgaaa acggcaaact gtctgtgcct    3120
ggcgatatcg ctgccgctgt agcggaagcg gaccgcatct atatcattgg ctgcggaaca    3180
agctaccatg caggacttgt cggtaaacaa tatattgaaa tgtgggcaaa cgtgccggtt    3240
gaagtgcatg tagcgagtga attctcttac aacatgccgc ttctgtctaa gaaaccgctc    3300 tttatttttcc tttcacaaag cggagaaaca gcagacagcc gtgcagttct tgttcaagtc    3360
aaagcacttg gacacaaagc actgacaatc acaaacgtac cgggatcaac gctttctcgt    3420
gaagctgact acacgttgct gcttcatgca ggccctgaaa ttgctgttgc ttcaacgaaa    3480
gcatacactg cacaaatcgc tgttcttgct gttcttgcat ctgtagctgc tgacaaaaac    3540
ggcattgata tcggatttga cctcgtcaaa gaactcggta tcgctgcgaa cgcaatggaa    3600 gcccttttgcg accagaaaga cgaaatggaa atgatcgccc gtgaatacct gactgtatcc    3660
agaaacgctt tcttcattgg ccgcggcctt gactacttcg tatgtgtcga aggcgcactg    3720
aagctgaaag agatttctta cattcaggca gaaggctttg ccggcggaga actgaagcac    3780
ggcaccattg ccttgatcga acaaggtaca ccagtatttg cactggcaac acaagagcac    3840
gtaaacctaa gcatccgcgg aaacgttaaa gaagttgccg ctcgcggagc aaacacatgc    3900
atcatctcac tgaaaggcct agacgatgcg gatgacagat tcgtactacc ggaagtaaac    3960
ccagcgcttg ctccgttggt atctgttgtt ccattgcagc tgatcgctta ctatgctgca    4020
ctgcatcgcg gctgtgatgt tgataaaccg cgtaaccttg cgaagagtgt tactgtggag    4080
taaaaatgtt aaccccttt ggttatttag ccaagggggt ttttatgtta gaggtgattt     4140
tgtatgaaag aaatccaaga ggaattttat aattattttc gcacattctg tttagtaaat    4200
aactgagtgg gtaaaaattt aaattgccaa ctataattaa atactggttc aaagaaatta    4260
gtatgataga tttcacatgc cttagtaaag attatatctt caaagggaaa aaggattgat    4320
acttcattct tcgatttcca acatgtaagt ttgaatttac tgaatagaat atgaggtttt    4380
tgttgacaac tttaaaatt tagcttatct tatacgtaac ttcataatct gcaaatgtta     4440
tttttccttt taaaataact aggcctttag cattcttta atatttaatt ttaaatcttg     4500
aaaggatgaa aaagcattct aataaaagga agagtaacat aagtcgattt attttataaa    4560
tcaaggttct aaattaacga tgatttcatt cctttagaag gaacttaaaa taatgtatat    4620
agtaaaataa ccaataataa ggtagctctt caaaaaactt cgcagaagtt agttgaagtg    4680
aaaccgacaa ttttcaagat tcaatgatct tacatcatca ttgaaatttt gaagttgtcg    4740 gttttttttgt tggaaaaaaa tagagataaa taaaaattga aataaataat agaaaaatat    4800
gatctgattg agaggtcatt tgagcaataa cgagatttaa aaaagggaga agttagaatg    4860
ttagtttcgc tgagtttgtc atcattatta acattatttt ttatgacgct tattgcttct    4920
gggataagcg gactattgtt tttacatcca cgcgtgccct tgggttatat ccgcattcat    4980
attggtatct tggctttacc gcctttggtt tccttagtga atcttgccaa taagagtgtg    5040
gaaggaaatg ttggcccttg gtacttcgat tccttagctt ggttaatgac tttctttgtt    5100
ttgacaattg gtctaatcat tcagcgtttt tctgtacgtt acttaatggg tgatcgatct    5160
tatcgaaaat attttacgct ttttactttc actacaggtg ctgcttcaat tgcatggtta    5220
agtggcgatc tccgcttgat ggttatattt tggggagcaa ctcttgtcgg tttaacctta    5280
```

```
ctgataaggt taaacagtgc ttggcaagtg gctagtgaag cagccaaggt ttctggtcga    5340
ttatttttgt taagttggtt ttcattgttt ttcgcgatga tttggctgtt tcaagtcaca    5400
ggtcaatggc agttatcatt ggtgctaaca aatgaaagtt tagctcaact gggaggatgg    5460
gagagaacag ggattaatct attgattgta ttagcagtga tcattcctgc agctcaatgg    5520
ccattccaaa gatggttaat tgagtctatt gttgctccaa ctcctgtttc tgcgattatg    5580
cacgcaggtt tagtaaatgc aggcgggatt atactagctc gattttcacc tctatttaat    5640
ggaggtatag cttcgattat tttacttatg cttgctagca tctctgtatt gattggaact    5700
ggtattagtt tagtccaggt tgactataaa cgccagttag taggctccac gattggacaa    5760
atggggttta tgctcattca atgtgcatta ggagcctata tcgcagccat tattcatctt    5820
attttacatg gtttattcaa agctacgttg tttttacaag ctggttcagc agtacggcgt    5880
catgaaggat cagctcgcgc taatgaagga acatcctatt tatggatcat ggctggtcgg    5940
attttatcct tagttatagg cgttgctttt tggctcgttg ctcctggaga ggggtatcaa    6000
ttcattagtg cgctaatctt agggtggtca ttgtccgttt cttggactca gctcgtagct    6060
tttggtgagg gaagaattgg tcgaattgct ggtttaacat tttaggagg aggagccttt     6120 gtatatttta tcattcataa cctcttctat aagtggttgc atacaagcgt ttttcaaagt    6180
gttcaacctc caatgtcagc tgtcatcatt gtcgtatgtc tcttactatt tggtagtgct    6240
ttaggtacgt gggttgctcg tcatcgttct tcagttttgt tcgcagtact ctatctttgg    6300
ttagtacgat taggtgaagc aaaaccaaag acagtagaga gtcatccaga ctaccttaaa    6360 caattttat cataaggagg taataagtgt tgggcattac atccgtatta acaaaagaaa     6420
atgtaaaaaa gaaagataca gagattgatt ttcaagatag agatattaac gttttaattg    6480
aatcagccag ccgagtcatt gcgccacttt ggcctatttc aacatttgct gcacgtagcc    6540
cgtggatggg acttgaaaac caaccttttg atcaggttgc aagttggttg aaacaaactc    6600
gtgatgttga tatataccct agtgcctcta tgatccgttc agcaaagaat aaaggtgaga    6660
ttgacgaaga ttttgtaaag atggggctac agcgttggct tgactcacat tcctttaata    6720
tcccgcggga cgtggcagaa cgattttgtc atgctggatt acaattagat ccactgcctt    6780
ccagcctttt atcatcacat aagctggaga aattggtgaa tgaatttagt ggattggatc    6840
atatcgagaa ttttttttatg caaccaataa gttcatatat agagaatcaa gacggagaaa   6900
agttagttaa tatacttgat catcatgtta tcaagtggtg taagttatat ctggatgact    6960
ctcaagcagg ttggacaatg cctaatcgtg aggaaggttt ctatcgtgcc tggcagcaac    7020
tcattcaata tgatccagca cttagtaaaa agcagcgtga aggttaaaaa ggctggccgc    7080
aagaggcaca tatggcttta caagaagcct tattcgcact agaaatccca gaatcggaaa    7140
tccagactta tcttgaaggt catttacttt ccttacctgg atgggcaggg atgatgcttt    7200
ggcgctccca acaatcgagc catgaacatg cactccttac agaatattta gcggttcgaa    7260
tatccatgga gtgggccctt ataaagccat atttaccttt gaatactcaa cgatctggga    7320
aagaaatttc gattactccc cttttagcag cctggattca ttgggggagc cttacattag    7380
aggaatggtc acagatgccg gccaatgaac aaaacgaata tttatcattt gcctatagct    7440
ttgatgagaa acttcgcagg aaactttggc tagaagcatg gaacaaaaca catacagatc    7500
gattaagtca aaagatcatc tcgaaacaac gtgaaaccga cggtaaaaaa tctgcaatag    7560
ctcaattggc attctgtatc gatgtacgat cagaaccttt tcgtcgtcaa ctcgaaaaag    7620
caggcccgtt tgaaacgatt ggtgttgctg gtttcttcgg ggtgccgatt gcaacttgtg    7680
```

```
aacttggcag taaacacagt catgcctcct tgccggtcat acaaaaaccg caaaataaaa    7740
taaaagagtt cgtagatgaa gatgtactcg aaaaatacaa ccaacgcaag caagcagttc    7800
attccgtaag ccatacattt aaaacgatga aacagaatgt acttacgagc ttacttctac    7860
ctgagttaag tggaccttgg cttagtctgc aaatggtagc gcgtagtttt gtaccaagaa    7920
aagcggatcg tttcattcgt catctccgtg agacttggtt acgtaaacct gatacaaaac    7980
tctcgcttca tcatgatgat gacacagagg cagaaatacc tgtaggtttt actgaagaag    8040
aaaaagtgaa ctatgctcgg caagcactaa aaatgatggg attaacagag aatttcgcac    8100
cgttagtcgt gatttgcggg catggcagtc aaagtaccaa taatccttat accgcggctc    8160
ttgattgtgg tgcctgcggt ggggcggccg gtggattcaa tgcaagagtt ttagctgctt    8220
tatgtaatct ttcagaggta agagaggttc ttttaactga aggaatgaaa atccctgagg    8280
atacggtttt tgccgccgct gaacatcata caacggtgga tgaattgcat tggatttatg    8340
taccagaact ttctgaagcc gctcaagaag catttgaacg aatcgaagct gttatgccga    8400
aagtgagtca taatgcaaat gcagaacgtc tagcccaatt accgaatttc caatcgaaac    8460
ttaaaaatcc gaaggcagag gcacaccgat tgcgggaga tggagtgag atacgtccgg     8520
aatggggatt ggctcgtaat gccgctttta ttatcggcca acgtgaacta actaaggatt    8580
gtgatttgga aggaagagcc tttcttcata attatgattg gaagcaggat gaaagcggtg    8640
aactcctagc aaatattatt gctgggcctg gaactgtggc tcaatggatt aatttacaat    8700
attacgcatc aacggtagca cctcattatt atggtagcgg aagtaaagca actcaaaccg    8760
ttactgcagg tctcggagtt atgcagggga atgcaagtga cttgttagcc ggactgcctt    8820
ggcaatccgt catgcaatca gatcatgagg cttatcattc tcctcttcgt ttgttgatcg    8880
tcatccaagc acctaaagaa tatgtagaac gattattaaa taatgattca gcatttctag    8940
aaaaagttca aaatgatgg gttcgactgg ctagtgttga tccagaaggg cattgggaaa    9000
actggtaact gctaaaataa tcatctcaaa tggatttgtt actcaatcaa aaaatgaaca    9060
cataagaaga ggtgggctat atgaatgtag ataaaaataa aaaagtatta tttttgacgg    9120
acattgaaaa cggattggag cctatttac aagaagtgac tcatactcca gcagaaaata    9180
tgttgacgat acaaagctat ggtgccgata tctcacatcc ttatggagaa atcatgaggt    9240
ctgttattat tgcaatttat caggaagatg ttgaggaggt ttttgttgta ggaacaaaag    9300
ataagaggac ttccacaggt catatactaa ctcaacttga aacaatgaaa gataaactac    9360
aaacattgga ttatcttttt caaaattgca ggcctgaatt ttcaggtggt acattcgatg    9420
aatggctaaa tggaaatgaa aatagcagtg acgctattga aaaaagtgtt gatatcattc    9480
gccatcaccc tttagtgccg tcatatgtta aagttcgagg tttactcgtt catcataagg    9540
gtggaaaatc ctcaattgag gaggttccta ctgttaaaac agcgtcaagc cttacttgat    9600
cattgcttgt catgatgaag tggaagggt caccttctgt gcccccatat atggaaaaaa    9660
gcagttctaa ggagaatgta tggactctaa tttaactgat tttgtaatga agcaataga    9720
ggaaataaat ccgtttgatc gtgaaagtat agaatgtatg aaaaagtaa ttagaaaagc    9780
aattgatttt tatcatttaa aaacgtatga agaagttgag gaaacccatg taggaagcgt    9840
tcgatttttg catgtacact ccattatgga agaaaatatg ttatccaaaa ttgtagtggt    9900
cataagaaac ggtgaaactg atttggatat tgaaggtgta tatgaaggac atgttgtaag    9960
agaatattaa tgagacgaaa taacaataga agatgccaat ttttttgcca ggagatgttt   10020
tatatatgaa aaaatcgaaa ggttcttttg aatcagagat cagtaagtcc attactcaat   10080
```

```
gggagaagga ttatctaggg cgtgggtctg tatctgttaa gactgatata ctgcgggata   10140
tgatcatcgt taatttaaaa ggaatttaa caccagctga atatgcagtt tgtggatcaa    10200
aagagggtat gttatctatc aaacaaactc gttcggagtt agttgaatca ggtatagaag   10260
gtcttaagga tattatccta acaataactg gagaagaagt gaaaagtttc cacactgatt   10320
taagctctcg gacaggtgaa cgagtgatgg tatttaaatt atttaatgat ctagagaaaa   10380
atttagaaaa gatcttataa tataaaaaat tgaaatgttt atgaacacta ctattcaagc   10440
ctagtataga actggttatt caaatgttat tatattttc cttgttaaac aggatggcag     10500
ttattataaa ttgaacataa ttaacgccgc ttcttttgtt ttacagttat ggcatcattg   10560
atgatttata attcacaacc taagcggacg tgaagagata tcaaagatcc tataagttga   10620
gatgaatttg atgaataaga cctctttggt taaatgacca aagggtgtctt ttgtgtcagt  10680 gctcaacata ttcgataata acaattaata gggtggctga gtttggcatc tcacaggatt   10740
atttacagtt aggataagga gaattaaaag ggtgaaagct gaacaaataa tgaaagaatg   10800
gccaattcat ttaccctggt tgaatcaatc acagaacgat ttgacattcc tgtaagtatg   10860
tagataaacg gttgaatatt atcaaacgat ccttcctata agcaggaagg ttttttaatg   10920
ataaaatatt cgctattagt aggtgaattc atcaaatgtt ccgccatgct cccaatgtac   10980 accttccgt aagggcaaag tcaaatgtca aaataaaatc tttcctaagt taatcagaaa    11040
tttattttca tatcgtatcc tttccgtatc acgtgaaagg agcatcatat gaaaacatta   11100
tggaaagtcc taaagtctt ttttggcagc ttggctgctt tggttttcct tgtatccgtc     11160
tcggtattta tgtatcacca ttaccaacta aataaggagg cggcactatt aaaaggcaaa   11220
ggcactctag tcgatgttga tggtaaaaag atgaatgtgt atgaagaggg aagcgggaag   11280
gatacgtttg tgtttatgtc cggttcgggg atcgctgcgc ctgtttatga gatgaaaggg   11340
gtgtaccgca agttttcaaa agaaaacaag attgctgtcg ttgatcgggc tggttatgga   11400
tacagtgatg tgtctcacga tgacagagat attgatacgg tactggaaca gacgaggaaa   11460
gcgcttatga aaagcggaaa taagcctcct tatattttaa tgcctcattc catatccggg   11520
attgaagcca tttattgggc gcagaaatat cctaaggaaa tcaaggccat tattgcgatg   11580
gacattggat tgccccagca gtatgtcacg tataaattga gcaggatcga caggcttaaa   11640
gtgagagggt tccacctgtt aacttcgatt ggtgttcatc ggtttatgcc ttccgctgta   11700
tataatcctg aggtgattcg gcagtcgttt ttaactgatg aagaaaaaga atctataaa    11760 gccattaact ttaagcaatt ttttaatgca gatatggagc atgagctttt acagtcttac   11820
caaaatggca gcaaatctgt gaatctgccg gcgccaaaag aaactcccgt cttgattta    11880 gatgcggtct ctgaccaaaa tagacattca agtatgcca tacaaaaccg aaaagattat     11940
gaagcgtttg cggctcaatt caatacagcc gaaataaagg aactaagggg aacacacagt   12000
atttatttat atcagcctga tcaaatatat aaactttcta tggagtttat gagaaaggtt   12060
cgctaggatg aagggttatc atatttaat cgtggaagat gatgtgacga ttggtgatct    12120
actgcaaaag attttgcagc gtgagggata tcatgtgatg tggaaaacag atggagcgga   12180
tgtgcttacg gtgattcaga aggtggattt ggtcattatg gatgtgatgc tgccgggtga   12240
agacggatat caaatgtctg ctaaaatcaa aaaactgggg ctgcgcattc cggtcatttt   12300
tctctcggcc cgcaatgata tggacagcaa gctccaaggt ttgcagatcg gtgaggatta   12360
tatggtaaag cctttgacc ctcgagagct gctattaaga atgcagaata tgcttgagca    12420
tcattatggc acttttacgc aaatcaaaca tttgtatatt gatgcggaaa ccaaaaagt    12480
```

```
attcaatgaa agcctgcatg atgaggtgtt gtttactgcg attgagcgga aaattttctt    12540
ttatttatat gacaatagag acagcaccct gacaaaggaa catttctttg aatatttgtg    12600
gcagctcgaa gacagaaacc cgaatatcgt taatgtgcac attaaaaaaa tcagagccaa    12660
aatcaaggat caagcgggtg aaattattga aaatatctat ggagaagggt atcgattgaa    12720
taccgttgta aagaaatgaa gctcaagaca aaatatcagt tgttattatg tacggccgtc    12780
gttagtgttc cggtgctatt gctggcggtt agcattttga tgtcggtgat ttatgacagc    12840
atgtttaaat cgataaatca tgatatgcct tttcacaggt cttttgcgta tcccgcaatg    12900
ctcgttgtat ttttattatc actcttattg ttagcttttt tattttcaaa gtcgattcat    12960
tctttgctgc ataaaatcaa tctattgaat caaaccattc ggcatctggc gagtgatcaa    13020
aaggtgccag ataaaataga agtgaaacgt gctgatgaaa tcggggaact gactaagtcg    13080
gtcaatttgc taattgaacg aacgacatac cgtgaactgg aactgaggca gcaggaggga    13140
attaaaaagg agcttttgca aaaactgcgg catgacatta atacacccttt aaccgctctc    13200 aggctgcagt tattttattt ggaaggccaa tgtcatgatc aggctgtatt tgaatcattg    13260
tatcagcaaa tccactatat cgcggaatta acaaatgaat tcaatctata ttccgctgag    13320
acattagaaa ggtcttatat cataaatgaa gaagtgagtc taaacgaact gttagaaaca    13380
gctgtgaaaa agtgggatta tttatacagt atgaatggaa ttgagctgct ctataagccg    13440
gcagatcaag atatgatatg ggtgagcaac cggttatgga tgcaaaggct gttcgataat    13500
atttttcaaa acacgttaaa gcattcaaaa gctaaaaaaa tggaagtcat gattgaacat    13560
gggactgttt ctatttgcga tgacgggatt ggatttgatc gagatgagaa cagtgagggg    13620
cttgggttaa agattattga ggatatatgc aggctgcttc atattacgta ccttttaaaa    13680
acagataaaa caggaactca tttcaattta aaaaatgata aattgtaaac cccttagaat    13740
gaatatgcaa ggggttttg gtatggagag aaaccgctca ttacatataa aattaattaa    13800
aagagtgcaa gtggtatgtt gaggatgaag aatttatata ataaatagaa ggtgtttatg    13860 atcatttttgg gttttttgta aagtgtattc gagagaattt tcgggatcca ttccataaag    13920
atagtatgcg ttttatatga taaagagata agattattcc atttttttctt ttcttatcag    13980 ctcaataaaa ttaaatgccg atgtcgagat gacatcatca tttctccagc ataacgaaat    14040
agggttagta acatccacat gttccacatt aattctttta acatctcctc ttgatatata    14100
gcgattgact tcaaggaagg aaacaaatgt tataccatac ccttctatga cagtattaat    14160
ggtctcattt agcccgttca tttgtaatcc tgtgcatggc ttattcacat tgaacagatt    14220
gcataaagag aacaataatt ctctagaaaa actcccttcc tcgcgaaaaa caaacggttc    14280
ttttacaatt tctgctaatg tggtggtttg ttctgcatat ttgtgtttgt tattggagat    14340
aaataccatt tcatcctcca ataataatgt actgctaata tgtttattaa atgtcctgtt    14400
tccgccaata ataccgatgt cagctttata atttactagt tgacttatgg cttctgttga    14460
attgactgtg gtaatttcca catcaacatc cgggtactct cctttaaaac ggctgatcca    14520
cttcgggagt aaaaaattag ctggtaaact agttgccacg atgtgcaact ttcccacaga    14580
gccttctttt agatgttcca ggtaggattc aatctcattt tggagcgaga ataatctctt    14640
tgcttgttta gctagctgga gccctgtttg cgttaaataa attcctcttc ctctagggct    14700
aagcaaagtt agtccaattt cttttctctag ttttttaatc tgagctgtca cagcaggctg    14760
acttatattt agttttttttg cggcgcatgt gacatttccc tcctcagcta cagtgtagaa    14820
cagtctcaat gcatgaagat tcatcgttca tctctccatt cataaaaaat aattatgatt    14880
```

```
acaaaaaata tatatattag aatattccat ttagctatat tattataaat tcacatataa    14940
aacttcaata aatttctatt ttcaggtggt gaggggacag cttgatgtct agcgaaatat    15000
gaaacttgta tgtattgact gtggacagga aatgtcttct gatgatttta agtatcaatg    15060
ttcttgtggt ggactggttg atattgttca tgattttcct cattacgata ccgaccattt    15120
aaagcatgta tttcatgaac gtctatctga acgtatgtct gttttgcaa gcggagtatg     15180 gagatacaaa gagcttatat atccagattt gccagttgag agtattgtta caaaatatga    15240
agggaacaca gggttatacc gctctgagat gctatcgaaa taccggag tgagaaaggt      15300 atatctaaag gcgcaaagtg aaaccccag cggttcgttt aaggataacg gcatgactgt     15360
tgctgtttca catggaaaac atttaggtta tgaaaaatac gcctgtactt ctaccgaaaa    15420
cacttcttca tcattgggaa tgtatgcttc tattgcaaat gcttcatcct acgttttgt    15480 accggataaa gaaatttcaa ttaataaagt attgcagaca gcagcttacg gtggaaacgt    15540
attcagtatt ccgggaactt atgatgacgg tatcaggttt ttggaaaagt atagtggtga    15600
ttttggtttt tatatatgca attctattaa ccctttcaga attgaaggcc aaaagagcat    15660
tatttatgag atagctcaat atctagactg gaaattgcct gattggatta ttgttcctgg    15720
cggtgctctt agcaatgcaa cggctttagg gaaaggactc cgcgatttat atgctttaaa    15780
cttcatagac aagataccct gggtagctat catacaagcg gaaggcgcca gtccatttca    15840
tcaaatgatt agtaaaaata agaaacaat tgacccggaa ccatttccgt acactagagc     15900
ttctgcattg aatataggaa atcctcctag ctggaaaaaa gcgagaaagg ttttggaaga    15960
tacaaatgga atcactgttt ctgttacaga tgaggacatt cttgatgcaa aagcaataat    16020
cgacagaaca ggagtgggct gtgagcctgc ctctgcctct actgcagcag gactccgtca    16080
attgaggtca cagcaggtaa tagacaaaga tgaatctgtt ttgtgtattt taacaggcaa    16140
tatattaaaa gatactgggg ctctccacga ttaccacttt ggaaaagatt tgaacggcaa    16200
gtttaaaaac aatattaaat ctgccgagct atcatttgga aagataaaat cagcgatgga    16260
gacgattcgt gatttgaatg gtttattaaa gattcattaa ttaatcaaaa gacagtacaa    16320
gagaggagga aaagcgatta gcattttaat actgaacaaa acctcatatt ctaaatctcc    16380
gtatgattta tggctaaagg atttagaaga acctgttgta atgctgactt caactgaacg    16440
gttgcacgaa tgcaaaaact atgatcagat cgagtcattt gatgagtatc cggttaatgg    16500
atgtattgaa atcagagcgc tggaattaca tgaaacatat agttttaaca ccataattgc    16560
aatgtctgag tatgatcttt taagagcagg taaacttcgt actcatttag gattgaaagg    16620
gcagtcttat gagagtgcac tattgtttcg ggacaaagtt ttaatgaaac agcgtttgga    16680
agaacagggg attcctgttc cccattaccg gaaaattgaa tccccggttg acctgtacct    16740
ttttgtacag cagtttggtt ttccggtagt agtcaagcca atagatgggt cgggatctgt    16800
cgatacaaag gtgctaaaaa atgaaaaaga catgatgaaa tacttatcta agggtcttga    16860
tggaaatgtt gaagtggaaa cgtttgtaga tggtgatatg taccatattg atgggcttat    16920
gatagacgga catattacat taaattggcc ctctcggtat ataaacggat gtttggcttt    16980
ccaagaggaa caattttag ccagttatca gcttggcgct gacaacccat tgacctccag     17040
attaattggc attgttgaaa aagcactaaa ggcgctgcca tccccaaaaa caactacttt    17100
tcacgcggaa gtgttttcata ctccggatga taagctagtg ttttgtgaga ttgctagccg    17160
gactggaggg gggttaatac gtgaggctat tcagcaagga tttggttttg acttgaatga    17220
ggtttgtgtg aaaaaacagt gcggcctgcc ctatgatatt ccagattatt cacagcttaa    17280
```

```
aatagggcca aaacagttag gcgggtggat tttgatccct cctaaatacg ggcggttggt   17340
caaaattcct tcaattcctt ttgagaattg ggtaacaaag caaaaagtgt ctgctagaga   17400
aggagaggtg tttcagggtg cttcttctag tgtagacgtt gtatcaagtt acttaattaa   17460
agggaattcg gaagatgtac tgatcaatag aattcatcaa gttgcctcat ggtgcagtga   17520
aaatatgatt tgggaaggca atcaacgtg ttctctcaaa taaaagagtt tttcggatta    17580
catccggtca ttaagttttt gcttttggga actcttgtca caaaagcagc aaaatcaatg   17640
acaacaccgt ttttggctat ttacctccac caagaaacag gagagggttt cggtgtaatt   17700
ggcttggtaa ttggcttggg gtattttgcg actacgattg gaggaatcat ggaggaacc    17760
ctttccgaca gaatcggcag aaaaagtgtt atgttatgtt ccatttttat ttggagtgtt   17820
gttttctttc tttttggcat cgttcataca atattatggt tcagtttgtt aaatatttta   17880
agcggtctgt gtcattcctt tttcgagcca gtttcaaaag ctttaatggt tgaattagcg   17940
gatagaaaga agaggctcag cattttttct ttacggtatc tggccattaa tattggcggt   18000
gctctaggtc cgctattagg aacatatctg ggactggtga gcagcggaac ccctttattt   18060
attactggtt ctgtatatct ttgttatgct cttttgttat tttttatgat gaataaactg   18120
cttctgcaaa ataaaagcaa ttcaaaaaaa gaatttcatt tgccatttat atttaagaca   18180
ctgaaaaagg atattgctct tcgtttttat atagcaggcg ggatattctt gttatttagt   18240
tattctcaga tggagagtac cttgcttcag tacctgaacc ttgatttcgt gaacggcgtg   18300
aagatattct caactttaat aaccataaat gctgtaactg tcattatatt gcagttgcca   18360
ttaacacgcc ttttttgaaag atataaatca atgacaacga tttctgcggg aagcgtgtgt   18420
tgtatcatcg ggaatattgg ttttgcttta tcaaacggtt ggcttacttt ctgtatttct   18480
atgtttatat taactgtggg cgaaatccta tgttttccat caatgaatgt attaatggat   18540
gagttggccc ctgatagtat gaggggaact tattatggag cgcagaattt ttataatgta   18600
ggggagttta taggcccgtg gcttggaggc attatcctca gccttttggg cggtacaacc   18660
attttcttag ttgcagcttt gtctatctgt tttgctttaa cagcatatcg tatcggcaac   18720
agaaagcata gattcgttca actttatgaa gctgaagtta tgaataaata attattaagt   18780
tatttttat aagggggagaa tttgatttga actcaactgc agaaagaatg ctgagtacac   18840
ttacagaaaa caactataca cattttaccg gagtgccatg ttcattatta aaaggttttt   18900
ttaggctgct ggaatcaaaa gaggctatag aaaaacaaaa tattcacttt atcccctcca   18960
ttagagaaga ttctgcttta ggcgttgcat ccggtatgta tctaggcggg agaaaatgcg   19020
tgatgctgat gcaaaattca ggcttaggat actgcttaaa tgttcttacg tcctttaact   19080
tcatatatga tattcctatt ttattactaa ttagctggag aggggcatac ggtaatgatg   19140
ctgttgaaca tgcataatc ggtgaaaaac tcactgattt actcgattca gtggacattc    19200
cttacaaaga gctggattat gaaaattctg aaggaacgat attagatgcg cttttttaa    19260
tcgagaagac aaaccgtcct gttgcgatat taattaaaga tgaaatatag gaggtgtcag   19320
tttgaataaa catgacgcaa ttcagcttat tttaggacag tttccatcag catacttggt   19380
tagtacatgc ggtcatataa gccgtgattt gtacaacata aatgacagag ccagaaattt   19440
ttacatggtt gggtccatgg ggatggccgc tcctgtcgga ttgggattgt ctaccgtgta   19500
tcctgatgtt cctctggttg tgctagatgg agatggatcg tttttaatga atatggggat   19560
tattacgatg atcggtcatc aaaaacctaa aaatttttata catgttgttt tggataacgg   19620
tatgcatgaa agtacgggcg gacaaaggac ggttcctcta gtgaatgtaa cagatatagc   19680
```

```
tttacaagtt gggtatgagt atgccattga aatcaattca gggcagaaaa gttttgattt   19740
gcctaacgag ggtccgggac tcatccatat taaagttgaa ccacgaagcg aaaaaatcgg   19800
caaaagagta cattggacac cgcaagaaat agtccagcgt tttacaaatg aattaacttt   19860
agaaaatgag gtttcagtat gaaaatgcaa ttaatagatt gtacacttcg ggacggcggt   19920
aatttcaata actggttttt ttcagctgaa gacatcaatc aaattatcct gcatctagat   19980
aaagccaatg taaatataat agaaatcggt tatataggag gttcaggtag caataaagaa   20040
aaatctgtcg ggagtttagc caactgtaca cctgaacttt tagaacagct gccgaagacg   20100
atccattcac atttagcggc gatggttgtt ccatctgttt gtgagcttca tctattggac   20160
aacctgaatc cgcagctgat tccatggatt cgcgttgctt cgtatcctca taatgccgaa   20220
gatgctttac cgtatattga atacctaaaa aatcgaggtt ttcacgttag ttttaatgta   20280
atggcagcca gttatattga agagaaagac atggctgagc tagcgaaaaa atcgcatgtt   20340
tttggtgcgg atgtgtttta tatggctgat tctttcggga atctaacgcc tgatggtgtt   20400
agaaaaaggg tagcagctgc atttgaccag gcggattgcc cagttggttt tcacggacat   20460
aacaatcttg gattagcctt tacaaatgct cttgaagcaa tggatgcggg agcaactttt   20520
atagatactt cattatgtgg aatggctcga ggagcaggaa accttccaac agaacaattt   20580
gtaagtgcaa tacatcattg ggacaagttc ggcgacatcc catacaaact catccaatt   20640 ttaactgcgg ctgaatatgt actatcttcc atcctatctt caccaatgaa aatttccacc   20700
ccagagatta taagcggaat cagcaacatc cattactatt tctatgattt agtcatttca   20760
aagtgccgag aagtaaatct tgatcccttg caagtatcaa cattacttgg acaaacctta   20820
cctaaaagag ttgatatgtc ttacattgaa tcagttattg atcaaaattt tagacaggag   20880
agtgcaaaat gaaagctaaa aaattacgtg agttgctata ttcaaatcaa gttgtgcgag   20940
taatggggcg cataatggt ttaagcgcta aacttgctga acaagccggg ttccatgcaa   21000
tatgggccag cggattagaa atttcggcat cttatgctgt tcctgatgct aatattttga   21060
ctatgacaga aaatctgcaa gccgcagtcg tgatgaatga atctacatcc atcccaatca   21120
tttgtgattg cgattctggt tatggaagtg tgaacaatgt catacgtatg gtaaaagaat   21180
atgaaagaaa cggaattgct ggtatttgta tagaagataa gcaatttcct aaattaaata   21240
gttttgtgaa gggctcgcaa aaattggcag atattgatga gttctcaaat aaaatcagag   21300
cggcaaaaga tgttcaaaaa aatcctgatt ttgttgttat tgccagaata gaagccttaa   21360
ttgcgggtca aggaatggat gaagcattaa acagagccta tgcttatgag gcagcaggag   21420
ctgatgccat tctgatccat tcgaaagaaa accagccaaa cgaaattaag gaattcgtaa   21480
aacagtttac tggagcagta cctattgtga ttgtacctac gacatacccg catataaccg   21540
tgaaagaaat ggagttattg ggcatcaata tggtcattta tgccaaccac ggtcttagaa   21600
gttctattaa ggcaatgcaa gagacattct cccagattct ccttgatgga aatacggtag   21660
gtgtagaaga taacattgtg tctatgaaaa ctgttttcga acttcaaggt atgtatgaca   21720
tgagaaaaca agaagatatg tataactccg gcacttctgt catcagtact atcaaataaa   21780
ataagatagg agtaatttag aatgatttct gaccaatata atattgtttc actagcatat   21840
ttacattcaa aaattaattt ttttattgaa ccgtcattat cattagacca tgttttttgat   21900 ttttttcagta cacactttt tattaacagg ggaagacatg aagaagatcg tttggctgat   21960
gtatacatga ctcataataa agaagaattt caaacgatag actttaataa cggtgaggat   22020
atttatatca gaaaaagtgc tactgattat ttcaccattc cttgtaaacg agtaactgtt   22080
```

```
gaagggattg aatatgttaa atgtacaaaa acagatacga tcctttcatt tgataaagaa    22140
aacaagaaaa taatcatttc tacacagtta caaaatgcag agcaggatga actggtttta    22200
attgagttca ttagagattt agtattgaaa aatgaagaga accatggtgt ggcggtggtg    22260
catgcgacca gtgcgttaaa agatgacaaa gcaactctca ttataggttc aaaagggaaa    22320
ggcaagtcaa ctttattgct ggaattagtg agtaaacacg ggtacaaact cataagcggt    22380
gataagactt ttcttttggat ggaagatggg aaattacggg cctcagggtg gccggattat    22440
cctcatttgg gactcggcac actttctaaa tatccggaat tcgtcgaaca cttcgggctc    22500
tctaataaaa ttgaatcagt aaaagaaaat ctttggtcaa ctgaacataa aatggccatt    22560
gatccggttt tttttaagaa ggttattcct tttgcagaac cagggacatc atttatggtc    22620
gaatgtatga tttaccctga tctatttcct tcaacagaat gcggaatcaa gcaggtaagt    22680
aatcatggtg aattgattgt accgcatata gaaaggattt ttacgaaagg gaacacgatg    22740
tggaaccatt atattcggcc tgtacatcag aatgaactgg agagaaaaat aaatcagtgt    22800
attgagcttg ctggaaagct ttctgctttt gaagtgagcg gatcaggcat tttagagggt    22860
tcagtgttta gcgagagata cgctctgtaa tcttttgaaaa tttggaaata aaggagaaaa    22920
ataaagtggt tgaaatcacg attcaatcaa aagggtttaa tcacagttat gacattacag    22980
aacaagtaac agacgcatta tctcaattag agccatcttc aggtttagca aaggtctgtg    23040
taaccggcag tacggtaggt ctcactgtta tgcgttatga accaggcacc atacacgact    23100
tgctccaatg tttagagtcc attgcttcaa aaaataaaca atatgaacac tttaacacga    23160
ccggtgatcc aaatggcttt tcacatgtgt ggtcttcaat gattgggaca agtgtgatgg    23220
ttccatacaa aaatcataag ctagcttgtt cggacagcca tagggtcgta ttatttgatt    23280
ttgatttaag ggaagcagaa cgaaaaatct atgtagatcg ttaatgaata tattagggga    23340
gttgtttgag atgaggaagt tacgatggc tactccggga cctacgcaag ttccgcagga    23400
aattttattg gcgggagcac aggaaatgat tcatcaccga tcccggcaaa tggaggatat    23460
tattaatgaa attaatcgtg aactcccaga tcttttttg acaaaacaag atatttatat    23520
tttgttatct tcaggtacgg gggctatgga ggctgctgta tcaaactcct ttaataggg    23580 ggataaagtt ttagtcgtct ctaatggtta ctttggagag cgtttactg atatctgtac    23640 agtattcggt ttagaggtga taaccgtaag ctctccttgg ggaacttctg ttaatattga    23700
agaagttgaa agagcgtata agcagcatcc ggatataaag ggagtgctca ctgtttacag    23760
tgaaacctca acgggagcag ttaatgatgt aaaggccatt ggatcattgt tcagagatac    23820
agaggtgctg gtgattgttg atgctataag cggccttatt tctcatgagc tatcaatgga    23880
tgattgggga ttagacatag tattagcagc ctctcacaaa ggatttatga tgccgccggg    23940
cttagcgttt gttgctattt cgccgaaagc ttggaaagtg attaatgaaa ttcagccttc    24000
aacttactat ttttcattta aagatttaa aaaattttat cctatggcac cttcaagtcc    24060
gggtgtatct ttactattag cattaaaaaa atcactagat ttattgaaag cagaaggcct    24120
ttcgaatgct accagacgac atgcccgtat cgctagggca acgcaaagag gattggaagc    24180
tttaggtttt caccttttg tacaatctcc tcatgttaga agtcatacag tgacagcagc    24240
gttagctcca tcgggaattg atgcagcttt attattaaaa aaactaaata agaatatgg    24300 acttacgata acaggggggtc aaggtgagtt taagggaag atgatcagga ttggacatat    24360
tggagctatt gatgaaattg atttgttcgg aatattcgga ataatggaat tggtgttaac    24420
agaaatgggt tatcaggttc agtctgggat cagcatgact gctttgagtg atgcattagg    24480
```

```
aggggagtc atacaccatg cttaaattat atcagaggga accatgtcct tattgcaaac    24540
cggtaagaga gaaattaact gagctgaatg taacgtatat caatgtgaat cttccgaagg    24600
atcgtgcttt acgaacagaa ttaatagaaa aaacaggcgt tccttatata cccgctttaa    24660
ttgatgaaga agataacgtt atcatttcag gtaaactgga atacaaccag catgtcttgg    24720
attatataga aaaaaagttt ggccaaaatc gttaaggggg attcttcttc ttgcgctatg    24780
ccttcataac agatatacat gggaaacgtg ataatcttga aaaggttttg gagcatatcc    24840
aaaccttttc ttctatacat gagatcattt gttgtgggaga tgtttttgaa gttaaggttc    24900
ctaaaaagga tttaaaagat tttcagtttc agtgcatgga acaagtttta gatttggatt    24960
gggaattaat gaatttgtta aaagatattc gagtgataaa aggtaatcaa gaggagagga    25020
tattaagtct gatcccagag aaagaatttc cgaaagactt ttacaacttt ttgattcaca    25080
tgcctttaga aattcattta actccaatgg tcagattaac gcatggccat acttttgatt    25140
ggacgggaga agaagattat tggaggccca gcaatgttca ttattggagc agcccgtgga    25200
tcttttatgg tcataaccac caaaatgtac tgtttgaagt taaggagata gagaataatc    25260
cttattatga acggaaaagc attataaacg gtaagcctat cacattagac tctgcatctc    25320
gttatttgat caatataggt gatatgaaat atgatcatcc tagttggatg cttttggata    25380
cattggaaaa tcagattact tacaatatat tgtattgaaa aggagtttat tctgatgctt    25440
cgtattttac tcattaattc cgataaacca gagcctattc agttttttca aaaagataag    25500
gaaacaaatg attctatcaa tatatctgtc attacgagat cgtgctatgc ccctctttat    25560
tcacattggg cagatcatgt atacatcgtt gatgatgtaa cagatttaac ggtgatgaag    25620
agtttgatgc tggagatatt aaaagtgggg ccaattgatc atattgtttc aacaaccgaa    25680
aagagtatat taacaggcgg gtttcttcgc tcctattttg ggatagccgg gcctggattt    25740
gaaacagctc tttatatgac gaataaattg gcaatgaaga ctaaacttaa aatggaaggg    25800
attcctgttg cagatttttt gtgtgtaagc caagtagagg atatccctgc agcaggcgag    25860
aaactaggct ggcctattat tgtaaagccg gctcttggtt cgggcgcctt aaatactttt    25920
atcatccatt cattagatca ttacgaagac ctgtattcaa catcgggtgg tttaggcgaa    25980
ctaaagaaga ataactcact tatgattgct gaaaaatgta tagaaatgga agagtttcat    26040
tgtgatactt tatacgctga cggagaaatt cttttttgtat caatatcaaa atatacagtg    26100
cctttgctaa aaggaatggc taaaatccaa gggtcattta ttttgagtca aaatgatccg    26160
gtttatgctg aaatattaga acttcagaag tctgttgctc aagcgtttcg tatcacagac    26220
ggtcccgggc atcttgaaat atacagaacc cattcaggtg aactgatcgt cggtgagatt    26280
gcaatgcgta ttgggggcgg agggatcagc cgcatgatag aaaaaaaatt caatatatct    26340
ttatgggaaa gttctcttaa catttccgta tatagagatc caaatctcac ggtcaatcca    26400
atagagggaa ctgtcggata cttagcttg ccttgccgaa acgaacaat aaaagaattt    26460 acgcccatcg aggaatggga aaagcttgct ggcatactgg aggttgaatt gttataccaa    26520
gaaggtgatg ttgtagatga aaagcaaagt tcaagttttg atctggccag gctttatttt    26580
tgtttagaaa atgagaatga agtacaacat ctattagctc tagtcaaaca aacatattat    26640
cttcacttaa cagaggatca tatgatgaac caataatgtt catatgtttt agggcttcac    26700
ttgaatgtag ctgttgtcta agagatgttt ttctttctcc tataaactct atataatagg    26760
aagaaagaaa tgaggtgatc agcatatgtt taaaaaaatc attaaaacga tcaagcacct    26820
ctcaagcagc tcgagtgatc gctatcgcag acaccggcat taccgcagct acagcagctc    26880
```

```
aggtaaaaga agacactacg accgttatgg cggcagtcat cgctataagc gccggagcta    26940
cagcagcagt taatctcaaa aaaagttctt gttccgtctt gggacaaggg ttttttttatg   27000 tgaccgattg aatcgcgcgg ttcaggtctt cgcgaatcaa agcggtgttc tggtattctt   27060
cctcgatgcc taataatttt ttcagcagca aggttacttc ttttgtgagc gttaattcct   27120
caagccaggt gccgttttc ttctttttc ctttatattg agagtacagc aggaataaca    27180
gtgtttctcc gagatcgaag aagtcatcct gtttcctcac ctttacttcc tcagtttctt   27240
caggagtcaa ttgctttgta aggccgaaat cgatgagaca gagcctgccg ttattgatga   27300
tcatattagg cgttctgatg tcgctgtgaa aaatgaggcg ttcatgcagg tattctacaa    27360
tctcaagcag ctgagaaatc agctgtaacg ccataagctc tgtaaacggc tgttttgaa    27420 aaaataataa ttcctctata ttttctccat caaagaactg catgacataa taagcttgcc   27480
cgtctatgat gaaatcatcc ttgaagtccg ggatttgcgg gtggtgaatg cttttgagca   27540
gttttatttc ctgctggaac cggactcttt cttttccttt ttcgctttt gtcggccgga   27600 gctgttttaa gacataagat gtttgagtat ggacatcggt gcacaaataa accaacccat   27660
agccgcccat tccgaggcat tcttcgattc tgtattgatg atttagaata cgccgtcct    27720 ttagaggacg gtcaaaaagt agcttttttta gctgttttaa tgccatgtct gcacttccct   27780
tggttgtact gagtatagtt tatcaaaaca attgcattct aggctaagtc aatgggagct    27840
aagcataaaa aagagccggc tcatggaagt tgaaccagct cagtatgaat taaaattgct   27900
ttgtgacatc gtattcataa tctattttg cttttacatt actcatcgtc gatctagcag    27960
ttgctaaagt attatattta aaactccata ccttagcgac actgagttga tctgacaatg   28020
atatatcata gaccctgac gtcgagctat tcacaagtgc acgcgccat tcgttatttt     28080 cgctcgtcat gatgaagtgg cgtgtatttc cctggctggg tgtttgagtg gcggttgttt   28140
gtactctagt aacaatggca tcgcgcggta ttccagattg gtttgttaaa tcaaccttga   28200
tcacactgga gtcagaacct gaggggctaa gggtggtatt tcctttattt tcagcaacgc   28260
cgctgaattg gaatgttccg ctgccggatt tgattcggtc ttcaattgaa agtgtaaaat   28320
acatgttccc ggtataggtg ccgcgtgaca cttttcacata gaagggatct gtcgtgtttt   28380
gggcgtcagc attggcataa ataaaagaag agaacgtatt aggattaatc acttctgtgc   28440
cttgcgaaac aggtactctg ttcttatcgt aaatttcaat tttcatccct gtgtacgcgc    28500
tctggtatgt acttctcacg tatactttt ctcccttata agctgtaaaa gtgaaatagg    28560
cttcatcttg tccggcttcc agtatcgttg tatcgatatt cttatatttc caatatccga   28620
ttggtgctgc ggtatcaaat gaattgtttc ctgtaatagc agtaactccg gcagctgatg   28680
ccgaataagt aaaggtgaag aagacagcca gcataataac gaatggaaag agccatttt    28740 tcatcttgta acaacctcc ttttatttcc atcatacata ataacgcttt aagtgtaaat     28800
aaatgtttct tgaggttaat atatacattg gtattgccga taaaatagag taagagagaa   28860
ttgttaagga gggaacccaa tgcgtctgaa tcggcaattt atccgtactc agctgatggc   28920
acagaacata ttgaatagga atgcggctgc tacacgcgaa atacgtctg aaaatacagc    28980 aacagtgctg gaacaggcat acagcaggcc tgagtcacga tcttcaaatg agggaatcaa   29040
tcagttcaat tattctaaag ccagcgtgac aggaaacaat gggactttca gcaaagtgta   29100
tcaatcagcg aatgatcgaa cagtgacaga tacaggggag gaaacagtga ttcaatccaa    29160
aaacccctat gaatctgaga gtgatatcag aatcaaaata cttgatgaaa aatacagcag    29220
aatgaatgcg attaacaaaa cgaagtctga tccattaggc tatataaagg ataagtacca   29280
```

```
aaattcaaag tctccttatt tcagaagtga tctgtcagct gcagaaagac aggctgctta   29340
cgataatgaa acagaatggc tattcaaagg taaggcccaa aactataacc tgcaggatgc   29400
cgcatttcgc aatgtcatgt ttaatgggga agtggaggct gagaatgaaa aggtgtatca   29460
gcgaagccag gttaaccagc agctgcaagt actgttgaac cgaaaccata ttcacattcc   29520 gcagggggaca gagctgacgt ttacgattac gccgattgac tataaggtac aggtgagcgg   29580
gacagacgat caggcactga ttgagcaaat tgagcaagtg ctgcaatctg gagacaacag   29640
caaagagcta tttttacata tcatgaaaag cctaagcggt gattcaacac aattttccga   29700
agaggcatat caaaagtatc aagctgctcg tgagatgtac aagtcacag gctatcattt   29760 gaaggattta gaagtgattg acgggcggta cgtaacgcct gatggacgtg atttattaga   29820
cgtatatcaa gaagagcttg aaaaagatcc tttgcaaaaa caaacggctt cttatgctat   29880
atctcactat cgttcagagc tcagtaaaat ggcggaagcc gggtatgatg ccattccgga   29940
tttcatcata tcaattgatt atagcaatgg atctctgaga gatgtggggc aaagcaagag   30000
ctatggcacc ggagatacca agtggcttga gacattaaag ctccaaacag gtgtgaatta   30060
ttaaaaagct gttcattgtg aacagcttat ttttatgag aatcttagaa gatgtataat   30120
ttcaatattc aaacaatatt attatattta tataaaagaa tttaaatgaa gcatacgatt   30180
aaaaactctg aataaatgtg tttgcctgaa aaaacaatt gtattttcca gagaaattta   30240
ttatgatgaa ataagtaatt aaggagatta taacgatt ttacgtttga attttctgat   30300
tgttataact gattggtgag aaagataagc aggcctgcta ttttctcatt ttcgagtatt   30360
atgtaagagg gggaagagga gtggcaaata aagaattaaa gaggggcctg ggcgcgcgtc   30420
atattcagat gattgccttg gcggtacga tcggtgttgg tttgtttatg ggttctgcca   30480
gcacgatttc atggactggt ccgtctgtcc ttttggctta tgcaatatgc ggaatttta   30540 tctttttttat tatgcgtgca atgggtgaaa tgctgtatgt cgaaccgagt acaggttctt   30600
ttgcgacatt cggccataac tatattcatc ctctggcagg ttatatgaca gcatggagca   30660
actggttcca atggattatc gtcggcatgt cagaaattat cgctgtcggt tcatatatga   30720
agtattggtt cccggatttg cctgcttgga tacctggtat cgtggcaatg gtgattcttg   30780
gtgcggcgaa cttaatttct gttaagtcgt tggtgagtt tgagttttgg tttgcgatga   30840
ttaaaattgt gacaattatc ttgatgatta ttgcaggatt cgggattatt ttcttcgggt   30900
ttggcaacgg cggagatgcg atcggcttgt cgaacctgtg gtctcatgga ggattctttg   30960
caggcggttt ctctggattc ttcttttgcgc tgtctctcgt cattgctgcc tatcaaggtg   31020
ttgagctaat cgggattaca gccggtgaag cgaaggaccc gcaaaacacg ctaagaagtg   31080
cgattcaaag tattatctgg cgtattttga ttttctatat tggcgctatt tttgtgatcg   31140
tgaccgtgta tccttgggat gagctcaact cacttggaag tccgttcgtg tctacgttct   31200
cgaaaatcgg aattacggca gcggccggaa ttattaactt tgtcgtcatt actgcggcaa   31260
tgtccggctg taacagcggt attttcagtg caggacgcat gctttataca ttaggcgtca   31320
atggacaagc gccgaaattt tttaagaaga tttcacgcaa tggtgtgccg ctctatggca   31380
caattgcggt gctgatcggt ttggcaatcg gtgttgtgct gaactatgtt gcgccgccga   31440
agatctttgt ctatgtatac agtgcaagtg tgctgccggg catgattcct tggtttatca   31500
ttttgatcag ccatatcgga ttcaggaaag cgaagggtgc cacattagat aaacatccat   31560
ttaaaatgcc gtttgcacct ttcacaaact acttgacgat tgcttttcttg ctgatggttc   31620 tggtcggcat gtggtttaat gatgatacgc gtatctcgct gattgtaggc gtgatttttct   31680
```

```
tagcgcttgt ggtcattagt tattatgtgt ttgggattgg caaacgtacg caggccaatt    31740
tgacaaaaag tagccaagcg gctgaataag catagaaaaa gagacattca cggatgtctc    31800
tttttttatt tttcgcgtat ggattttccc tattttagca agctataagg taaagatagc    31860
aaaaggaaag gtgtgcataa aatggatgtt acactcggtt atttgcgcga atcactttcg    31920
aatcatcttg aaaatgaagt ctgccagcgg atttgcaaga agatgctagg gaagcggtat    31980
gtaaatgaag aggaatttgt aaaagactta gatgacaatg aaatgtcttt tttgaaccat    32040
gtattagaaa aagaaattaa gtatgcgcag aatgaacagg atcaaaaacg ggccaaggaa    32100
ttaaacgagg tgtatgaatt actgctttga aaggcgggta agaaatggga gcaattgaac    32160
gaagcggata tacatttcag ccggagttta gcgtcgtccg acaaaatgga gccatccatg    32220
tgtaccgtca cggagaattt gtggaagaaa tcgaatttga atttaacgga gaatatcctg    32280
atcatgattt gattgaagag cttgtgaatc attattgttt tgagcatgac atttagagcc    32340
ctgcctattt gcagggctcc tttatttagg atgtgatcaa gccatacttt ttcaggatat    32400
ccactgtgat gttttggct tttgtaccgg aatcatcgac attggtgaca aaaatatacg    32460
agccatgctc tgttttgatg aatccgacaa accagcctaa tcccatatct gtcaggcggg    32520
ttccggtttt tccgtagagt gtgtagtgat ctccttcctc ttgaatcatc atgcgcttga    32580
cggttttcat caccgatttg tcaaatgaaa gctcctcgtt tacaagtttc tccaaaaagg    32640
cttcttgttc cagcggagat attgtcagcg agctttgcag ccaaaactgg tcgatccccc    32700
cgctgatatc ctcattgccg tatgacgaga tatgaagcca tgttttcatc ctttcctcac    32760
cgatatctct cgctaatgct tgataatacc agatggcgga ttcccgcatg gccgagccta    32820
gcgtatggtc gcggttccat gattcgaatt cgcgcttgac cccgtcccac cgtttgacat    32880
cgtattcatc ccgaacagct tttacctgta acccgattaa ggcgttcacg accttaaagg    32940
tggactgcgg agtttgtctt ttgtttgccc gttctctgtt gtagacaaaa gtcttgtcct    33000
tttgcacatc gtgaaaaatg aaggttccga ccgtatcatt gaattcgtca tcgacattca    33060
tttggctgac attcagatgt tttttatggg cagacgatga tgcgtgaacg gaaaagccgc    33120
cgatccctgc aatactcagc acaagcacaa catatatcca tttcttcatt ttgttctccc    33180
ctttgtttta atcaactacc ttttctctat ttcttctgtt cttcctttaa atactgctca    33240
taaaaacgct taaatttggt tccgaaaaca aatactgtta ttgggtttat gcttgtagga    33300
taaagtgaaa atagagagta aaaaggaagg cagggttacg agatgaatga gcagattcca    33360
catgacaaaa gcctcgataa cagtgtggct ttgatgcggg aaggatattt gtttataaag    33420
aatagaaaag agcattacca ttcggatttg tttcaggcac gtttgctagg aaaaacatttt   33480 atttgtatga gcggggcaga agctgcgaag atattttatg ataccgaacg atttcagcgg    33540
caaggtgctc tcccgaaacg agtgcaaaaa tcgctgtttg gcgtcaatgc gatccagacg    33600
atggatggcg acgcgcatat tcatcggaag ctgctgtttt tgtcattaat gacacctccg    33660
catcaaaaac ggctggctga gctgatgaca gaggagtggg aagcggcagt cacgagatgg    33720
gagaaggcag atcaggttgt attatttgag gaagcaaaag aaatcctatg ccgggtagcg    33780
tgctattggg caggtgttcc gctgaaggaa acggaagtca aagagagagc ggatgacttc    33840
attgatatgg ttgacgccctt cggagctgtg gggccgcggc attggaaggg tagaagagca    33900
aggccgcgtg cggaagagtg gattgaaaga atgattgaag atgtccgtgc gggcttgctg    33960
aaaatacctg ccggaacagc gttgcatgaa atggcgtttc acactcaaga agatggcaac    34020
cagctggatt cccggatggc cgccattgag ctgattaatg tactgcggcc tatcgtcgcc    34080
```

```
atttcttact tcttgtgtt ttcagcttta gcgcttcata agcatccgaa gtataaggaa    34140
tggctgcgtt ctggaagcag ccgggaaaga gaaatgtttg tgcaggaggt ccgcagatac    34200
tatccgttcg gtccgttttt aggggcgctt gttaaaaagg attttgaatg gaataactgt    34260
gagtttaaga agggcacatc ggtactgctt gatgtatatg gaacgaatca cgaccctcgc    34320
ttatgggaca accctgatga atttcggcct gaacgatttg cggagtggga ggaaaatccg    34380
tttgatttga ttcctcaagg tggaggtcac gcggagaaag gcatcgctg tccaggggaa    34440 ggcattacga ttgaagtcat gaaagcaagc ctggattttc tcgtcaatca gattgaatac    34500
gaggttccgg aacaatcact gcattacagt ctcgcgagaa tgccgtcatt gcctgaaagc    34560
ggttttgtga tgagcggaat cagacggaaa aggtaaaata taaaagctct cttccttatc    34620
gaagagagct ttttggttac ttcttttttt catcgtagta ttggacggga tacatggagc    34680
cttctgatac cattttgttg tcctcgatat cttgagggtc cgggtggccg gctttatcga    34740
ctgggaacgt ttccatgtct ggctgttttg ttatttcat tttcatgctg tgaatgaatt    34800
ctttagcttt ttggcgattt gacgggtctt ttaatagata agaagtgatg ctgacagttg    34860
aaacagcgag acctgaaagt aacagctttt gtttcatggt gatactcctt tctatttaa    34920 gagtagtgtt tcctgtatca ttcccgtttt gattatggct aaacctttgc cgatttattt    34980
agggaaactg ttcagcgatt gtgcctgtta ttctttgcgg ctggtatact gaaagctctg    35040
tgggaaagaa taactgtgat gagaaaacct tgcgatatca cgcaaggttt tttgtagtcg    35100
attggtcatg ttcatcgcga aatattacac caatgtaaac gtttaatagg accataaggc    35160
ttattgttaa gttattgtaa attaagtgga tgttttattt acaatcatct gaacttgaaa    35220
cataatcgaa gagagtttgc tgaataatgt ctaaacagag gtgaa               35265

<210> SEQ ID NO 2
<211> LENGTH: 296
<212> TYPE: PRT
<213> ORGANISM: Bacillus subtilis

<400> SEQUENCE: 2

Met Asn Leu His Ala Leu Arg Leu Phe Tyr Thr Val Ala Glu Glu Gly
1               5                   10                  15

Asn Val Thr Cys Ala Ala Lys Lys Leu Asn Ile Ser Gln Pro Ala Val
            20                  25                  30

Thr Ala Gln Ile Lys Lys Leu Glu Lys Glu Ile Gly Leu Thr Leu Leu
        35                  40                  45

Ser Pro Arg Gly Arg Gly Ile Tyr Leu Thr Gln Thr Gly Leu Gln Leu
    50                  55                  60

Ala Lys Gln Ala Lys Arg Leu Phe Ser Leu Gln Asn Glu Ile Glu Ser
65                  70                  75                  80

Tyr Leu Glu His Leu Lys Glu Gly Ser Val Gly Lys Leu His Ile Val
                85                  90                  95

Ala Thr Ser Leu Pro Ala Asn Phe Leu Leu Pro Lys Trp Ile Ser Arg
            100                 105                 110

Phe Lys Gly Glu Tyr Pro Asp Val Asp Val Glu Ile Thr Thr Val Asn
        115                 120                 125

Ser Thr Glu Ala Ile Ser Gln Leu Val Asn Tyr Lys Ala Asp Ile Gly
    130                 135                 140

Ile Ile Gly Gly Asn Arg Thr Phe Asn Lys His Ile Ser Ser Thr Leu
145                 150                 155                 160

Leu Leu Glu Asp Glu Met Val Phe Ile Ser Asn Asn Lys His Lys Tyr
```

```
                        165                 170                 175
Ala Glu Gln Thr Thr Thr Leu Ala Glu Ile Val Lys Glu Pro Phe Val
            180                 185                 190

Phe Arg Glu Glu Gly Ser Phe Ser Arg Glu Leu Leu Phe Ser Leu Cys
        195                 200                 205

Asn Leu Phe Asn Val Asn Lys Pro Cys Thr Gly Leu Gln Met Asn Gly
    210                 215                 220

Leu Asn Glu Thr Ile Asn Thr Val Ile Glu Gly Tyr Gly Ile Thr Phe
225                 230                 235                 240

Val Ser Phe Leu Glu Val Asn Arg Tyr Ile Ser Arg Gly Asp Val Lys
                245                 250                 255

Arg Ile Asn Val Glu His Val Asp Val Thr Asn Pro Ile Ser Leu Cys
            260                 265                 270

Trp Arg Asn Asp Asp Val Ile Ser Thr Ser Ala Phe Asn Phe Ile Glu
        275                 280                 285

Leu Ile Arg Lys Glu Lys Met Glu
    290                 295

<210> SEQ ID NO 3
<211> LENGTH: 433
<212> TYPE: PRT
<213> ORGANISM: Bacillus subtilis

<400> SEQUENCE: 3

Met Lys Leu Val Cys Ile Asp Cys Gly Gln Glu Met Ser Ser Asp Asp
1               5                   10                  15

Phe Lys Tyr Gln Cys Ser Cys Gly Gly Leu Val Asp Ile Val His Asp
            20                  25                  30

Phe Ser His Tyr Asp Thr Asp His Leu Lys His Val Phe His Glu Arg
        35                  40                  45

Leu Ser Glu Arg Met Ser Val Phe Ala Ser Gly Val Trp Arg Tyr Lys
    50                  55                  60

Glu Leu Ile Tyr Pro Asp Leu Pro Val Glu Ser Ile Val Thr Lys Tyr
65                  70                  75                  80

Glu Gly Asn Thr Gly Leu Tyr Arg Ser Glu Met Leu Ser Lys Tyr Thr
                85                  90                  95

Gly Val Arg Lys Val Tyr Leu Lys Ala Gln Ser Glu Asn Pro Ser Gly
            100                 105                 110

Ser Phe Lys Asp Asn Gly Met Thr Val Ala Val Ser His Gly Lys His
        115                 120                 125

Leu Gly Tyr Glu Lys Tyr Ala Cys Thr Ser Thr Gly Asn Thr Ser Ser
    130                 135                 140

Ser Leu Gly Met Tyr Ala Ser Ile Ala Asn Ala Ser Ser Tyr Val Phe
145                 150                 155                 160

Val Pro Asp Lys Glu Ile Ser Ile Asn Lys Val Leu Gln Thr Ala Ala
                165                 170                 175

Tyr Gly Gly Asn Val Phe Ser Ile Pro Gly Thr Tyr Asp Asp Gly Ile
            180                 185                 190

Arg Phe Leu Glu Lys Tyr Ser Gly Asp Phe Gly Phe Tyr Ile Cys Asn
        195                 200                 205

Ser Ile Asn Pro Phe Arg Ile Glu Gly Gln Lys Ser Ile Ile Tyr Glu
    210                 215                 220

Ile Ala Gln Tyr Leu Asp Trp Lys Leu Pro Asp Trp Ile Ile Val Pro
225                 230                 235                 240

Gly Gly Ala Leu Ser Asn Ala Thr Ala Leu Gly Lys Gly Leu Arg Asp
```

-continued

```
                245                 250                 255
Leu Tyr Ala Leu Asn Phe Ile Asp Lys Ile Pro Arg Val Ala Ile Ile
            260                 265                 270

Gln Ala Glu Gly Ala Ser Pro Phe His Gln Met Ile Ser Lys Asn Lys
        275                 280                 285

Glu Thr Ile Asp Pro Glu Pro Phe Pro Tyr Thr Arg Ala Ser Ala Leu
    290                 295                 300

Asn Ile Gly Asn Pro Pro Ser Trp Lys Lys Ala Arg Lys Val Leu Glu
305                 310                 315                 320

Asp Thr Asn Gly Ile Thr Val Ser Val Thr Asp Glu Asp Ile Leu Asp
                325                 330                 335

Ala Lys Ala Ile Ile Asp Arg Thr Gly Val Gly Cys Glu Pro Ala Ser
            340                 345                 350

Ala Ser Thr Ala Ala Gly Leu Arg Gln Leu Arg Ser Gln Gln Val Ile
        355                 360                 365

Asp Lys Asp Glu Ser Val Leu Cys Ile Leu Thr Gly Asn Ile Leu Lys
    370                 375                 380

Asp Thr Gly Ala Leu His Asp Tyr His Phe Gly Lys Asp Leu Asn Gly
385                 390                 395                 400

Lys Phe Lys Asn Asn Ile Lys Ser Ala Glu Leu Ser Phe Gly Lys Ile
                405                 410                 415

Lys Ser Ala Met Glu Thr Ile Arg Asp Leu Asn Gly Leu Leu Lys Ile
            420                 425                 430

His

<210> SEQ ID NO 4
<211> LENGTH: 407
<212> TYPE: PRT
<213> ORGANISM: Bacillus subtilis

<400> SEQUENCE: 4

Val Phe Ser Gln Ile Lys Glu Phe Phe Gly Leu His Pro Val Ile Lys
1               5                   10                  15

Phe Leu Leu Leu Gly Thr Leu Val Thr Lys Ala Ala Lys Ser Met Thr
            20                  25                  30

Thr Pro Phe Leu Ala Ile Tyr Leu His Gln Glu Thr Gly Glu Gly Phe
        35                  40                  45

Gly Val Ile Gly Leu Val Ile Gly Leu Gly Tyr Phe Ala Thr Thr Ile
    50                  55                  60

Gly Gly Ile Ile Gly Gly Thr Leu Ser Asp Arg Ile Gly Arg Lys Ser
65                  70                  75                  80

Val Met Leu Cys Ser Ile Phe Ile Trp Ser Val Val Phe Phe Leu Phe
                85                  90                  95

Gly Ile Val His Thr Ile Leu Trp Phe Ser Leu Leu Asn Ile Leu Ser
            100                 105                 110

Gly Leu Cys His Ser Phe Phe Glu Pro Val Ser Lys Ala Leu Met Val
        115                 120                 125

Glu Leu Ala Asp Arg Lys Lys Arg Leu Ser Ile Phe Ser Leu Arg Tyr
    130                 135                 140

Leu Ala Ile Asn Ile Gly Gly Ala Leu Gly Pro Leu Leu Gly Thr Tyr
145                 150                 155                 160

Leu Gly Leu Val Ser Ser Gly Thr Pro Phe Ile Ile Thr Gly Ser Val
                165                 170                 175

Tyr Leu Cys Tyr Ala Leu Leu Leu Phe Phe Met Met Asn Lys Leu Leu
            180                 185                 190
```

```
Leu Gln Asn Lys Ser Asn Ser Lys Glu Phe His Leu Pro Phe Ile
            195                 200                 205

Phe Lys Thr Leu Lys Lys Asp Ile Ala Leu Arg Phe Tyr Ile Ala Gly
        210                 215                 220

Gly Ile Phe Leu Leu Phe Ser Tyr Ser Gln Met Glu Ser Thr Leu Leu
225                 230                 235                 240

Gln Tyr Leu Asn Leu Asp Phe Val Asn Gly Val Lys Ile Phe Ser Thr
                245                 250                 255

Leu Ile Thr Ile Asn Ala Val Thr Val Ile Ile Leu Gln Leu Pro Leu
            260                 265                 270

Thr Arg Leu Phe Glu Arg Tyr Lys Ser Met Thr Thr Ile Ser Ala Gly
        275                 280                 285

Ser Val Cys Cys Ile Ile Gly Asn Ile Gly Phe Ala Leu Ser Asn Gly
290                 295                 300

Trp Leu Thr Phe Cys Ile Ser Met Phe Ile Leu Thr Val Gly Glu Ile
305                 310                 315                 320

Leu Cys Phe Pro Ser Met Asn Val Leu Met Asp Glu Leu Ala Pro Asp
                325                 330                 335

Ser Met Arg Gly Thr Tyr Tyr Gly Ala Gln Asn Phe Tyr Asn Val Gly
            340                 345                 350

Glu Phe Ile Gly Pro Trp Leu Gly Gly Ile Ile Leu Ser Leu Phe Gly
        355                 360                 365

Gly Thr Thr Ile Phe Leu Val Ala Ala Leu Ser Ile Cys Phe Ala Leu
370                 375                 380

Thr Ala Tyr Arg Ile Gly Asn Arg Lys His Arg Phe Val Gln Leu Tyr
385                 390                 395                 400

Glu Ala Glu Val Met Asn Lys
                405

<210> SEQ ID NO 5
<211> LENGTH: 167
<212> TYPE: PRT
<213> ORGANISM: Bacillus subtilis

<400> SEQUENCE: 5

Leu Asn Ser Thr Ala Glu Arg Met Leu Ser Thr Leu Thr Glu Asn Asn
1               5                   10                  15

Tyr Thr His Phe Thr Gly Val Pro Cys Ser Leu Leu Lys Gly Phe Phe
            20                  25                  30

Arg Leu Leu Glu Ser Lys Glu Ala Ile Glu Lys Gln Asn Ile Thr Phe
        35                  40                  45

Ile Pro Ser Ile Arg Glu Asp Ser Ala Leu Gly Val Ala Ser Gly Met
    50                  55                  60

Tyr Leu Gly Gly Arg Lys Cys Val Met Leu Met Gln Asn Ser Gly Leu
65                  70                  75                  80

Gly Tyr Cys Leu Asn Val Leu Thr Ser Phe Asn Phe Ile Tyr Asp Ile
                85                  90                  95

Pro Ile Leu Leu Leu Ile Ser Trp Arg Gly Ala Tyr Gly Asn Asp Ala
            100                 105                 110

Val Glu His Asp Ile Ile Gly Glu Lys Leu Thr Asp Leu Leu Asp Ser
        115                 120                 125

Val Asp Ile Pro Tyr Lys Glu Leu Asp Tyr Glu Asn Ser Glu Gly Thr
    130                 135                 140

Ile Leu Asp Ala Leu Phe Leu Ile Glu Lys Thr Asn Arg Pro Val Ala
145                 150                 155                 160
```

```
Ile Leu Ile Lys Asp Glu Ile
                165

<210> SEQ ID NO 6
<211> LENGTH: 186
<212> TYPE: PRT
<213> ORGANISM: Bacillus subtilis

<400> SEQUENCE: 6

Leu Asn Lys His Asp Ala Ile Gln Leu Ile Leu Gly Gln Phe Pro Ser
1               5                   10                  15

Ala Tyr Leu Val Ser Thr Cys Gly His Ile Ser Arg Asp Leu Tyr Asn
            20                  25                  30

Ile Asn Asp Arg Ala Arg Asn Phe Tyr Met Val Gly Ser Met Gly Met
        35                  40                  45

Ala Ala Pro Val Gly Leu Gly Leu Ser Thr Val Tyr Pro Asp Val Pro
    50                  55                  60

Leu Val Val Leu Asp Gly Asp Gly Ser Phe Leu Met Asn Met Gly Ile
65                  70                  75                  80

Ile Thr Met Ile Gly His Gln Lys Pro Lys Asn Phe Ile His Val Val
                85                  90                  95

Leu Asp Asn Gly Met His Glu Ser Thr Gly Gly Gln Arg Thr Val Pro
            100                 105                 110

Leu Val Asn Val Thr Asp Ile Ala Leu Gln Val Gly Tyr Glu Tyr Ala
        115                 120                 125

Ile Glu Ile Asn Ser Gly Gln Lys Ser Phe Asp Leu Pro Asn Glu Gly
    130                 135                 140

Pro Gly Leu Ile His Ile Lys Val Glu Pro Arg Ser Glu Lys Ile Gly
145                 150                 155                 160

Lys Arg Val His Trp Thr Pro Gln Glu Ile Val Gln Arg Phe Thr Asn
                165                 170                 175

Glu Leu Thr Leu Glu Asn Glu Val Ser Val
            180                 185

<210> SEQ ID NO 7
<211> LENGTH: 337
<212> TYPE: PRT
<213> ORGANISM: Bacillus subtilis

<400> SEQUENCE: 7

Met Lys Met Gln Leu Ile Asp Cys Thr Leu Arg Asp Gly Gly Asn Phe
1               5                   10                  15

Asn Asn Trp Phe Phe Ser Ala Glu Asp Ile Asn Gln Ile Ile Leu His
            20                  25                  30

Leu Asp Lys Ala Asn Val Asn Ile Glu Ile Gly Tyr Ile Gly Gly
        35                  40                  45

Ser Gly Ser Asn Lys Glu Lys Ser Val Gly Ser Leu Ala Asn Cys Thr
    50                  55                  60

Pro Glu Leu Leu Glu Gln Leu Pro Lys Thr Ile His Ser His Leu Ala
65                  70                  75                  80

Ala Met Val Val Pro Ser Val Cys Glu Leu His Leu Leu Asp Asn Leu
                85                  90                  95

Asn Pro Gln Leu Ile Pro Trp Ile Arg Val Ala Ser Tyr Pro His Asn
            100                 105                 110

Ala Glu Asp Ala Leu Pro Tyr Ile Glu Tyr Leu Lys Asn Arg Gly Phe
        115                 120                 125
```

His Val Ser Phe Asn Val Met Ala Ser Tyr Ile Glu Glu Lys Asp
         130                 135                 140

Met Ala Glu Leu Ala Lys Lys Ser His Val Phe Gly Ala Asp Val Phe
145                 150                 155                 160

Tyr Met Ala Asp Ser Phe Gly Asn Leu Thr Pro Asp Gly Val Arg Lys
                165                 170                 175

Arg Val Ala Ala Ala Phe Asp Gln Ala Asp Cys Pro Val Gly Phe His
                180                 185                 190

Gly His Asn Asn Leu Gly Leu Ala Phe Thr Asn Ala Leu Glu Ala Met
            195                 200                 205

Asp Ala Gly Ala Thr Phe Ile Asp Thr Ser Leu Cys Gly Met Ala Arg
210                 215                 220

Gly Ala Gly Asn Leu Pro Thr Glu Gln Phe Val Ser Ala Ile His His
225                 230                 235                 240

Trp Asp Lys Phe Gly Asp Ile Pro Tyr Lys Leu His Pro Ile Leu Thr
                245                 250                 255

Ala Ala Glu Tyr Val Leu Ser Ser Ile Leu Ser Ser Pro Met Lys Ile
                260                 265                 270

Ser Thr Pro Glu Ile Ile Ser Gly Ile Ser Asn Ile His Tyr Tyr Phe
                275                 280                 285

Tyr Asp Leu Val Ile Ser Lys Cys Arg Glu Val Asn Leu Asp Pro Leu
                290                 295                 300

Gln Val Ser Thr Leu Leu Gly Gln Thr Leu Pro Lys Arg Val Asp Met
305                 310                 315                 320

Ser Tyr Ile Glu Ser Val Ile Asp Gln Asn Phe Arg Gln Glu Ser Ala
                325                 330                 335

Lys

<210> SEQ ID NO 8
<211> LENGTH: 296
<212> TYPE: PRT
<213> ORGANISM: Bacillus subtilis

<400> SEQUENCE: 8

Met Lys Ala Lys Lys Leu Arg Glu Leu Leu Tyr Ser Asn Gln Val Val
1               5                   10                  15

Arg Val Met Gly Ala His Asn Gly Leu Ser Ala Lys Leu Ala Glu Gln
                20                  25                  30

Ala Gly Phe His Ala Ile Trp Ala Ser Gly Leu Glu Ile Ser Ala Ser
            35                  40                  45

Tyr Ala Val Pro Asp Ala Asn Ile Leu Thr Met Thr Glu Asn Leu Gln
50                  55                  60

Ala Ala Val Val Met Asn Glu Ser Thr Ser Ile Pro Ile Ile Cys Asp
65                  70                  75                  80

Cys Asp Ser Gly Tyr Gly Ser Val Asn Asn Val Ile Arg Met Val Lys
                85                  90                  95

Glu Tyr Glu Arg Asn Gly Ile Ala Gly Ile Cys Ile Glu Asp Lys Gln
                100                 105                 110

Phe Pro Lys Leu Asn Ser Phe Val Lys Gly Ser Gln Lys Leu Ala Asp
            115                 120                 125

Ile Asp Glu Phe Ser Asn Lys Ile Arg Ala Ala Lys Asp Val Gln Lys
            130                 135                 140

Asn Pro Asp Phe Val Val Ile Ala Arg Ile Glu Ala Leu Ile Ala Gly
145                 150                 155                 160

Gln Gly Met Asp Glu Ala Leu Asn Arg Ala Tyr Ala Tyr Glu Ala Ala

```
                    165                 170                 175
Gly Ala Asp Ala Ile Leu Ile His Ser Lys Glu Asn Gln Pro Asn Glu
            180                 185                 190

Ile Lys Glu Phe Val Lys Gln Phe Thr Gly Ala Val Pro Ile Val Ile
        195                 200                 205

Val Pro Thr Thr Tyr Pro His Ile Thr Val Lys Glu Met Glu Leu Leu
    210                 215                 220

Gly Ile Asn Met Val Ile Tyr Ala Asn His Gly Leu Arg Ser Ser Ile
225                 230                 235                 240

Lys Ala Met Gln Glu Thr Phe Ser Gln Ile Leu Leu Asp Gly Asn Thr
                245                 250                 255

Val Gly Val Glu Asp Asn Ile Val Ser Met Lys Thr Val Phe Glu Leu
            260                 265                 270

Gln Gly Met Tyr Asp Met Arg Lys Gln Glu Asp Met Tyr Asn Ser Gly
        275                 280                 285

Thr Ser Val Ile Ser Thr Ile Lys
    290                 295

<210> SEQ ID NO 9
<211> LENGTH: 362
<212> TYPE: PRT
<213> ORGANISM: Bacillus subtilis

<400> SEQUENCE: 9

Met Ile Ser Asp Gln Tyr Asn Ile Val Ser Leu Ala Tyr Leu His Ser
1               5                   10                  15

Lys Ile Asn Phe Phe Ile Glu Pro Ser Leu Ser Leu Asp His Val Phe
            20                  25                  30

Asp Phe Phe Ser Thr His Phe Phe Ile Asn Arg Gly Arg His Glu Glu
        35                  40                  45

Asp Arg Leu Ala Asp Val Tyr Met Thr His Asn Lys Glu Glu Phe Gln
    50                  55                  60

Thr Ile Asp Phe Asn Asn Gly Glu Asp Ile Tyr Ile Arg Lys Ser Ala
65                  70                  75                  80

Thr Asp Tyr Phe Thr Ile Pro Cys Lys Arg Val Thr Val Glu Gly Ile
                85                  90                  95

Glu Tyr Val Lys Cys Thr Lys Thr Asp Thr Ile Leu Ser Phe Asp Lys
            100                 105                 110

Glu Asn Lys Lys Ile Ile Ile Ser Thr Gln Leu Gln Asn Ala Glu Gln
        115                 120                 125

Asp Glu Leu Val Leu Ile Glu Phe Ile Arg Asp Leu Val Leu Lys Asn
    130                 135                 140

Glu Glu Asn His Gly Val Ala Val Val His Ala Thr Ser Ala Leu Lys
145                 150                 155                 160

Asp Asp Lys Ala Thr Leu Ile Ile Gly Ser Lys Gly Lys Gly Lys Ser
                165                 170                 175

Thr Leu Leu Leu Glu Leu Val Ser Lys His Gly Tyr Lys Leu Ile Ser
            180                 185                 190

Gly Asp Lys Thr Phe Leu Trp Met Glu Asp Gly Lys Leu Arg Ala Ser
        195                 200                 205

Gly Trp Pro Asp Tyr Pro His Leu Gly Leu Gly Thr Leu Ser Lys Tyr
    210                 215                 220

Pro Glu Phe Val Glu His Phe Gly Leu Ser Asn Lys Ile Glu Ser Val
225                 230                 235                 240

Lys Glu Asn Leu Trp Ser Thr Glu His Lys Met Ala Ile Asp Pro Val
```

```
                    245                 250                 255
Phe Phe Lys Lys Val Ile Pro Phe Ala Glu Pro Gly Thr Ser Phe Met
            260                 265                 270
Val Glu Cys Met Ile Tyr Pro Asp Leu Phe Pro Ser Thr Glu Cys Gly
        275                 280                 285
Ile Lys Gln Val Ser Asn His Gly Glu Leu Ile Val Pro His Ile Glu
    290                 295                 300
Arg Ile Phe Thr Lys Gly Asn Thr Met Trp Asn His Tyr Ile Arg Pro
305                 310                 315                 320
Val His Gln Asn Glu Leu Glu Arg Lys Ile Asn Gln Cys Ile Glu Leu
                325                 330                 335
Ala Gly Lys Leu Ser Ala Phe Glu Val Ser Gly Ser Gly Ile Leu Glu
            340                 345                 350
Gly Ser Val Phe Ser Glu Arg Tyr Ala Leu
        355                 360

<210> SEQ ID NO 10
<211> LENGTH: 132
<212> TYPE: PRT
<213> ORGANISM: Bacillus subtilis

<400> SEQUENCE: 10

Val Val Glu Ile Thr Ile Gln Ser Lys Gly Phe Asn His Ser Tyr Asp
1               5                   10                  15
Ile Thr Glu Gln Val Thr Asp Ala Leu Ser Gln Leu Glu Pro Ser Ser
            20                  25                  30
Gly Leu Ala Lys Val Cys Val Thr Gly Ser Thr Val Gly Leu Thr Val
        35                  40                  45
Met Arg Tyr Glu Pro Gly Thr Ile His Asp Leu Leu Gln Cys Leu Glu
    50                  55                  60
Ser Ile Ala Ser Lys Asn Lys Gln Tyr Glu His Phe Asn Thr Thr Gly
65                  70                  75                  80
Asp Pro Asn Gly Phe Ser His Val Trp Ser Ser Met Ile Gly Thr Ser
                85                  90                  95
Val Met Val Pro Tyr Lys Asn His Lys Leu Ala Cys Ser Asp Ser His
            100                 105                 110
Arg Val Leu Phe Asp Phe Asp Leu Arg Glu Ala Glu Arg Lys Ile
        115                 120                 125
Tyr Val Asp Arg
    130

<210> SEQ ID NO 11
<211> LENGTH: 393
<212> TYPE: PRT
<213> ORGANISM: Bacillus subtilis

<400> SEQUENCE: 11

Met Asn Ile Leu Gly Glu Leu Phe Glu Met Arg Lys Leu Arg Met Ala
1               5                   10                  15
Thr Pro Gly Pro Thr Gln Val Pro Gln Glu Ile Leu Leu Ala Gly Ala
            20                  25                  30
Gln Glu Met Ile His His Arg Ser Arg Gln Met Glu Asp Ile Ile Asn
        35                  40                  45
Glu Ile Asn Arg Glu Leu Pro Asp Leu Phe Leu Thr Lys Gln Asp Ile
    50                  55                  60
Tyr Ile Leu Leu Ser Ser Gly Thr Gly Ala Met Glu Ala Ala Val Ser
65                  70                  75                  80
```

Asn Ser Phe Asn Arg Gly Asp Lys Val Leu Val Ser Asn Gly Tyr
                85                  90                  95

Phe Gly Glu Arg Phe Thr Asp Ile Cys Thr Val Phe Gly Leu Glu Val
            100                 105                 110

Ile Thr Val Ser Ser Pro Trp Gly Thr Ser Val Asn Ile Glu Glu Val
            115                 120                 125

Glu Arg Ala Tyr Lys Gln His Pro Asp Ile Lys Gly Val Leu Thr Val
    130                 135                 140

Tyr Ser Glu Thr Ser Thr Gly Ala Val Asn Asp Val Lys Ala Ile Gly
145                 150                 155                 160

Ser Leu Phe Arg Asp Thr Glu Val Leu Val Ile Val Asp Ala Ile Ser
                165                 170                 175

Gly Leu Ile Ser His Glu Leu Ser Met Asp Asp Trp Gly Leu Asp Ile
            180                 185                 190

Val Leu Ala Ala Ser His Lys Gly Phe Met Met Pro Pro Gly Leu Ala
            195                 200                 205

Phe Val Ala Ile Ser Pro Lys Ala Trp Lys Val Ile Asn Glu Ile Gln
    210                 215                 220

Pro Ser Thr Tyr Tyr Phe Ser Phe Lys Arg Phe Lys Lys Phe Tyr Pro
225                 230                 235                 240

Met Ala Pro Ser Ser Pro Gly Val Ser Leu Leu Ala Leu Lys Lys
                245                 250                 255

Ser Leu Asp Leu Leu Lys Ala Glu Gly Leu Ser Asn Ala Thr Arg Arg
                260                 265                 270

His Ala Arg Ile Ala Arg Ala Thr Gln Arg Gly Leu Glu Ala Leu Gly
            275                 280                 285

Phe His Leu Phe Val Gln Ser Pro His Val Arg Ser His Thr Val Thr
    290                 295                 300

Ala Ala Leu Ala Pro Ser Gly Ile Asp Ala Ala Leu Leu Leu Lys Lys
305                 310                 315                 320

Leu Asn Lys Glu Tyr Gly Leu Thr Ile Thr Gly Gln Gly Glu Phe
                325                 330                 335

Lys Gly Lys Met Ile Arg Ile Gly His Ile Gly Ala Ile Asp Glu Ile
            340                 345                 350

Asp Leu Phe Gly Ile Phe Gly Ile Met Glu Leu Val Leu Thr Glu Met
            355                 360                 365

Gly Tyr Gln Val Gln Ser Gly Ile Ser Met Thr Ala Leu Ser Asp Ala
    370                 375                 380

Leu Gly Gly Gly Val Ile His His Ala
385                 390

<210> SEQ ID NO 12
<211> LENGTH: 85
<212> TYPE: PRT
<213> ORGANISM: Bacillus subtilis

<400> SEQUENCE: 12

Met Leu Lys Leu Tyr Gln Arg Glu Pro Cys Pro Tyr Cys Lys Pro Val
1               5                   10                  15

Arg Glu Lys Leu Thr Glu Leu Asn Val Thr Tyr Ile Asn Val Asn Leu
            20                  25                  30

Pro Lys Asp Arg Ala Leu Arg Thr Glu Leu Ile Glu Lys Thr Gly Val
        35                  40                  45

Pro Tyr Ile Pro Ala Leu Ile Asp Glu Glu Asp Asn Val Ile Ile Ser
    50                  55                  60

Gly Lys Leu Glu Tyr Asn Gln His Val Leu Asp Tyr Ile Glu Lys Lys
65                  70                  75                  80

Phe Gly Gln Asn Arg
                85

<210> SEQ ID NO 13
<211> LENGTH: 215
<212> TYPE: PRT
<213> ORGANISM: Bacillus subtilis

<400> SEQUENCE: 13

Leu Arg Tyr Ala Phe Ile Thr Asp Ile His Gly Lys Arg Asp Asn Leu
1               5                   10                  15

Glu Lys Val Leu Glu His Ile Gln Thr Phe Ser Ser Ile His Glu Ile
                20                  25                  30

Ile Cys Leu Gly Asp Val Phe Glu Val Lys Val Pro Lys Lys Asp Leu
            35                  40                  45

Lys Asp Phe Gln Phe Gln Cys Met Glu Gln Val Leu Asp Leu Asp Trp
        50                  55                  60

Glu Leu Met Asn Leu Leu Lys Asp Ile Arg Val Ile Lys Gly Asn Gln
65                  70                  75                  80

Glu Glu Arg Ile Leu Ser Leu Ile Pro Glu Lys Glu Phe Pro Lys Asp
                85                  90                  95

Phe Tyr Asn Phe Leu Ile His Met Pro Leu Glu Ile His Leu Thr Pro
            100                 105                 110

Met Val Arg Leu Thr His Gly His Thr Phe Asp Trp Thr Gly Glu Glu
        115                 120                 125

Asp Tyr Trp Arg Pro Ser Asn Val His Tyr Trp Ser Ser Pro Trp Ile
    130                 135                 140

Phe Tyr Gly His Asn His Gln Asn Val Leu Phe Glu Val Lys Glu Ile
145                 150                 155                 160

Glu Asn Asn Pro Tyr Tyr Glu Arg Lys Ser Ile Ile Asn Gly Lys Pro
                165                 170                 175

Ile Thr Leu Asp Ser Ala Ser Arg Tyr Leu Ile Asn Ile Gly Asp Met
            180                 185                 190

Lys Tyr Asp His Pro Ser Trp Met Leu Leu Asp Thr Leu Glu Asn Gln
        195                 200                 205

Ile Thr Tyr Asn Ile Leu Tyr
    210                 215

<210> SEQ ID NO 14
<211> LENGTH: 11000
<212> TYPE: DNA
<213> ORGANISM: Streptomyces plumbeus

<400> SEQUENCE: 14
tgacgaactg gacgccgagc aggacggtgt acgtccgccg ggggccgaac cggtccgcca      60
gcccgcccag cggcacggca ccggccaggg cgacggtccc ggcgatcgtc agaccggagg     120
cgacctggtg cacgggcagg cccacgaccc gggtgaagaa caggggtgccg gtggtcaggt    180 acagcccgct gccgaccgtc ttgaccagcc aggacacggc cagcagccgg gggtcgccgg    240
gcgcgggcag cgcggcgtcg agcagacggc gcgccctgcc gggagccggt gcgctcatgc    300
cccgtgcccc gccatcgtgt gcagccgcgc gatgaagcgc tccgcggccg gctcgtcctc    360
ggccgcgaag taggcctcca gacgcccggg gctggcgcac tcctcgggtg tcagcacctc    420
cagcacgccg ggcagggcca gcacccgcgc gcgcagaccg ggcagcgcgg gcaggcgggct  480

```
gcggccgacc gtgccggcgc ggggttcgcg ggcgggccgg ccgggccgct caccggccga    540
gacccggacg aactcctccc acaggtccac cccgaaggcg tgccaccaca tccgggagat    600
gcccatcccg cccggccgta ccgccacttc gccgacgacc ggaccgtcct cggtgcggaa    660
cacctccaga tgggtgaccc cggccggcag gccgagcgtg gcgaccaccc ggcggtgcag    720
gtccaggacc tcccgcgaga acgcgtcgct ctggtcggcc aggtagccgc tgttcaggtc    780
cggagaggtg tgcagcggcg ggaggaagta gcggagacg gccgcgcggg ccacctcgcc    840
gccgtggacg acgccgtcgc agtggtactc gtgcgtgaac cgcaccaggc gctcgacctg    900
gaccggcagc cgggtgtccg cgaggtcggc gaagtctccg gcgcggtgcc gtcgcgcgaa    960
ctccccgggg gagtcgacgc ggtgggtgca cttcgaggcg cgccgaaca ccggcttgat    1020 catgacgggc cagccggtcc gctccgccgc gcgggcacc gcgtcgaggg tcgcggcctg    1080
cgcgtagtcc gtcaccggga tgcccgcggc gcgcagcctg tccttcatcg cgcgcttgtg    1140
ggcgccccgc agggactggt cgaacccggg cccgggcacc ccgagcaggg cgcggaccag    1200
cccggccgcc accacgctct ctccgtggc ggcgatgacg tggtcgacgg ggccgtgcgc    1260
ggcgatctcg tacgccgccc gctcgacctg agtgagatcg gcgaagctgt cgacgtacgc    1320
cgtctcgtgg ttctcgtaca ggcccgcgta caccgggcgg gtgatgacgc ggacggtcac    1380
acccgggcgg cgggccaggg cgtggaggac ctcgggtttg tccgagttga gcaggagtac    1440
ctgccgggtc actgcttctc cgtgggtcgg gggtccgtgg gtctgggtgtc caggggccgg    1500 ggggccgtgg ggtgcggtgc gtggtggtag gtgacggtgg acgcggcctc gtcgacgacg    1560
gcccaggcgg gggaggggcc gcggtccggg gcgcacgggg cgacggagcc gacgttgacg    1620
acgtagcggc cgtccggggc cagcgggatc ggcgtcccga accgcacggg cagccgctcg    1680
gcccgcaccg ggccggtacg ggtgggccac agccggtaca gcgcgctgcg gtgatggtgc    1740
ccgtgcacca gagcccggcc gggaaagtcc gcgtcggccg ggcaccacag tcccggctcc    1800
agctcgcgcc acggcagggg atggccgtgg cagtacaggg cgaagccggt gcggtgctcc    1860 cgggggggcgt ggagcagcgg acgggtccag ccgggcaggg cggcctcggg cacgagggcg    1920
cggatccgct cctcctggtt gccccgcacc agccgcaccc cgtccaggag ccgggcgagt    1980
tcggggtcgg ggtcgaacac gtccgtcagc cggcccccga acgcgtagcc ggccgcctcc    2040
cgtttcccga cccggcactc gaggacgtcg ccgagacaga tcacccggtc cacccgctgc    2100
tcacggatcg ccccgaggac cgcccgcagc cgggcggtgt ccccgtgaac gtccgtcacg    2160
acggcatggc gcacgccctc acccactcgt ctcgatccgt acccggcccg ccagcgcctc    2220
gcagacacgg gcggcgtcgg ccgcgtccgt gccgtcggcg atgacgtacc cggcgcggtc    2280
ctgcgagcgg cgcaccgggc ggaccgggtc gccgaccgtg acgtccagcc ggatctcggc    2340
ggtggtgccg ccggtgtcgg gcagggcgat ctcccgtacc gttccgggcg gcggggtgag    2400
gaagcggatc gccgctcccc ggcgggcggc gggcggggca ccgggcggcg ggagcagacc    2460
gaaggggcag cccgcggtga gggcgaccag gtccagtccg taggcgcggc gcagcagttc    2520
acggatcttg tcgccgccga tgcggttgtg cgactccagg atccgggggc ccttcgcggt    2580
gaccttgacc tcggtgtggg cggggccctc cgtcaggccg acgcgtcca ggaaggccac    2640 cacgagcgcg gtgacctcgc tcaggacggg cgcgggcagg cagctcggca gggtgtgccc    2700
ggtctcgacg aacgcggggc cggtcagttt gtcggtcacc gcgaggacgg tgtgccgtcc    2760
gtcgtgcgag aagctctcca cgctgatctc gggcccgtcg aggtactcct cggcgatggg    2820
cccggcgccg cccgccgcct cgaacgcccg ccagacggcc tcggcctccg cgggcccggc    2880
```

```
cacctcgaag acggcctgac tggccgtgcc ggcagcgggt ttgaggacga ccggcccgcc    2940
ggccgcacgg cagaacgcgg cgaggccgac cgcgtcacgc ggtgcggtgg tgcgcaccgg    3000
gccgatgcca cggcgttga gcacctcccg catgcgccgc ttgtcctgca gcaggtccac    3060
cgtgcgcagg gagttgccgg gcaggccgag ccgtccggcc accgcggccg ccggcagcag    3120
tccgctctcg gtgagggaca gcacgcgccc gaagggtgg gcggcgtgca gcggcgccag    3180
ggccgcgtgc agggcgtcgg tgtcggccag gtccacggcg acggccgtgc cggcctccgc    3240
ggccaccgcc ggcgccggcc gcgcccggtc gtgcacgagg acggtgccga tgcccagggc    3300
gcgggccggg cgcacgagtt gcggggtgcc cgcgaccacc gcgatgcgca gtgtcgcggg    3360
cacccgctgc ccgaaggtca tgcctcggtt cccggccgcg cctccgcgcc ggcgaccgcc    3420
gccggcgcca ccgtctccgg gtcgccgaag cgcttctcca gataggcgat gatgtcggcg    3480
ttctcgcgca gcctgcccgg gatgacggtg gcgccgtcga ccagggcggg gatgaacttg    3540
ctgcccgtcg tgcggatcaa ctcgtgccgt tcctcgcgcg gcttgggcac gttgacgttg    3600
atgtaggaga cctggagccg ggtgagcagt tcgcgcaccg gcttgcagtc cgggcaggtc    3660
tcccgctgga acaggacgag catcagcgac cctcctcgtg gaacgtgcgg atgatctcgc    3720
cgacgccgga gcccggcgtg aacgtgtggc ccaggtcgag cagggccatc tccagggcgc    3780
cgaagatccc gatcaggtcg agggagtcgg ccgcgcccac gtgcccgacc ggatgagcc    3840 tgcccttcag atgcgcctgg ccgccggtca tcgtgacccc gtacgacgtc gacagcgtct    3900
tcaggagccg gccggtgtcg atgccctcgg gggcgagagc cgcggtgatg acgtggctgc    3960
gccggtgcgg ggcctggacg aaggtgctga accgagctt cagcagaccg cgttcggccg    4020
ccttgcccag cacggcgtgg cgcgtgcgga aggcgtccgt gccctcctcg ccagcatct    4080 tcagcgactc gtgcagggcc agcagcaggg acaccgcggg ggacgacgag gacatcgggt    4140
agaagtggcg cagccgctcg aacgaccagt agtagttcgg cccggtggaa cgctccacgg    4200
ccgtccacgc cttgtcggac agggcgacga aggcgaggcc cggcggcagc atgaagccct    4260
tgtgggaggc ggcgaggacc acgtccaggc cccaggcgtc catctccagc gggtgcacca    4320
gcagaccgct gatggcgtcg acgaccgtga tcacgtcggt gtcgcggaag atccgcccga    4380
tcgcctcgac gtcgttgagc gccccggtgg acgtctcgct gtagaccacg aacgcgccgc    4440
ggatcgcggg gtgttcgcgg taggccgccg ccacccgctc ggggtcggcg ctggtgcccc    4500
agtcgctctc gacgacgtgc acgacgagac cgtacgacgc gcagatcgcc tggaagcgtt    4560
cgccgaagta gccgttggag acgaccagga cctcgtcgcc ggccgagaag cagttggcga    4620
ccgcggcctc catggcgccg gtcccggagg aggcgatggt gtacaccggg gaggcggtgc    4680
cgaacagcgg gggcaggccg ccgctgatct cgtggatcag ctgctccatc tcggtggagc    4740
ggtggtggat gatctcgcgg gccccggcca gcagcagacg ctgggggact tcggtgggcc    4800
cgggtgtggc cagccgcagc ttcacaggct cttctccgta accgtgtcgg tgtgggggc    4860 gggtgccgcg gtccggggcg cgtcgaggaa gacgcggcgg gtggcgggct tcaggtcgaa    4920
gtcgaagagc accacgcggt gactcggcga catggcgagg gcgccgtccc ggaagggcac    4980
gagcagactg tgccgagca gcgacgactt cagatgggag aagccgttgg ggtcctcggt    5040
ggtcagctcg tgcagatagc ggccggcgcc ggcggggac tccggcgcga tgcgttccag    5100
ggtccgcagc aggtcctgca cggcgccggg ctcgtagcgc atgacggtga gcccgatggt    5160
gctgccgtgc gcgaacaccc cggccagtcc gtcgcccgcg ccgtgctcgc ggaggctgtc    5220
ggcgatcgtg tcggtgaggt cgtagtggga gttgaggccg gtgctgtgca ccgtcagttc    5280
```

```
gatcacaggg ctgcctccgc gggcccggcg atcagcgccg gcacgttccg ggccgtcagg    5340
tcgccggggc cggtcagcgt ccaggccggc accccggcca ggacatcggt gatgcgggtg    5400
acgcgctcgg cgtgggcggc gcggtcgtcg tcgaggtagt ggtgccagcc ggcgttggcg    5460
ccgtcgaacg ccgactccac gttggcgcgc agcacttcgg cgtgctcctc gcggccgccg    5520
gtgagcggtt cgaccaccgt gtgctcaccg gggccgatcg acgggtgcag gatcgccgcg    5580
acgggcacgc gcaccccggc cggggcgctc gggaaacggt cccggaacgg cagcgggtcc    5640
acggcgaact cccccacggg cgagaacgcg tggccctcgg cgggcacgta gtcgtccgcg    5700
atgcccgcga tctccctgag cccggggtac ttggcgacgg tgccgtagcc caggtgcgga    5760
tagtcgggcc agccggccgc gaggacggag ccgtccggga gttcgtgcac cacggtcttg    5820
tcgccgctga ggatctcgta cccgaagtgc tccaccagct ccaggagcac cgtgctcttg    5880
ccggccccct tcgcgccggt gaccagcacg accgtgccgt cccggtaggc ggcggtcgcg    5940
tgcagcaccg cggcgccgtt gttctcctgg tgcttcagca ccaggtcgcg caccagctcg    6000
acgaggtcca tgtgtccgcc ggccccgagc gccacgtcga tcacacggga cgcccggtcg    6060
aagacgaagc ggctgcccgt cttggtgcac tccaggtact cccggccgtc caccgcggcc    6120
cgccgggccg gcacggtgaa gaattcgctg gcgctcttgc ggaggtggat gtcctccgcc    6180
gccgttccgg cgggaggcgc gagaagcccc gggtccccgg cgtgcacgcg cagcgtggcg    6240
accggctcgc ggcccgtctc gtcgggcttg gcctcctcgg cggtcagatg cgtggccagg    6300
aaggccagcg cgtcctcgag gcgggcaccg ggcgccacct ccaggtcgag cggggtgccg    6360
tggaagtcca gccgcagggc ggtgggtcgg gtggtcactg tgctgcctcc gcgagttcgc    6420
gtcccaggga ctcgtagcgc tcctgctgct ccagcatctg gggcatgcgc tgcaggtcga    6480
agatctcctt gagcggggcg agttcgggct ccacgttcag cgtggtgccg tcccgcatga    6540
tccgggtgag ggtctcccgc atggcccgga tcgagctgcg cagcgcctgg ttggcataga    6600
tcgccatggc gaatccgcgc tgctccagct cctcgacggt gacctggttg taggtggtcg    6660
gcacgacgat caccggaagg tcgccgcggt aggcctcgcg gaaggcgaag acctcctccg    6720
ggtccttgcg cttggagtgg atgagcaggg cgtccgcgcc ggcccgctcg tagacgtcgg    6780
cccggcgcag cgcctccgcc atgccctgcc cggagatcag cgcctccagc cgggccacca    6840
cgaccatgtc cgtacgggtc tcggaggcgc cccggatctt ggccgcgaag tcgtccagcg    6900
gggccagatc ctgattgccc tcgacgaagc tgttgagctt ggggaactgc ttgtcctcga    6960
tgcacacccc ggccacgccg cgcgcctcgt aggaacgcac catgtggatg acgttgttga    7020
cgttgccgaa tccggagtcg cagtcggcga gcacggggag gtccaccgag gacgccaggc    7080
cggccgccgc gtcgaggcac tcgcccatgg agaggatgtt ggcgtcgggc acgccggccg    7140
cggcggagat ctccagtccg ctggaccaga cgacgtcgaa gcccgcctcc tcggcgagcc    7200
gcgcgctgag cgggctgtgc gcgcccatgg cacgtgtcag ccgcggggcg gcgagcgccg    7260
cgcgcagccg ccgggccgct ccgtccggcg ggtcgttccg gtcctgctgg ggcggtcggc    7320
tcgcggtcat gcgttccctc cggtggtgtg ttcggtccct gcggtccgcc cggccagttc    7380
ccggcacacg tcctcgaccg tctcgtcgag gaccttgcgc ggcgggccg cgccgatccg    7440 gtgtccgacg gcccacgggt cgagtccgtg gcggcgctg atcttctcga tgcggtcctg    7500
gaagtagaag tggtggtcgt tgatcccggc cgcgatctcc gcccggcgca ccgtcatggg    7560
gcgcggcagc acctgttcgg ccacgtactc cgctgcctcg cagaccaggg gcagatcgac    7620
gtgggtgtcg taccgggccc acgcggtgag gaaggccgcg gcctgctcgg tcgcgaggtt    7680
```

```
cccggcgccc cgcgccatgg cgcacagcga ggcgtccagc cagctcacgc ccgcgtccag    7740
gccggcgagc gcgttggccg cggccaggcc gagattgttg tgggcgtgga tgccgagcgg    7800
gacgggcagc cgctcggcca gtagtccgac gcgcctgcgg acgtcgtccg gggtgagcgc    7860
gccgaaggag tcggcgatgt agaagacgtc cggccgctcg gacgccacga ccgcggcgac    7920
ctcggccagt tgctcctcgg tggtgtagct gacggccatc aggttcacgc cggccttcag    7980
cccgagcgcc cgcacggcac ggacgtacgc ggggaccgcg tcgatgttcc acgggtaggc    8040
ggcgatgcgc accatggaca cggggctgtc gggcaggtcg tccatggccg agaccgggca    8100
cacggtgggg acgaccatca ccgccagctc ggcgtgcgag acgtccggca cgccgcgag    8160 gtactcgggc gagcagttcg ccgagggggcc cgcggtggcg ccggcccggc ttccggaccc    8220
gccgcggtag ccgacctcga tgacgtcgac gcggcggcg tccagggtgc tcacgatggt    8280
gcggacgtcg gtggcggtga actgccagtc gttctggttc ccgccgtcgc gcagggtgca    8340
gtcgagcagg gtgggtttca cacggctcct tccagatgcg gctgcggaac gccgagccgg    8400
gtgcggaagc gttcgaccag ctgctggggc gtctggcgca cccgctgtcc ggcggggtgg    8460
ctgcgcggcc cgcagcggat ccgcaccagg cggggggtgc cggtcaggtc cagggcggcc    8520
agttcgtcga ggtcgtccac ggtgtgggcg gcggcgtagc cggccgcgag ggccgtggcc    8580
gccgggtcgc cgagggcgac ggtcgcctgc ccgccgtgc tctcgtgggc gccgttgtcg    8640
aggacggcgt ggaccaggtt cggccggtgc tcggcgatca tcggcagaca gcccgggttc    8700
atggcgaacg agccgtcgcc gtccagcacg agcacccggc ggccggggtg ggccagggcg    8760
atgccgagcc cgatcggcgc ggccatgccc atggaaccga cgagatagaa gtgctcggcg    8820
cggtcgcgga ggttgtacag gtcgcgtgtg atgaagccgc aggtgctcac cgtcagggcg    8880
tcgggctcgc ggtccagcag tgcggcgagg gcgtcacgga tgtccagcaa cgctcagatc    8940
ccttcccgga cgatgagtac ggcggtgctc cggccggagt cgtactgctt gaggaaggcc    9000
tccacgccgt cctcggggcg cgcgttgtcc agcacggtcc agggaatccc gaacacgtcg    9060
agcagccggg tgagttcgcg gccgatgacg tcgtgctcga cggcgtcgtt cccgtcgtga    9120
ccgcgccagc tgacgacgat cggcaggtgg acgtcgtaga tgaggttgaa cgaggtgagg    9180
acgttgagcg agtagccgag gccggagttc tgcatgaggg ccacgggccg ggcgccggca    9240
agggcgagac cggaggccac ccccagggcg ctgtcctcac ggggcgcggg gatgtaggcg    9300
gcggggcagc cggggtcctc cagtaatcgg aagagcccctt tcagcagtga gcacggtacg    9360
ccggtgaagt gggaatgacc acgttttacc aaggcattga gaacggtttc cgcgaccttg    9420
gaaccggatc ccgctgccga tgaagattca ggcagcacgc attgcccttc ttttgcgaag    9480
cgcggacagg gtcacgtccg gcgaggggcg tcttccggcc cctcggcggt gtggatcttg    9540
catgacgacc acgagaatgc gcaatgacat tccggaatac ggacaggtcg atttcccgga    9600
ccgggcctcg cgttcatcgc attcggcggc cgggcggtcc agtgccgaat cggtcgattc    9660
cgtccgcggt ttgaccgaat gtcgatgttt gaaacgagga attacgggag cgcgcttctt    9720
cggcgcgtcc gtctcccggt ggtgcggccc gtcgaggct ccgccggagg gcgggatccg    9780
ggtgcgggtg atcgccgcgc accgctccga cctgggatgt ggagggcggg aggtccgtcg    9840
ggagccgcgg cggagcgggg cgaccgcgat ccggacgcga cccggacggc tcgggcgccg    9900
tcgcgtccgt cgagagcgtt ccggtcattc ggtgagccgc gcgacggccg gtgaggccgg    9960
aaagcggtgc ccgggggggat ggaattcgag tcagatcgac ggcggggttc cggttgcctc   10020
ggcgctcgta ccaggccacg ccggacccag ggatctatgg gggcaagcag ggcggcgtgc   10080
```

```
ccggagttcc tgcggattcg gcggcgtcgc gcacgggccg tggagtgcgg cggccgggga    10140
aaaggcagga tgcagagtgg ccgaattgta gtgggtcgat gttgatcttc cccgtgtaca    10200
gtcggcgaca ttgacgtatg gcagccctcg gtaatcggga cgggaatcga gggcgccgag    10260
cgtcgaggga tgcgttcggc ttttccggcg catggccccg cacagcgtcg tgcatgggtg    10320
ccgcccctcg cccctttcca gcgtctctct ttcctcttct ttccggttct tttcgacatg    10380
caacggggtt gattcatgcg tgcggcgaaa caagacagtg atatcggcgt cgtcgacgac    10440
gaggcacaag ccgcggtcgt ggcggccgag gagatcatcg acgaggcgtc gggggggtgac   10500 ggcggtgtct tcggccacgc ctggtcggac gaccgggtgg cccacctgct ggagcgactc    10560
gcctcggact tcgtgctcga caacacctac cgcgagcagc acctgagcct caccgccagc    10620
gagaactacc cgagcaagct ggtccgcatg ctcggcagcg gactccaggg cggcttctac    10680
gagttcgccc cgccgtaccc ggccgaggcg ggcgagtggg ccttccccga ctccggcgcg    10740
aacgcgtccc tggtggggaa gctgaccggc atcggccgcc agctcttcga ggcggccacc    10800
ttcgactggc ggcccaacgg cggctcggtc gccgaacagg ccgtgctcct gggcacctgc    10860
ggacggggcg acggcttcgt gcacttcgcc cacaaggacg gcggccactt cgccctggag    10920
tcgctggccg ccgcggccgg catcaacacc taccacctgc cgatggtcga ccggaccctg    10980
ctcatcgacg tggaccggct                                                 11000
```

<210> SEQ ID NO 15
<211> LENGTH: 174
<212> TYPE: PRT
<213> ORGANISM: Streptomyces plumbeus

<400> SEQUENCE: 15

```
Val Leu Pro Glu Ser Ser Ala Ala Gly Ser Gly Ser Lys Val Ala
1               5                   10                  15

Glu Thr Val Leu Asn Ala Leu Val Lys Arg Gly His Ser His Phe Thr
            20                  25                  30

Gly Val Pro Cys Ser Leu Leu Lys Gly Leu Phe Arg Leu Leu Glu Asp
        35                  40                  45

Pro Gly Cys Pro Ala Ala Tyr Ile Pro Ala Pro Arg Glu Asp Ser Ala
    50                  55                  60

Leu Gly Val Ala Ser Gly Leu Ala Leu Ala Gly Ala Arg Pro Val Ala
65                  70                  75                  80

Leu Met Gln Asn Ser Gly Leu Gly Tyr Ser Leu Asn Val Leu Thr Ser
                85                  90                  95

Phe Asn Leu Ile Tyr Asp Val His Leu Pro Ile Val Val Ser Trp Arg
            100                 105                 110

Gly His Asp Gly Asn Asp Ala Val Glu His Asp Val Ile Gly Arg Glu
        115                 120                 125

Leu Thr Arg Leu Leu Asp Val Phe Gly Ile Pro Trp Thr Val Leu Asp
    130                 135                 140

Asn Ala Arg Pro Glu Asp Gly Val Glu Ala Phe Leu Lys Gln Tyr Asp
145                 150                 155                 160

Ser Gly Arg Ser Thr Ala Val Leu Ile Val Arg Glu Gly Ile
                165                 170
```

<210> SEQ ID NO 16
<211> LENGTH: 190
<212> TYPE: PRT
<213> ORGANISM: Streptomyces plumbeus

```
<400> SEQUENCE: 16

Leu Leu Asp Ile Arg Asp Ala Leu Ala Ala Leu Leu Asp Arg Glu Pro
1               5                   10                  15

Asp Ala Leu Thr Val Ser Thr Cys Gly Phe Ile Thr Arg Asp Leu Tyr
                20                  25                  30

Asn Leu Arg Asp Arg Ala Glu His Phe Tyr Leu Val Gly Ser Met Gly
            35                  40                  45

Met Ala Ala Pro Ile Gly Leu Gly Ile Ala Leu Ala His Pro Gly Arg
        50                  55                  60

Arg Val Leu Val Leu Asp Gly Asp Gly Ser Phe Ala Met Asn Pro Gly
65                  70                  75                  80

Cys Leu Pro Met Ile Ala Glu His Arg Pro Asn Leu Val His Ala Val
                85                  90                  95

Leu Asp Asn Gly Ala His Glu Ser Thr Gly Gly Gln Arg Thr Val Ala
            100                 105                 110

Leu Gly Asp Pro Ala Ala Thr Ala Leu Ala Ala Gly Tyr Ala Ala Ala
        115                 120                 125

His Thr Val Asp Asp Leu Asp Glu Leu Ala Ala Leu Asp Leu Thr Gly
130                 135                 140

Thr Pro Ala Leu Val Arg Ile Arg Cys Ala Pro Arg Ser His Pro Ala
145                 150                 155                 160

Gly Gln Arg Val Arg Gln Thr Pro Gln Gln Leu Val Glu Arg Phe Arg
                165                 170                 175

Thr Arg Leu Gly Val Pro Gln Pro His Leu Glu Gly Ala Val
            180                 185                 190

<210> SEQ ID NO 17
<211> LENGTH: 344
<212> TYPE: PRT
<213> ORGANISM: Streptomyces plumbeus

<400> SEQUENCE: 17

Val Lys Pro Thr Leu Leu Asp Cys Thr Leu Arg Asp Gly Gly Asn Gln
1               5                   10                  15

Asn Asp Trp Gln Phe Thr Ala Thr Asp Val Arg Thr Ile Val Ser Thr
                20                  25                  30

Leu Asp Ala Ala Arg Val Asp Val Ile Glu Val Gly Tyr Arg Gly Gly
            35                  40                  45

Ser Gly Ser Arg Ala Gly Ala Thr Ala Gly Pro Ser Ala Asn Cys Ser
        50                  55                  60

Pro Glu Tyr Leu Ala Ala Leu Pro Asp Val Ser His Ala Glu Leu Ala
65                  70                  75                  80

Val Met Val Val Pro Thr Val Cys Pro Val Ser Ala Met Asp Asp Leu
                85                  90                  95

Pro Asp Ser Pro Val Ser Met Arg Ile Ala Ala Tyr Pro Trp Asn
            100                 105                 110

Ile Asp Ala Val Pro Ala Tyr Val Arg Ala Val Arg Ala Leu Gly Leu
        115                 120                 125

Lys Ala Gly Val Asn Leu Met Ala Val Ser Tyr Thr Thr Glu Glu Gln
130                 135                 140

Leu Ala Glu Val Ala Ala Val Ala Ser Glu Arg Pro Asp Val Phe
145                 150                 155                 160

Tyr Ile Ala Asp Ser Phe Gly Ala Leu Thr Pro Asp Asp Val Arg Arg
                165                 170                 175

Arg Val Gly Leu Leu Ala Glu Arg Leu Pro Val Pro Leu Gly Ile His
```

```
                    180                 185                 190
Ala His Asn Asn Leu Gly Leu Ala Ala Asn Ala Leu Ala Gly Leu
            195                 200                 205

Asp Ala Gly Val Ser Trp Leu Asp Ala Ser Leu Cys Ala Met Ala Arg
        210                 215                 220

Gly Ala Gly Asn Leu Ala Thr Glu Gln Ala Ala Phe Leu Thr Ala
225                 230                 235                 240

Trp Ala Arg Tyr Asp Thr His Val Asp Leu Pro Leu Val Cys Glu Ala
                245                 250                 255

Ala Glu Tyr Val Ala Glu Gln Val Leu Pro Arg Pro Met Thr Val Arg
            260                 265                 270

Arg Ala Glu Ile Ala Ala Gly Ile Asn Asp His His Phe Tyr Phe Gln
        275                 280                 285

Asp Arg Ile Glu Lys Ile Ser Ala Arg His Gly Leu Asp Pro Trp Ala
        290                 295                 300

Val Gly His Arg Ile Gly Ala Ala Arg Pro Arg Lys Val Leu Asp Glu
305                 310                 315                 320

Thr Val Glu Asp Val Cys Arg Glu Leu Ala Gly Arg Thr Ala Gly Thr
                325                 330                 335

Glu His Thr Thr Gly Gly Asn Ala
            340

<210> SEQ ID NO 18
<211> LENGTH: 311
<212> TYPE: PRT
<213> ORGANISM: Streptomyces plumbeus

<400> SEQUENCE: 18

Met Thr Ala Ser Arg Pro Pro Gln Gln Asp Arg Asn Asp Pro Pro Asp
1               5                   10                  15

Gly Ala Ala Arg Arg Leu Arg Ala Ala Leu Ala Ala Pro Arg Leu Thr
            20                  25                  30

Arg Ala Met Gly Ala His Ser Pro Leu Ser Ala Arg Leu Ala Glu Glu
        35                  40                  45

Ala Gly Phe Asp Val Val Trp Ser Ser Gly Leu Glu Ile Ser Ala Ala
    50                  55                  60

Ala Gly Val Pro Asp Ala Asn Ile Leu Ser Met Gly Glu Cys Leu Asp
65                  70                  75                  80

Ala Ala Ala Gly Leu Ala Ser Ser Val Asp Leu Pro Val Leu Ala Asp
                85                  90                  95

Cys Asp Ser Gly Phe Gly Asn Val Asn Asn Val Ile His Met Val Arg
            100                 105                 110

Ser Tyr Glu Ala Arg Gly Val Ala Gly Val Cys Ile Glu Asp Lys Gln
        115                 120                 125

Phe Pro Lys Leu Asn Ser Phe Val Glu Gly Asn Gln Asp Leu Ala Pro
    130                 135                 140

Leu Asp Asp Phe Ala Ala Lys Ile Arg Gly Ala Ser Glu Thr Arg Thr
145                 150                 155                 160

Asp Met Val Val Val Ala Arg Leu Glu Ala Leu Ile Ser Gly Gln Gly
                165                 170                 175

Met Ala Glu Ala Leu Arg Arg Ala Asp Val Tyr Glu Arg Ala Gly Ala
            180                 185                 190

Asp Ala Leu Leu Ile His Ser Lys Arg Lys Asp Pro Glu Glu Val Phe
        195                 200                 205

Ala Phe Arg Glu Ala Tyr Arg Gly Asp Leu Pro Val Ile Val Val Pro
```

```
                210                 215                 220
Thr Thr Tyr Asn Gln Val Thr Val Glu Glu Leu Glu Gln Arg Gly Phe
225                 230                 235                 240

Ala Met Ala Ile Tyr Ala Asn Gln Ala Leu Arg Ser Ser Ile Arg Ala
                245                 250                 255

Met Arg Glu Thr Leu Thr Arg Ile Met Arg Asp Gly Thr Thr Leu Asn
                260                 265                 270

Val Glu Pro Glu Leu Ala Pro Leu Lys Glu Ile Phe Asp Leu Gln Arg
                275                 280                 285

Met Pro Gln Met Leu Glu Gln Gln Gly Arg Tyr Glu Ser Leu Gly Arg
                290                 295                 300

Glu Leu Ala Glu Ala Ala Gln
305                 310

<210> SEQ ID NO 19
<211> LENGTH: 371
<212> TYPE: PRT
<213> ORGANISM: Streptomyces plumbeus

<400> SEQUENCE: 19

Val Thr Thr Arg Pro Thr Ala Leu Arg Leu Asp Phe His Gly Thr Pro
1               5                   10                  15

Leu Asp Leu Glu Val Ala Pro Gly Ala Arg Leu Glu Asp Ala Leu Ala
                20                  25                  30

Phe Leu Ala Thr His Leu Thr Ala Glu Glu Ala Lys Pro Asp Glu Thr
                35                  40                  45

Gly Arg Glu Pro Val Ala Thr Leu Arg Val His Ala Gly Asp Pro Gly
        50                  55                  60

Leu Leu Ala Pro Pro Ala Gly Thr Ala Ala Glu Asp Ile His Leu Arg
65                  70                  75                  80

Lys Ser Ala Ser Glu Phe Phe Thr Val Pro Ala Arg Arg Ala Ala Val
                85                  90                  95

Asp Gly Arg Glu Tyr Leu Glu Cys Thr Lys Thr Gly Ser Arg Phe Val
                100                 105                 110

Phe Asp Arg Ala Ser Arg Val Ile Asp Val Ala Leu Gly Ala Gly Gly
                115                 120                 125

His Met Asp Leu Val Glu Leu Val Arg Asp Leu Val Leu Lys His Gln
                130                 135                 140

Glu Asn Asn Gly Ala Ala Val Leu His Ala Thr Ala Ala Tyr Arg Asp
145                 150                 155                 160

Gly Thr Val Val Leu Val Thr Gly Ala Lys Gly Ala Gly Lys Ser Thr
                165                 170                 175

Val Leu Leu Glu Leu Val Glu His Phe Gly Tyr Glu Ile Leu Ser Gly
                180                 185                 190

Asp Lys Thr Val Val His Glu Leu Pro Asp Gly Ser Val Leu Ala Ala
                195                 200                 205

Gly Trp Pro Asp Tyr Pro His Leu Gly Tyr Gly Thr Val Ala Lys Tyr
        210                 215                 220

Pro Gly Leu Arg Glu Ile Ala Gly Ile Ala Asp Asp Tyr Val Pro Ala
225                 230                 235                 240

Glu Gly His Ala Phe Ser Pro Val Gly Lys Phe Ala Val Asp Pro Leu
                245                 250                 255

Pro Phe Arg Asp Arg Phe Pro Ser Ala Pro Ala Gly Val Arg Val Pro
                260                 265                 270

Val Ala Ala Ile Leu His Pro Ser Ile Gly Pro Gly Glu His Thr Val
```

```
                    275                 280                 285
Val Glu Pro Leu Thr Gly Gly Arg Glu His Ala Glu Val Leu Arg
    290                 295                 300

Ala Asn Val Glu Ser Ala Phe Asp Gly Ala Asn Ala Gly Trp His His
305                 310                 315                 320

Tyr Leu Asp Asp Arg Ala Ala His Ala Glu Arg Val Thr Arg Ile
                325                 330                 335

Thr Asp Val Leu Ala Gly Val Pro Ala Trp Thr Leu Thr Gly Pro Gly
            340                 345                 350

Asp Leu Thr Ala Arg Asn Val Pro Ala Leu Ile Ala Gly Pro Ala Glu
                355                 360                 365

Ala Ala Leu
    370

<210> SEQ ID NO 20
<211> LENGTH: 154
<212> TYPE: PRT
<213> ORGANISM: Streptomyces plumbeus

<400> SEQUENCE: 20

Val Ile Glu Leu Thr Val His Ser Thr Gly Leu Asn Ser His Tyr Asp
1               5                   10                  15

Leu Thr Asp Thr Ile Ala Asp Ser Leu Arg Glu His Gly Ala Gly Asp
                20                  25                  30

Gly Leu Ala Gly Val Phe Ala His Gly Ser Thr Ile Gly Leu Thr Val
            35                  40                  45

Met Arg Tyr Glu Pro Gly Ala Val Gln Asp Leu Leu Arg Thr Leu Glu
    50                  55                  60

Arg Ile Ala Pro Glu Ser Pro Ala Gly Ala Gly Arg Tyr Leu His Glu
65                  70                  75                  80

Leu Thr Thr Glu Asp Pro Asn Gly Phe Ser His Leu Lys Ser Ser Leu
                85                  90                  95

Leu Gly Thr Ser Leu Leu Val Pro Phe Arg Asp Gly Ala Leu Ala Met
            100                 105                 110

Ser Pro Ser His Arg Val Val Leu Phe Asp Phe Asp Leu Lys Pro Ala
        115                 120                 125

Thr Arg Arg Val Phe Leu Asp Ala Pro Arg Thr Ala Pro Ala Pro
    130                 135                 140

His Thr Asp Thr Val Thr Glu Lys Ser Leu
145                 150

<210> SEQ ID NO 21
<211> LENGTH: 380
<212> TYPE: PRT
<213> ORGANISM: Streptomyces plumbeus

<400> SEQUENCE: 21

Val Lys Leu Arg Leu Ala Thr Pro Gly Pro Thr Glu Val Pro Gln Arg
1               5                   10                  15

Leu Leu Leu Ala Gly Ala Arg Glu Ile Ile His Arg Ser Thr Glu
            20                  25                  30

Met Glu Gln Leu Ile His Glu Ile Ser Gly Gly Leu Pro Pro Leu Phe
    35                  40                  45

Gly Thr Ala Ser Pro Val Tyr Thr Ile Ala Ser Ser Gly Thr Gly Ala
    50                  55                  60

Met Glu Ala Ala Val Ala Asn Cys Phe Ser Ala Gly Asp Glu Val Leu
65                  70                  75                  80
```

```
Val Val Ser Asn Gly Tyr Phe Gly Glu Arg Phe Gln Ala Ile Cys Ala
            85                  90                  95

Ser Tyr Gly Leu Val Val His Val Val Glu Ser Asp Trp Gly Thr Ser
            100                 105                 110

Ala Asp Pro Glu Arg Val Ala Ala Tyr Arg Glu His Pro Ala Ile
            115                 120                 125

Arg Gly Ala Phe Val Val Tyr Ser Glu Thr Ser Thr Gly Ala Leu Asn
    130                 135                 140

Asp Val Glu Ala Ile Gly Arg Ile Phe Arg Asp Thr Asp Val Ile Thr
145                 150                 155                 160

Val Val Asp Ala Ile Ser Gly Leu Leu Val His Pro Leu Glu Met Asp
                165                 170                 175

Ala Trp Gly Leu Asp Val Val Leu Ala Ala Ser His Lys Gly Phe Met
            180                 185                 190

Leu Pro Pro Gly Leu Ala Phe Val Ala Leu Ser Asp Lys Ala Trp Thr
        195                 200                 205

Ala Val Glu Arg Ser Thr Gly Pro Asn Tyr Tyr Trp Ser Phe Glu Arg
    210                 215                 220

Leu Arg His Phe Tyr Pro Met Ser Ser Ser Pro Ala Val Ser Leu
225                 230                 235                 240

Leu Leu Ala Leu His Glu Ser Leu Lys Met Leu Gly Glu Gly Thr
                245                 250                 255

Asp Ala Phe Arg Thr Arg His Ala Val Leu Gly Lys Ala Ala Glu Arg
            260                 265                 270

Gly Leu Leu Lys Leu Gly Phe Ser Thr Phe Val Gln Ala Pro His Arg
        275                 280                 285

Arg Ser His Val Ile Thr Ala Ala Leu Ala Pro Glu Gly Ile Asp Thr
    290                 295                 300

Gly Arg Leu Leu Lys Thr Leu Ser Thr Ser Tyr Gly Val Thr Met Thr
305                 310                 315                 320

Gly Gly Gln Ala His Leu Lys Gly Arg Leu Ile Arg Val Gly His Val
                325                 330                 335

Gly Ala Ala Asp Ser Leu Asp Leu Ile Gly Ile Phe Gly Ala Leu Glu
            340                 345                 350

Met Ala Leu Leu Asp Leu Gly His Thr Phe Thr Pro Gly Ser Gly Val
        355                 360                 365

Gly Glu Ile Ile Arg Thr Phe His Glu Glu Gly Arg
    370                 375                 380

<210> SEQ ID NO 22
<211> LENGTH: 101
<212> TYPE: PRT
<213> ORGANISM: Streptomyces plumbeus

<400> SEQUENCE: 22

Met Leu Val Leu Phe Gln Arg Glu Thr Cys Pro Asp Cys Lys Pro Val
1               5                   10                  15

Arg Glu Leu Leu Thr Arg Leu Gln Val Ser Tyr Ile Asn Val Asn Val
            20                  25                  30

Pro Lys Pro Arg Glu Glu Arg His Glu Leu Ile Arg Thr Thr Gly Ser
        35                  40                  45

Lys Phe Ile Pro Ala Leu Val Asp Gly Ala Thr Val Ile Pro Gly Arg
    50                  55                  60

Leu Arg Glu Asn Ala Asp Ile Ile Ala Tyr Leu Glu Lys Arg Phe Gly
65                  70                  75                  80
```

```
Asp Pro Glu Thr Val Ala Pro Ala Ala Val Ala Gly Ala Glu Ala Arg
                85                  90                  95

Pro Gly Thr Glu Ala
            100

<210> SEQ ID NO 23
<211> LENGTH: 241
<212> TYPE: PRT
<213> ORGANISM: Streptomyces plumbeus

<400> SEQUENCE: 23

Val Arg His Ala Val Val Thr Asp Val His Gly Asp Thr Ala Arg Leu
1               5                   10                  15

Arg Ala Val Leu Gly Ala Ile Arg Glu Gln Arg Val Asp Arg Val Ile
                20                  25                  30

Cys Leu Gly Asp Val Leu Glu Cys Arg Val Gly Lys Arg Glu Ala Ala
            35                  40                  45

Gly Tyr Ala Phe Gly Gly Arg Leu Thr Asp Val Phe Asp Pro Asp Pro
        50                  55                  60

Glu Leu Ala Arg Leu Leu Asp Gly Val Arg Leu Val Arg Gly Asn Gln
65                  70                  75                  80

Glu Glu Arg Ile Arg Ala Leu Val Pro Glu Ala Ala Leu Pro Gly Trp
                85                  90                  95

Thr Arg Pro Leu Leu His Ala Pro Arg Glu His Arg Thr Gly Phe Ala
                100                 105                 110

Leu Tyr Cys His Gly His Pro Leu Pro Trp Arg Glu Leu Glu Pro Gly
            115                 120                 125

Leu Trp Cys Pro Ala Asp Ala Asp Phe Pro Gly Arg Ala Leu Val His
        130                 135                 140

Gly His His Arg Ser Ala Leu Tyr Arg Leu Trp Pro Thr Arg Thr
145                 150                 155                 160

Gly Pro Val Arg Ala Glu Arg Leu Pro Val Arg Phe Gly Thr Pro Ile
                165                 170                 175

Pro Leu Ala Pro Asp Gly Arg Tyr Val Val Asn Val Gly Ser Val Ala
                180                 185                 190

Pro Cys Ala Pro Asp Arg Gly Pro Ser Pro Ala Trp Ala Val Val Asp
            195                 200                 205

Glu Ala Ala Ser Thr Val Thr Tyr His His Ala Pro His Pro Thr Ala
        210                 215                 220

Pro Arg Pro Leu Asp Pro Arg Pro Thr Ala Pro Arg Pro Thr Glu Lys
225                 230                 235                 240

Gln

<210> SEQ ID NO 24
<211> LENGTH: 394
<212> TYPE: PRT
<213> ORGANISM: Streptomyces plumbeus

<400> SEQUENCE: 24

Val Pro Ala Thr Leu Arg Ile Ala Val Ala Gly Thr Pro Gln Leu
1               5                   10                  15

Val Arg Pro Ala Arg Ala Leu Gly Ile Gly Thr Val Leu Val His Asp
                20                  25                  30

Arg Ala Arg Pro Ala Pro Ala Val Ala Ala Glu Ala Gly Thr Ala Val
            35                  40                  45

Ala Val Asp Leu Ala Asp Thr Asp Ala Leu His Ala Ala Leu Ala Pro
```

```
            50                  55                  60
Leu His Ala Ala His Pro Phe Gly Arg Val Leu Ser Leu Thr Glu Ser
 65                  70                  75                  80

Gly Leu Leu Pro Ala Ala Val Ala Gly Arg Leu Gly Leu Pro Gly
                 85                  90                  95

Asn Ser Leu Arg Thr Val Asp Leu Leu Gln Asp Lys Arg Arg Met Arg
                100                 105                 110

Glu Val Leu Asn Ala Arg Gly Ile Gly Pro Val Arg Thr Thr Ala Pro
                115                 120                 125

Arg Asp Ala Val Gly Leu Ala Ala Phe Cys Arg Ala Ala Gly Gly Pro
130                 135                 140

Val Val Leu Lys Pro Ala Ala Gly Thr Ala Ser Gln Ala Val Phe Glu
145                 150                 155                 160

Val Ala Gly Pro Ala Glu Ala Glu Ala Val Trp Arg Ala Phe Glu Ala
                165                 170                 175

Ala Gly Gly Ala Gly Pro Ile Ala Glu Glu Tyr Leu Asp Gly Pro Glu
                180                 185                 190

Ile Ser Val Glu Ser Phe Ser His Asp Gly Arg His Thr Val Leu Ala
                195                 200                 205

Val Thr Asp Lys Leu Thr Gly Pro Ala Phe Val Glu Thr Gly His Thr
210                 215                 220

Leu Pro Ser Cys Leu Pro Ala Pro Val Leu Ser Glu Val Thr Ala Leu
225                 230                 235                 240

Val Val Ala Phe Leu Asp Ala Val Gly Leu Thr Glu Gly Pro Ala His
                245                 250                 255

Thr Glu Val Lys Val Thr Ala Lys Gly Pro Arg Ile Leu Glu Ser His
                260                 265                 270

Asn Arg Ile Gly Gly Asp Lys Ile Arg Glu Leu Leu Arg Arg Ala Tyr
                275                 280                 285

Gly Leu Asp Leu Val Ala Leu Thr Ala Gly Cys Pro Phe Gly Leu Leu
                290                 295                 300

Pro Pro Pro Gly Ala Pro Pro Ala Ala Arg Arg Gly Ala Ala Ile Arg
305                 310                 315                 320

Phe Leu Thr Pro Pro Pro Gly Thr Val Arg Glu Ile Ala Leu Pro Asp
                325                 330                 335

Thr Gly Gly Thr Thr Ala Glu Ile Arg Leu Asp Val Thr Val Gly Asp
                340                 345                 350

Pro Val Arg Pro Val Arg Arg Ser Gln Asp Arg Ala Gly Tyr Val Ile
                355                 360                 365

Ala Asp Gly Thr Asp Ala Ala Asp Ala Ala Arg Val Cys Glu Ala Leu
370                 375                 380

Ala Gly Arg Val Arg Ile Glu Thr Ser Gly
385                 390

<210> SEQ ID NO 25
<211> LENGTH: 385
<212> TYPE: PRT
<213> ORGANISM: Streptomyces plumbeus

<400> SEQUENCE: 25

Val Thr Arg Gln Val Leu Leu Leu Asn Ser Asp Lys Pro Glu Val Leu
 1               5                  10                  15

His Ala Leu Ala Arg Arg Pro Gly Val Thr Val Arg Val Ile Thr Arg
                20                  25                  30

Pro Val Tyr Ala Gly Leu Tyr Glu Asn His Glu Thr Ala Tyr Val Asp
```

-continued

```
             35                  40                  45
Ser Phe Ala Asp Leu Thr Gln Val Glu Arg Ala Ala Tyr Glu Ile Ala
 50                  55                  60

Ala His Gly Pro Val Asp His Val Ile Ala Ala Thr Glu Lys Ser Val
 65                  70                  75                  80

Val Ala Ala Gly Leu Val Arg Ala Leu Leu Gly Val Pro Gly Pro Gly
                 85                  90                  95

Phe Asp Gln Ser Leu Arg Gly Ala His Lys Arg Ala Met Lys Asp Arg
                100                 105                 110

Leu Arg Ala Ala Gly Ile Pro Val Thr Asp Tyr Ala Gln Ala Ala Thr
                115                 120                 125

Leu Asp Ala Val Pro Ala Ala Ala Glu Arg Thr Gly Trp Pro Val Met
                130                 135                 140

Ile Lys Pro Val Phe Gly Ala Ala Ser Lys Cys Thr His Arg Val Asp
145                 150                 155                 160

Ser Pro Gly Glu Phe Ala Arg Arg His Arg Ala Gly Asp Phe Ala Asp
                165                 170                 175

Leu Ala Asp Thr Arg Leu Pro Val Gln Val Glu Arg Leu Val Arg Phe
                180                 185                 190

Thr His Glu Tyr His Cys Asp Gly Val Val His Gly Gly Glu Val Ala
                195                 200                 205

Arg Ala Ala Val Ser Arg Tyr Phe Leu Pro Pro Leu His Thr Ser Pro
210                 215                 220

Asp Leu Asn Ser Gly Tyr Leu Ala Asp Gln Ser Asp Ala Phe Ser Arg
225                 230                 235                 240

Glu Val Leu Asp Leu His Arg Arg Val Ala Thr Leu Gly Leu Pro
                245                 250                 255

Ala Gly Val Thr His Leu Glu Val Phe Arg Thr Glu Asp Gly Pro Val
                260                 265                 270

Val Gly Glu Val Ala Val Arg Pro Gly Gly Met Gly Ile Ser Arg Met
                275                 280                 285

Trp Trp His Ala Phe Gly Val Asp Leu Trp Glu Glu Phe Val Arg Val
                290                 295                 300

Ser Ala Gly Glu Arg Pro Gly Arg Pro Ala Arg Glu Pro Arg Ala Gly
305                 310                 315                 320

Thr Val Gly Arg Ser Arg Leu Pro Ala Leu Pro Gly Leu Arg Ala Arg
                325                 330                 335

Val Leu Ala Leu Pro Gly Val Leu Glu Val Leu Thr Pro Glu Glu Cys
                340                 345                 350

Ala Ser Pro Gly Arg Leu Glu Ala Tyr Phe Ala Ala Glu Asp Glu Pro
                355                 360                 365

Ala Ala Glu Arg Phe Ile Ala Arg Leu His Thr Met Ala Gly His Gly
                370                 375                 380

Ala
385
```

COMPOSITIONS AND METHODS FOR THE SYNTHESIS OF APPA-CONTAINING PEPTIDES

CROSS-REFERENCE TO RELATED APPLICATIONS

The present application is U.S. Non-provisional Patent Application which claims priority to U.S. Provisional Patent Application Ser. No. 61/296,993, filed Jan. 21, 2010, which is incorporated herein by reference.

STATEMENT REGARDING FEDERALLY SPONSORED RESEARCH AND DEVELOPMENT

Part of the work during the development of this present disclosure was made with government support from the National Institutes of Health under grant number GM PO1 GM077596. The U.S. Government has certain rights in the present disclosure.

REFERENCE TO A "SEQUENCE LISTING"

A "Sequence Listing" is provided herewith through submission via EFS-Web. The Sequence Listing submitted via EFS-Web contains one file named "SequenceListingP01961US01.txt". The file was created on Jan. 21, 2010, and is 116,487 bytes in size. The contents of the Sequence Listing are hereby incorporated by reference in its entirety.

BACKGROUND

Rhizocticins are phosphonate-containing oligopeptide antibiotics produced by the Gram-positive bacterium *B. subtilis* ATCC6633. They were originally discovered in 1949 based on their antifungal activity and collectively termed "rhizoctonia factor" (Michener and Snell, Arch. Biochem. 22, 208-214, 1949). The structures of rhizocticins were determined 40 years later (Rapp et al., Liebigs Ann. Chem., 655-661, 1988). They are dipeptide and tripeptide antibiotics consisting of a variable amino acid at the N-terminus followed by arginine and the non-proteinogenic amino acid (Z)-L-2-amino-5-phosphono-3-pentenoic acid ("APPA", FIG. 1A). Interestingly, APPA is also the C-terminal amino acid of the tripeptide antibiotics plumbemycin A and B produced by *Streptomyces plumbeus* (FIG. 1B) (Park et al., Agric. Biol. Chem. 41, 573-579, 1977; Park et al., Agric. Biol. Chem. 41, 161-167, 1977). Plumbemycin A and B are tripeptides consisting of N-terminal alanine followed by aspartate (A) or asparagine (B) and the C-terminal non-proteinogenic amino acid APPA.

Rhizocticins enter the target fungal cell through the oligopeptide transport system. They are then cleaved by host peptidases to release APPA, which inhibits threonine synthase, an enzyme catalyzing the pyridoxal 5'-phosphate (PLP)-dependent conversion of phosphohomoserine to L-threonine (FIG. 1C). Hence, APPA interferes with the biosynthesis of threonine and related metabolic pathways, ultimately affecting protein synthesis and leading to growth inhibition. The inhibitory activity of APPA is due to the structural resemblance to phosphohomoserine, but possessing a hydrolytically stable C—P bond in place of the C—O—P moiety of phosphohomoserine.

Whereas rhizocticins exhibit antifungal activity, plumbemycins are antibacterials. It has been demonstrated that plumbemycins enter *Escherichia coli* K-12 via the oligopeptide transport system (Diddens, et al., J. Antibiot. 32, 87-90, 1979). As in the case of rhizocticins, L-threonine reverses the growth inhibition by plumbemycins in a concentration-dependent manner. Furthermore, similarly to rhizocticins, plumbemycins must be cleaved by peptidases of the target cell to release the active substance, APPA. The selectivity of these tripeptide antibiotics is thus not due to a difference in mode of action, but rather determined by the recognition of proteinogenic amino acids attached at the N-terminus of APPA by a specific oligopeptide transport system and/or peptidase. Furthermore, the target of APPA, threonine synthase, is not present in mammals, reducing the likelihood of toxicity to humans.

Due to the prevalence of infectious agents, and their effect on humans, there exists a need for anti-fungal and anti-bacterial agents, such as rhizocticin and plumbemycin. Unfortunately, the synthesis of APPA, as well as APPA-containing peptides, is a very challenging endeavor which makes it commercially impractical. Because of this limitation, and the inability to produce modified APPA-containing peptides from their native bacteria, these peptides are not presently a viable commercial option.

BRIEF SUMMARY

According to at least one embodiment of an isolated nucleic acid of the present disclosure, the isolated nucleic acid comprises a first nucleotide sequence encoding a first polypeptide having a first sequence identity of at least about 70 percent to an amino acid sequence selected from the group consisting of SEQ ID NOS: 2-13 and 15-23. The first sequence identity of an embodiment of the isolated nucleic acid may further be selected from the group consisting of at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%

Additionally, in at least one embodiment of the isolated nucleic acid the first sequence identity is at least about 70 percent to SEQ ID NO: 7. The isolated nucleic acid may further comprise a second nucleotide sequence encoding a second polypeptide having a second sequence identity of 70 percent or greater to SEQ ID NO: 8, and optionally a third nucleotide sequence encoding a third polypeptide having a third sequence identity of at least about 70 percent to a third amino acid selected from the group consisting of SEQ ID NOS: 2-6, 9-13 and 15-23.

In at least one embodiment of a vector of the present disclosure, a vector comprises an isolated nucleic acid that comprises a nucleotide sequence encoding a first polypeptide having a first sequence identity of 70 percent or greater to an amino acid sequence selected from the group consisting of SEQ ID NOS: 2-13 and 15-23. At least one embodiment of the vector may be capable of integration into a host cell genome. Further, the vector may be selected from a group consisting of a bacterial vector, a mammalian vector, an insect vector, and a yeast vector.

According to at least one embodiment of a transformed cell of the present disclosure, the transformed cell comprises a vector comprising an isolated nucleic acid having a nucleotide sequence encoding a first polypeptide having a first sequence identity of 70 percent or greater to an amino acid sequence selected from the group consisting of SEQ ID NOS: 2-13 and 15-23, and wherein the transformed cell is capable of producing an APPA-containing peptide. The APPA-containing peptide may in at least one embodiment be a rhizocticin, such as rhizocticin B, or a plumbemycin, such as plumbemycin A.

In at least one embodiment of a transformed cell of the present disclosure, the transformed cell is selected from a group consisting of a Gram negative organism, a Gram positive organism, a mammalian cell, an insect cell, and a yeast cell. Further, the transformed cell may be a member of the genus *Bacillus*, or *Streptomyces*.

According to at least one embodiment of a method of the present disclosure, a method is disclosed for producing an APPA-containing peptide, such as a rhizocticin or a plumbemycin. In at least one embodiment, the method comprises the steps of transforming a host cell with an isolated nucleic acid, where the isolated nucleic acid comprises a nucleotide sequence encoding a polypeptide having a sequence identity of 70 percent or greater to an amino acid sequence selected from the group consisting of SEQ ID NOS: 2-13, and 15-25. Additionally, the method for producing an APPA-containing peptide may further comprises the step of growing the transformed host cell under conditions to produce an APPA-containing peptide. Optionally, an embodiment of the method may further comprise the step of isolating the APPA-containing peptide from the transformed host cell or supernatant from the transformed cell. Moreover, an embodiment of the method for producing an APPA-containing peptide may further comprise the step of replacing at least one amino acid from the isolated APPA-containing peptide. In at least one embodiment, the untransformed host cell is not capable of producing an APPA-containing peptide.

DETAILED DESCRIPTION

The disclosure of the present application provides various compositions and methods for the production of (Z)-L-2-amino-5-phosphono-3-pentenoic acid ("APPA")-containing peptides, such as Rhizocticins and Plumbemycins. Specifically, gene operons enabling the production of APPA-containing peptides have been identified and are described herein. Additionally, methods are disclosed herein for the production of APPA-containing peptides through in vivo systems.

The ability to biosynthetically prepare APPA-containing peptides provides an avenue to not only produce known APPA-containing peptides at useful quantities, but also allows for modifying the N-terminal amino acids of APPA-containing peptides using known techniques to create analogs with desired specificity.

A. Identification of the Rhizocticin Gene Operon

The operon responsible for the production of rhizocticin, which had not been previously identified, is shown herein. To identify the operon responsible for production of rhizocticin, the genome of a strain of a rhizocticin-producing *B. subtilis* (*B. subtilis* ATCC6633) was sequenced using a 454 sequencing platform. Briefly, sequencing data was assembled into 37 contigs spanning approximately 4.0 MB. A total of 3769 open reading frames (ORFs) were determined and annotated using the RAST Server (Rapid Annotations using Subsystems Technology). For comparison, the closely related *B. subtilis* 168 strain has a genome of 4.2 Mb comprised of 4114 coding sequences.

Figure 1:
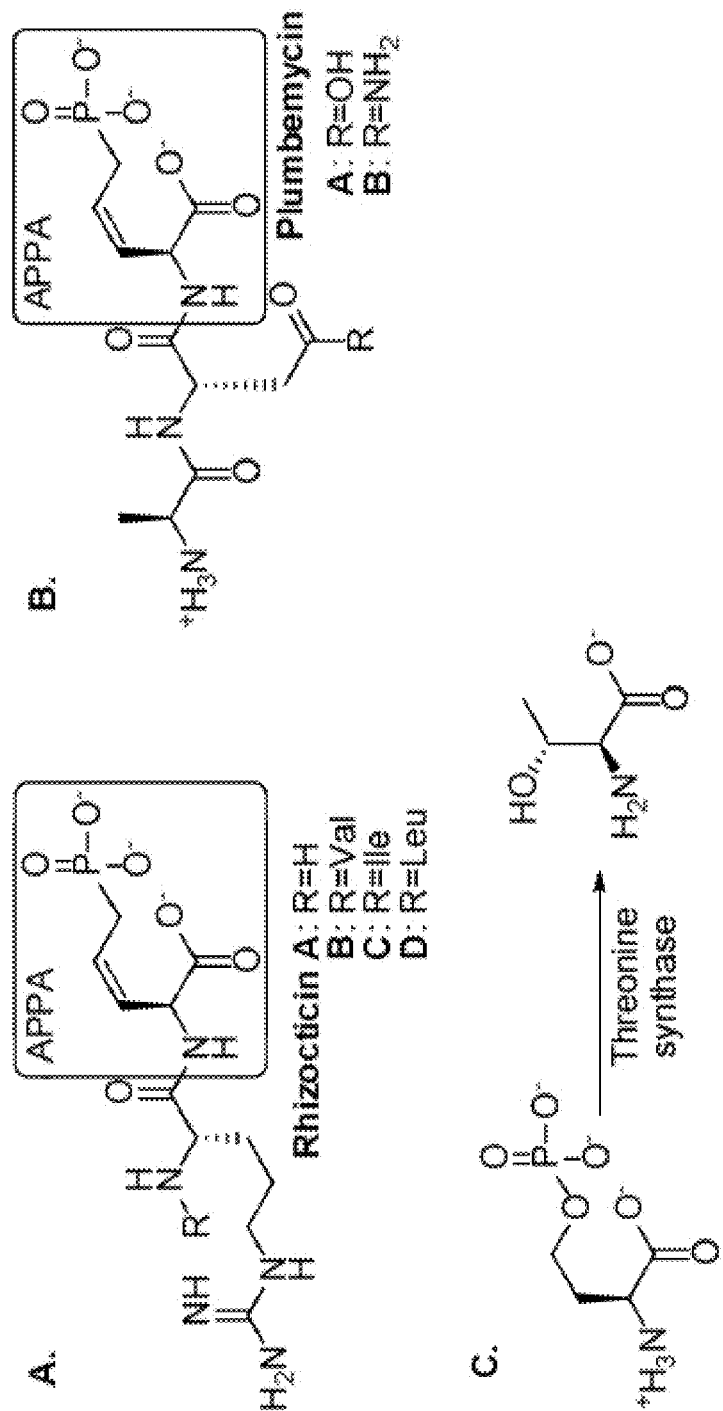
FIG. 1 shows the chemical structures of the phosphonate antibiotics rhizocticins (A) and plumbemycins (B), and the threonine synthase reaction inhibited by APPA (C)
Figure 2:
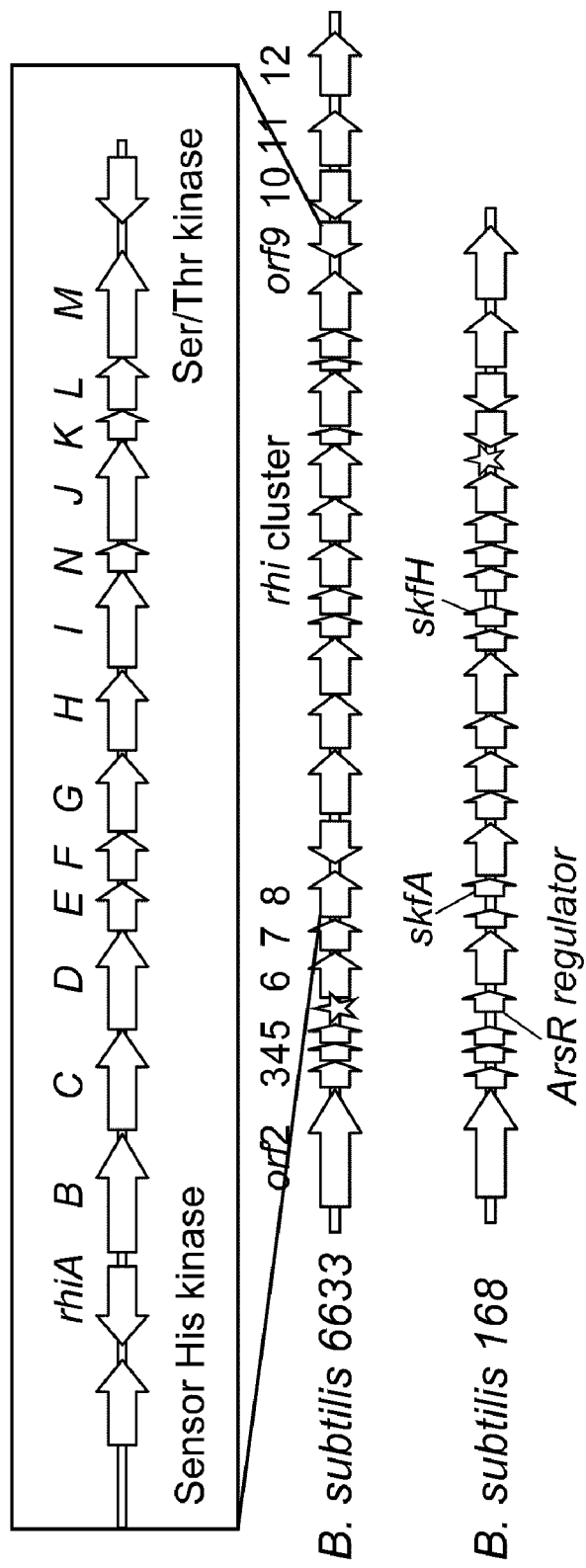
FIG. 2 shows the structural organization of the rhizocticin gene cluster and surrounding genes on the *B. subtilis* ATCC6633 chromosome.

Since the first step in the biosynthetic pathways of the majority of phosphonates is the isomerization of phosphoenolpyruvate (PEP) to phosphonopyruvate (PnPy) catalyzed by phosphoenolpyruvate phosphomutase (PEP mutase), a strategy was used to identify a gene encoding PEP mutase in a bacteria which naturally produces rhizocticin (*B. subtilis* ATCC6633). From this strategy, a sequence matching PEP mutase was identified in a part of an operon consisting of thirteen ORFs and is preceded by a differentially transcribed additional ORF encoding a transcriptional regulator (See FIG. 2). Analysis of the ORFs comprising this operon led to the conclusion that these genes constitute a rhizocticin biosynthetic gene cluster. In FIG. 2, the same locus of the *B. subtilis* 168 genome is also shown for comparison. The corresponding location of these loci in the other genome is denoted with a star.

The genes of the rhizocticin biosynthetic cluster were first annotated using the RAST Server and further analyzed with the Basic Local Alignment Search Tool (BLAST) program at NCBI and the Phyre server. The gene annotations, along with the closest and functionally confirmed homologs are shown in Table 1.

TABLE 1

Summary of the open reading frames of the rhizocticin gene cluster

| ORF | No. of aa[a] | Protein homology (NCBI No.) | % aa identity[b] |
|---|---|---|---|
| orf6 | 325 | *B. subtilis* 168 putative hydrolase/transferase (CAB1 1993) (325 aa) | 94 |
| orf7 | 223 | *B. subtilis* 168 two-component response regulator YbdJ (BAA33098) (223 aa) | 95 |
| orf8 | 322 | *B. subtilis* 168 sensor histidine kinase YbdK (BAA33099) (320 aa) | 87 |
| rhiA | 296 | *B. licheniformis* transcriptional activator of the cysJI operon (AAU21 843) (298 aa) | 65 |
|  |  | *Salmonella enterica Typhimurium* transcriptional regulator CysB (NP_460672) (324 aa) | 18 |
| rhiB | 433 | *Sphaerobacter thermophilus* threonine synthase (ZP_04494878) (420 aa) | 46 |
|  |  | *Mycobacterium tuberculosis* threonine synthase (2D1F_B) (360 aa) | 28 |
|  |  | *B. subtilis* 6633 threonine synthase ThrC (this study) (352 aa) | 27 |
| rhiC | 408 | *B. licheniformis* hypothetical protein, related to NikS (YP_077482) (405 aa) | 62 |
|  |  | *Streptomyces ansochromogenes* nikkomycin biosynthesis protein SanS, D-Ala-D-Ala ligase homolog (AAK53061) (424 aa) | 30 |
| rhiD | 407 | *B. licheniformis* MFS transporter (YP_077483) (408 aa) | 68 |
| rhiE | 167 | *Sorangium cellulosum* sulfopyruvate decarboxylase α-subunit (YP_001617955) (170 aa) | 40 |
| rhiF | 186 | *S. hygroscopicus* phosphonopyruvate decarboxylase (Q54271) (401 aa) | 40 |
| rhiG | 337 | *Legionella pneumophila* 4-hydroxy-2-oxovalerate aldolase (YP_096686) (295 aa) | 34 |
|  |  | *Pseudomonas* sp. bifunctional aldolase-dehydrogenase DmpG (1NVM_A) (345 aa) | 25 |
| rhiH | 296 | *Paenibacillus larvae* putative PEP phosphomutase (ZP_02329666) (297 aa) | 56 |
|  |  | *S. viridochromogenes* PEP phosphomutase of PTT biosynthesis (AAU00071) (313 aa) | 42 |
| rhiI | 362 | *Pseudomonas syringae* hypothetical protein (BAF32889) (354 aa) | 36 |
|  |  | *Mycoplasma pneumonia* HPr kinase/phosphatase (1KNX A) (312 aa) | 14 |
| rhiN | 132 | *Chloroherpeton thalassium* protein of unknown function UPF0047 (YP_001997537) (138 | 35 |
|  |  | *E. coli* conserved hypothetical protein YjbQ (ZP 03048862) (138 aa) | 22 |
| rhiJ | 393 | *Thermotoga lettingae* aminotransferase class V (YP_001471385) (381 aa) | 42 |
|  |  | *Methanocaldococcus jannaschii* broad-specificity class V aspartate aminotransferase (NP | 38 |
| rhiK | 85 | *Natronomonas pharaonis* glutaredoxin (CAI48716) (82 aa) | 35 |
|  |  | *E. coli* glutaredoxin 3 (1FOV_A) (82 aa) | 23 |
| rhiL | 215 | *Frankia* sp. EAN1pec putative metallophosphoesterase (YP_001 510901) (243 aa) | 32 |
|  |  | *E. coli* metal-dependent phosphodiesterase YfcE (P67095) (184 aa) | 19 |
| rhiM | 413 | *B. licheniformis* hypothetical, related to NikS (YP_077482) (405 aa) | 25 |
|  |  | *S. ansochromogenes* nikkomycin biosynthesis protein SanS, D-Ala-D-Ala ligase homolog | 26 |
| orf9 | 256 | *B. subtilis* 168 putative serine/threonine protein kinase YbdM (O31435) (256 aa) | 90 |
| orf10 | 284 | *B. subtilis* 168 putative phage protein YbdN (CAB 11998) (285 aa) | 94 |
| orf11 | 394 | *B. subtilis* 168 putative phage protein YbdO (CAB 11999) (394 aa) | 89 |

[a]aa, amino acids.
[b]Percent identity and one of the closest homologs were based on NCBI searches conducted October 8th 2009. The homolog whose biochemical function was experimentally supported is shown for proteins of particular interest.

As mentioned above, the genes surrounding the putative rhizocticin gene cluster (rhiA-rhiM), (e.g., immediately adjacent orf6-8 and orf9-11) have nearly identical counterparts in *B. subtilis* 168. As shown in Example 2, rhiA-rhiM are sufficient for the production of rhizocticin. Further, the surrounding genes orf6-8 and orf9-11 are not required for rhizocticin biosynthesis.

The rhiA gene encodes a transcriptional regulator of the LysR family. The helix-turn-helix DNA-binding motif, typical of many LysR regulators, was shown by the Phyre server to be located within the N-terminal residue numbers 30-85. Further, a ligand-binding domain is also present at the C-terminus of RhiA. The rhiA gene is located upstream and in the opposite direction of the other genes in the rhi operon as commonly seen for LysR-regulated operons.

The rhiB gene encodes a threonine synthase. Interestingly, the genome of *B. subtilis* ATCC6633 contains another copy of a threonine synthase gene, thrC, located in an operon with genes involved in the biosynthesis of threonine that is present at the same site as the threonine synthase gene in the *B. subtilis* 168 genome. Unlike RhiB, ThrC is highly homologous to threonine synthases of Gram-positive bacteria (98% identical to threonine synthase of *B. subtilis* 168), suggesting that the *B. subtilis* ATCC6633 ThrC is a threonine synthase involved in primary metabolism. Distinctly, RhiB is involved in rhizocticin self-resistance by encoding a threonine synthase homolog that is not inhibited by APPA.

The translated products of rhiC and rhiM have been reported previously. Identification and substrate specificity of RhiM was reported (named RizA by the authors) (Kino et al., Biosci. Biotechnol. Biochem., 73, 901-907, 2009). RhiM (RizA) is capable of ligating L-arginine to 19 other amino acids, including a saturated analog of L-APPA, 2-amino-5-phosphonopentanoic acid. The activity of RhiC as amino acid ligase has also been reported (Kino et al., Biosci. Biotechnol. Biochem., 74, 129-134, 2010; Arai and Kino, Biosci. Biotechnol. Biochem., 74, 1572-1577, 2010).

RhiD is a transporter of the major facilitator superfamily (MFS). Between 8 and 10 transmembrane helixes are predicted by different topology prediction tools (ca.expasy.org). RhiD is responsible for the export of rhizocticins from the cell.

The genes rhiE and rhiF encode two subunits of a PnPy decarboxylase. PnPy decarboxylases catalyze the irreversible thiamin pyrophosphate (TPP)-dependent decarboxylation of PnPy to PnAA. Unlike RhiE/RhiF, PnPy decarboxylases usually consist of a single polypeptide chain. To date, RhiE/RhiF is the first example of a PnPy decarboxylase consisting of two subunits.

Figure 3:
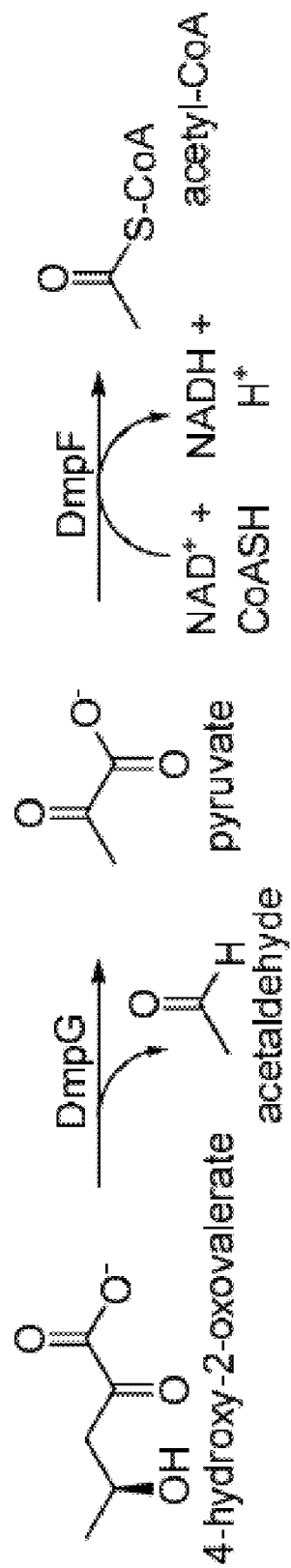
FIG. 3 shows a representation of the reaction catalyzed by the RhiG homolog 4-hydroxy-2-oxovalerate aldolase DmpG and the subsequent step catalyzed by DmpF, according to at least one embodiment of the disclosure.

A search of the NCBI database for protein sequences homologous to the translated product of rhiG yielded a number of putative 4-hydroxy-2-oxovalerate aldolases with modest homology to RhiG (identity of 35% and lower). The closest homologs of RhiG that have been biochemically characterized are the 4-hydroxy-2-oxovalerate aldolases NahM and DmpG (25% identity) of *Pseudomonas putida* strains. NahM and DmpG belong to the class II family of aldolases that are dependent on divalent metal ions for catalysis, and act to catalyze the penultimate step of the meta-cleavage pathway from catechol to pyruvate and acetyl-CoA during the catabolism of aromatic compounds by *Pseudomonas* strains. DmpG is a part of a bifunctional enzyme complex as it physically associates with the enzyme of the following step, acetaldehyde dehydrogenase (acylating) DmpF, to ensure efficient transfer of the reactive intermediate acetaldehyde (FIG. 3). As described in Section F(2), RhiG exhibits aldolase activity.

The rhiH gene encodes a PEP mutase that catalyzes the first step in the biosynthetic pathway, the conversion of PEP to PnPy.

The translated product of rhiI has no significant end-to-end homology to any of the entries in the NCBI database. However, the C-terminus of RhiI (approximately 213 amino acids) shows low homology to the C-terminal domain of the histidine containing phospho carrier protein (HPr) kinase/phosphorylase from several species. In low GC Gram-positive bacteria, HPr is involved in the regulation of carbon catabolism. HPr kinase/phosphorylase is a bi-functional protein that modifies Ser-46 of HPr and accepts ATP or pyrophosphate ($PP_i$) as a phosphate group donor. RhiI contains an identifiable canonical nucleotide binding P-loop (GSKGKGKS). Additionally, RhiI catalyzes an ATP-dependent phosphorylation of a small molecule or plays a regulatory role similar to HPr kinase/phosphorylase.

The translated gene product of rhiN shows homology to a number of hypothetical proteins belonging to an uncharacterized protein family UPF0047 (ExPASy, Prosite). Presently, no biological activity has been established for RhiN.

The gene rhiJ encodes an aminotransferase belonging to a family of Fold Type I PLP-dependent enzymes. It can be further classified into phylogenetic class V of aminotransferases (also referred to as subgroup IV).

BLAST analysis revealed that RhiK is a homolog of glutaredoxins, small proteins related to thioredoxins and involved in the maintenance of the reducing environment of the cytoplasm. RhiK contains a CPYC motif conserved among glutaredoxins and is predicted to have a typical $\beta\alpha\beta\alpha\beta\beta\alpha$ thioredoxin fold. RhiK also shows homology to the N-terminal domain of glutathione S-transferase, another member of the thioredoxin-like superfamily.

The translated sequence of rhiL belongs to the calcineurin-like superfamily (PF00149) that includes metal-dependent phosphomonoesterases and phosphodiesterases catalyzing the hydrolysis of diverse substrates, from phosphorylated proteins to nucleic acids. Several conserved amino acid residues are present in RhiL, most notably all those comprising the binuclear metal center, indicating that it has a phosphodiesterase activity.

B. Identification of the Plumbemycin Gene Operon

In order to identify the gene cluster responsible for the biosynthesis of plumbemycin, a fosmid library of *S. plumbeus* genomic DNA was screened for the homologs of PEP mutase using degenerate primers. One fosmid was identified and sequenced using transposon insertions. Three additional fosmids, overlapping with the first one, were identified by PCR using primers specific to the insert of the first fosmid, and one of these overlapping fosmids was sequenced as well. The data was assembled into a 62,534 bp-long fragment of *S. plumbeus* genomic DNA sequence which was annotated using the RAST Server and the BLAST program at NCBI.

Figure 4:
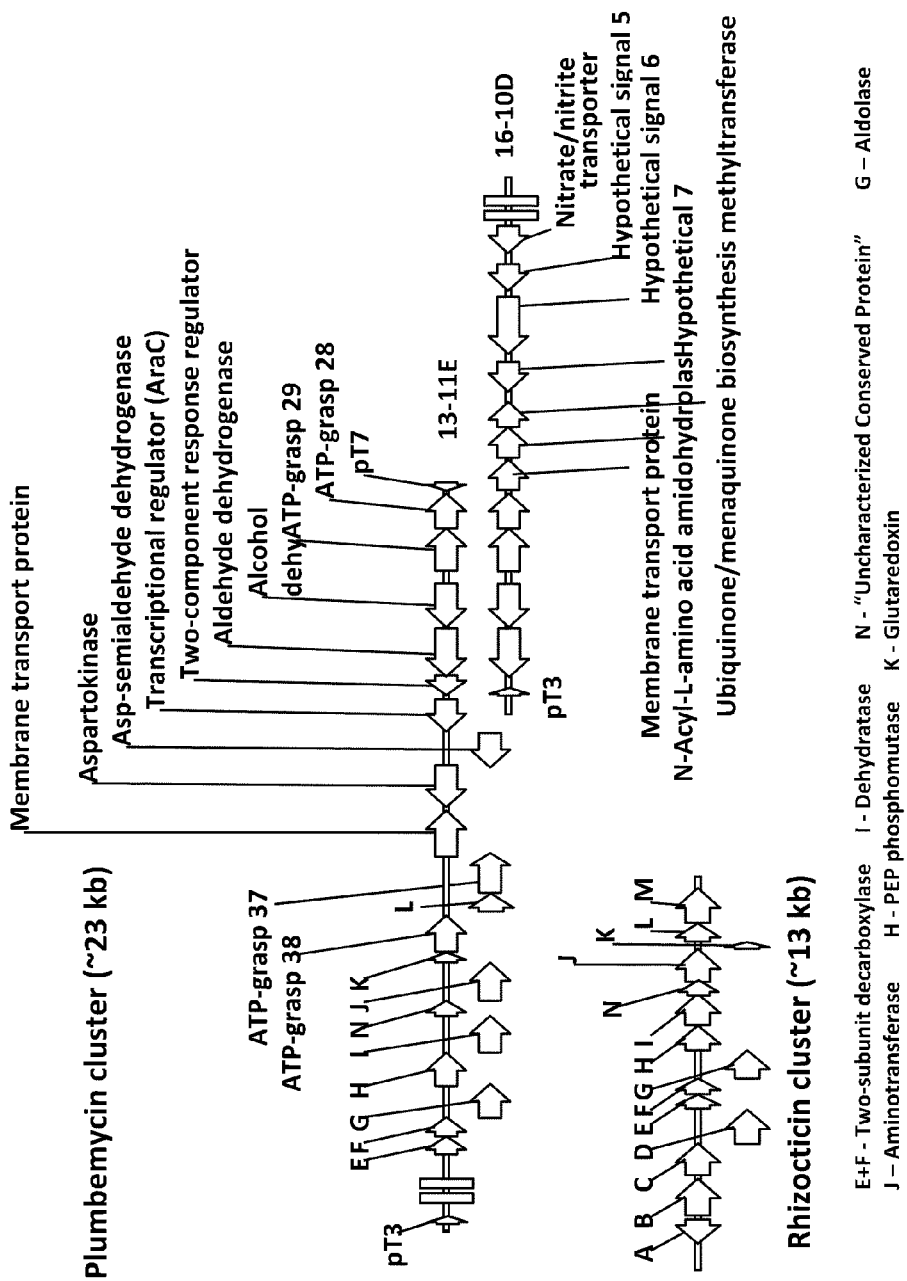
FIG. 4 shows the schematic diagram of the plumbemycin gene cluster with comparison to the rhizocticin gene cluster.

Eight consecutive open reading frames identified in the *S. plumbeus* sequence (pluE, F, G, H, I, N, J, K) are homologous to genes of rhizocticin biosynthesis in *Bacillus subtilis* ATCC6633 (rhiE, F, G, H, I, N, J, K), and their organization is the same as that of their rhi counterparts (See FIG. 4). Corresponding Rhi proteins involved in the biosynthesis of the APPA moiety of tripeptides rhizocticins include: PEP phosphomutase RhiH, two subunit phosphonopyruvate decarboxylase RhiE/RhiF, aldolase RhiG, aminotransferase RhiJ, kinase homolog RhiI, glutaredoxin RhiK, and hypothetical protein RhiN. Two genes encoding ATP-grasp superfamily proteins are located immediately downstream of and in the same operon as pluE-K genes (ATP-grasp 37 and 38). Two ATP-grasp proteins acting as amino acid ligases are also involved in the rhizocticin biosynthesis. The homolog of rhiL encoding putative phosphodiesterase with unknown function, pluL, is located between ATP-grasp 38 and 37 genes.

Downstream of the plu operon described above is a set of co-oriented ORFs transcribed in the opposite direction and encoding putative alcohol dehydrogenase, aldehyde dehydrogenase, two-component response regulator, AraC-like transcriptional regulator, aspartate semialdehyde dehydrogenase, and aspartokinase. Yet further downstream there are two more ATP-grasp genes (ATP-grasp 29 and 28) followed by genes encoding putative membrane transporter, N-acyl-L-amino acid amidohydrolase, and ubiquinone biosynthesis methyltransferase.

The homolog of threonine synthase gene, rhiB, present in the rhizocticin gene cluster and involved in the self-resistance mechanism was not found within the *S. plumbeus* sequence.

C. Isolated Nucleic Acids

The term "nucleic acid" used herein refers to a single or double-stranded polymer of deoxyribonucleotide or ribonucleotide bases read from the 5' to the 3' end. Nucleic acid molecules may also optionally contain synthetic, non-natural or altered nucleotide bases that permit correct read through by a polymerase and do not alter expression of a polypeptide encoded by that nucleic acid molecule.

As used herein, "an isolated nucleic acid" refers to a nucleic acid that is no longer accompanied by some of materials with which it is associated in its natural state or to a nucleic acid the structure of which is not identical to that of any of naturally occurring nucleic acid. Examples of isolated nucleic acids may include: (1) DNAs which have the sequence of part of a naturally occurring genomic DNA molecules but are not flanked by two coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. An isolated nucleic acid may also be comprised of one or more segments of cDNA, genomic DNA or synthetic DNA.

Further, the term "nucleotide sequence" or "nucleic acid sequence" refers to both the sense and antisense strands of a nucleic acid as either individual single strands or in the duplex. It includes, but is not limited to, self-replicating plasmids, chromosomal sequences, and infectious polymers of DNA or RNA.

Nucleotide sequences having homology to the rhi or plu genes, or when translated to the Rhi or Plu proteins, may be isolated according to at least one embodiment of the present disclosure. According to at least one embodiment of an isolated nucleic acid of the present disclosure, the isolated nucleic acid comprises a nucleotide sequence encoding a polypeptide having a sequence identity of about 70 percent or greater to an amino acid sequence selected from the group consisting of SEQ ID NOS. 2-13, and 15-23. According to at least one exemplary embodiment of the isolated nucleotide sequence, the sequence identity may be selected from the group consisting of at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%.

According to at least one embodiment of an isolated nucleic acid of the present disclosure, the isolated nucleic acid comprises a first nucleotide sequence encoding a polypeptide having a sequence identity of 70 percent or greater to SEQ ID NO: 7, and a second nucleotide sequence encoding a polypeptide having a sequence identity of 70 percent or greater to SEQ ID NO: 8. Optionally, the isolated nucleic acid may further comprise one or more nucleotide sequences which encode a polypeptide that has a 70 percent or greater identity to one of SEQ ID NOS. 2-6, 9-13. Further, in an exemplary embodiment of the isolated nucleic acid, the isolated nucleic acid may have a sequence identity of at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87, at least about 88%, at least about 89%, at least about 90%, at least about 91%, at least about 92%, at least about 93%, at least about 94%, at least about 95%, at least about 96%, at least about 97%, at least about 98%, at least about 99%, and about 100% to one or more of SEQ ID NOS. 2-13.

According to at least one embodiment of an isolated nucleic acid of the present disclosure, the isolated nucleic acid comprises a nucleotide sequence that has a sequence identity of at least 60% to an APPA nucleotide sequence selected from a group consisting of nucleotide ranges 13954-14844, 14999-16300, 17548-18771, 18807-19310, 19322-19882, 19879-20892, 20889-21779, 21802-22890, 22926-23324, 23324-24505, 24498-24755, and 24771-25418 of SEQ ID NO: 1, and nucleotide ranges 1449-2174, 3378-3683, 3683-4825, 4822-5286, 5283-6398, 6395-7387, 7327-8361, 8358-8930, and 8934-9458 of SEQ ID NO: 14. In at least one exemplary embodiment of the isolated nucleotide, the sequence identity of the isolated nucleotide may be selected from the group consisting of at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87, at least about 88%, at least about 89%, at least about 90%, at least about 91%, at least about 92%, at least about 93%, at least about 94%, at least about 95%, at least about 96%, at least about 97%, at least about 98%, at least about 99%, and about 100%.

It is well known in the art that one or more amino acids in a native sequence can be substituted with another amino acid(s), where the charge and polarity are similar to that of the native amino acid, i.e., a conservative amino acid substitution, resulting in a "silent" change. Biologically functional equivalents of the proteins or fragments thereof of the present disclosure may have 10 or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present disclosure.

It is also understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, obtain a protein with like or superior properties. It is thus contemplated herein that various changes may be made in the amino acid sequences of the proteins or fragments of the present disclosure, or corresponding DNA sequences that encode the polypeptides, without appreciable loss of their biological utility or activity. It is understood that codons capable of coding for such amino acid changes are known in the art.

D. Vectors and Transformed Cells

According to at least one embodiment of the present disclosure, a vector comprises an embodiment of an isolated nucleic acid of the present disclosure. The isolated nucleic acid may in an exemplary embodiment include all or part of the rhi operon, the plu operon, or an isolated nucleic acid with at least 60 percent identity thereto. The term "vector" is defined herein as a linear or circular DNA molecule, such as a plasmid, cosmid, viral particle, or phage. The vector may be a single vector or plasmid or two or more vectors or plasmids which together contain the total DNA to be introduced into the host cell. The transformed cell prior to, or after insertion of the vector, may also be described as a host cell. Further, a transformed cell of the present disclosure, according to an exemplary embodiment, comprises an embodiment of a vector of the present disclosure. A transformed cell of the present disclosure may be a bacterial cell, a mammalian cell, an insect cell, or a yeast cell according to at least one exemplary embodiment. Further, the transformed cell may optionally be either from the genus *Bacillus*, such as *B. subtilis*, or the genus *Streptomyces*.

Further, according to at least one embodiment of a transformed cell of the present disclosure, the transformed cell comprises a vector which comprises the isolated nucleic acid, wherein the transformed cell is capable of producing an APPA-containing peptide. In at least one embodiment, the APPA-containing peptide may be plumbemycin, or rhizocticin, where the rhizocticin may be rhizocticin B.

1. Microbial Vectors and Transformed Microbial Cells

The embodiments of isolated nucleotide sequences of the present disclosure may be introduced into a wide variety of prokaryotic and eukaryotic microorganism hosts to produce APPA-containing peptides. The term "bacteria" includes prokaryotic and eukaryotic microbial species such as bacteria and fungi. Fungi include yeast and filamentous fungi. Illustrative prokaryotes, both Gram-negative and Gram-positive, include Bacillaceae, such as *Bacillus*; Streptomycetaceae, such as *Streptomyces*; Enterobacteriaceae, such as *Escherichia, Erwinia, Shigella, Salmonella*, and *Proteus*; Rhizobiceae, such as *Rhizobium*; Spirillaceae, such as *Photobacterium, Zymomonas, Serratia, Aeromonas, Vibrio, Desulfovibrio, Spirillum*; Lactobacillaceae; Pseudomonadaceae, such as *Pseudomonas* and *Acetobacter*, Azotobacteraceae, Actinomycetales, and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

It is well known that exogenous nucleic acids encoding polypeptides of interest can be introduced into a microbial host cell, such as a bacterial cell or a fungal cell, using a recombinant vector. The present disclosure also includes a fungal or bacterial vector comprising an isolated nucleotide sequence. Further, the present disclosure also relates to a bacterial or fungal cell comprising an embodiment of a bacterial or fungal vector of the present disclosure.

Embodiments of isolated nucleic acids encoding proteins responsible for APPA-containing peptide production can, for example, be suitably inserted into a replicable vector for expression in a bacterium under the control of a suitable promoter for that bacterium. Many vectors are available for this purpose, and selection of the appropriate vector will depend mainly on the size of the nucleic acid to be inserted into the vector and the particular host cell to be transformed with the vector. Each vector may contain various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

In general, vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an E. coli species (see, e.g., Bolivar et al., Gene 2:95 (1977)). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

In at least one embodiment of an isolated nucleic acids encoding proteins responsible for the production of APPA-containing peptides, the isolated nucleic acid may be expressed not only directly, but also as a fusion with another polypeptide (such as further described herein, and in the Methods), preferably a signal sequence or other polypeptide having a specific cleavage site at the N-terminus of the mature polypeptide. In general, the signal sequence may be a component of the vector, or it may be a part of the polypeptide encoding DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, beta-lactamase, or heat-stable enterotoxin II leaders and the like.

Embodiments of vectors described herein also may contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, streptomycin, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous protein or fragment thereof produce a protein conferring drug resistance and thus survive the selection regiment.

Exemplary vectors may also contains an inducible promoter that is recognized by the host bacterial organism and is operably linked to the nucleic acid encoding, for example, the nucleic acid molecule encoding the C. sarokiniana protein or fragment thereof of interest. Inducible promoters suitable for use with bacterial hosts include the beta-lactamase, E. coli lamda phage $P_L$ and $P_R$, and E. coli galactose, arabinose, alkaline phosphatase, tryptophan (trp), and lactose operon promoter systems and variations thereof (Chang et al., Nature 275:615 (1978); Goeddel et al., Nature 281:544 (1979); Guzman et al., J. Bacteriol. 174:7716-7728 (1992); Goeddel, Nucleic Acids Res. 8:4057 (1980); EP 36,776) and hybrid promoters such as the tac promoter (deBoer et al., Proc. Natl. Acad. Sci. (USA) 80:21-25 (1983)). However, other known bacterial inducible promoters are suitable (Siebenlist et al., Cell 20:269 (1980)), and well known.

Promoters for use in bacterial systems also generally contain a Shine-Dalgarno (S.D.) sequence or a consensus sequence thereof operably linked to the DNA encoding the polypeptide of interest. The promoter can be removed from the bacterial source DNA by restriction enzyme digestion and inserted into the vector containing the desired DNA coding sequence, or vice versa.

Alternatively, embodiments of vectors described herein can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors with DNA from various Bacillus strains readily integrate into the Bacillus chromosome. Integrating vectors may also be comprised of bacteriophage or transposon sequences.

It is, of course, necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. E. coli strain W3110 is a preferred host or parent host because it is a common host strain for recombinant DNA product fermentations. Preferably, the host cell should secrete minimal amounts of proteolytic enzymes.

Numerous methods of transformation are known, for example, calcium phosphate and electroporation. Depending on the host cell used, transformation is done using standard techniques appropriate to such cells. The calcium treatment employing calcium chloride, as described in section 1.82 of Sambrook et al., Molecular Cloning: A Laboratory Manual, New York: Cold Spring Harbor Laboratory Press, (1989), may be used for bacterial cells that contain substantial cell-wall barriers. Another method for transformation employs polyethylene glycol/DMSO, as described in Chung and Miller (Chung and Miller, Nucleic Acids Res. 16:3580 (1988)). Yet another method is the use of the technique termed electroporation. In addition, bacterial cells can be readily transformed using various forms of phages (i.e., transducing, temperate, lytic and lysogenic), suicide vectors for inserting DNA directly into the chromosome, and through homologous recombination using either phages, suicide vectors or linear DNA.

Bacterial cells used to produce the polypeptide of interest for purposes of this disclosure are cultured in suitable media in which the promoters for the nucleic acid encoding the heterologous polypeptide can be artificially induced as described generally, e.g., in Sambrook et al., Molecular Cloning: A Laboratory Manual, New York: Cold Spring Harbor Laboratory Press, (1989). Examples of suitable media are given in currently active U.S. Pat. Nos. 5,304,472 and 5,342,763.

An embodiment of a yeast vector may include one or more of the following: a promoter sequence, fusion partner sequence, leader sequence, transcription termination sequence, a selectable marker. These elements can be combined into an expression cassette, which may be maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al., Gene, 8:17-24 (1979)), pC1/1 (Brake et al., Proc. Natl. Acad. Sci. USA, 81:4642-4646 (1984)), and YRp17 (Stinchcomb et al., J. Mol. Biol., 158:157 (1982)).

Useful yeast promoter sequences may be derived from genes encoding enzymes in the metabolic pathway. Examples of such genes include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO5 gene, encoding acid phosphatase, also provides useful promoter sequences (Myanohara et al., Proc. Natl. Acad. Sci. USA, 80:1 (1983)). In addition, synthetic promoters which do not occur in nature also function as yeast promoters. Examples of such hybrid promoters include the ADH regulatory sequence linked to the GAP transcription activation region (expired U.S. Pat. Nos. 4,876,197 and 4,880,734). Other examples of hybrid promoters include promoters which consist of the regulatory sequences of the ADH2, GALA, GAL10, or PH05 genes, combined with the transcriptional activation region of a glycolytic enzyme gene such as GAP or PyK (E.P.O. Pub. No. 164556). Furthermore, a yeast promoter can include naturally occurring promoters of non-yeast origin that have the ability to bind yeast RNA polymerase and initiate transcription. Examples of such promoters include, inter alia, (Cohen et al., Proc. Natl. Acad. Sci. USA, 77:1078 (1980); Henikoff et al., Nature 283:835 (1981); Hollenberg et al., Curr. Topics Microbiol. Immunol., 96:119 (1981); Mercerau-Puigalon et al., Gene, 11:163 (1980); and Panthier et al., Curr. Genet., 2:109 (1980)).

Intracellularly expressed fusion proteins provide an alternative to direct expression of the polypeptides of interest. Typically, a DNA sequence encoding the N-terminal portion of a stable protein, a fusion partner, is fused to the 5' end of heterologous structural nucleotide sequence encoding the desired polypeptide. Upon expression, this vector will provide a fusion of the two amino acid sequences. The DNA sequence at the junction of the two amino acid sequences may or may not encode a cleavable site. See, e.g., E.P.O. Pub. No. 196056. Another example is a ubiquitin fusion protein. Such a ubiquitin fusion protein preferably retains a site for a processing enzyme (e.g. ubiquitin-specific processing protease) to cleave the ubiquitin from the polypeptide of the present disclosure. Through this method, a mature polypeptide of the present disclosure can be isolated.

Alternatively, polypeptides or proteins of the present disclosure may also be secreted from the cell into the growth media by creating chimeric DNA molecules that encode a fusion protein comprised of a leader sequence fragment that provides for secretion in yeast of the polypeptides. Preferably, there are processing sites encoded between the leader fragment and the polypeptide-encoding sequence fragment that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (E.P.O. Pub. No. 12873; J.P.O. Pub. No. 62,096,086) and the A-factor gene (expired U.S. Pat. No. 4,588,684). Alternatively, leader sequences of non-yeast origin, such as an interferon leader, exist that also provide for secretion in yeast (E.P.O. Pub. No. 60057).

One class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (expired U.S. Pat. Nos. 4,546,083 and 4,870,008; and E.P.O. Pub. No. 324274). Additional leaders employing an alpha-factor leader fragment that provides for secretion include hybrid alpha-factor leaders made with a pre-sequence of a first yeast, but a pro-region from a second yeast alpha factor.

Examples of transcription terminator sequence and other yeast-recognized termination sequences, such as those coding for glycolytic enzymes, are also known.

Alternatively, embodiments of the vectors described herein can be integrated into the yeast genome with an integrating vector. Integrating vectors typically contain at least one sequence homologous to a yeast chromosome that allows the vector to integrate, and may contain two homologous sequences flanking the expression vector. An integrating vector may be directed to a specific locus in yeast by selecting the appropriate homologous sequence for inclusion in the vector. The chromosomal sequences included in the vector may occur either as a single segment in the vector, which results in the integration of the entire vector, or as two segments homologous to adjacent segments in the chromosome and flanking the expression vector in the vector, which results in the stable integration of only the expression vector.

Vectors, either extrachromosomal replicons or integrating vectors, have been developed for transformation into many yeasts. For example, expression vectors have been developed for, inter alia, the following yeasts: *Candida albicans* (Kurtz, et al., Mol. Cell. Biol., 6:142 (1986)), *Candida maltosa* (Kunze et al., J. Basic Microbiol., 25:141 (1985)); *Hansenula polymorphs* (Gleeson et al., J. Gen. Microbiol. 132:3459 (1986); Roggenkamp et al., Mol. Gen. Genet. 202:302 (1986)); *Kluyveromyces fragilis* (Das et al., J. Bacteriol. 158:1165 (1984)); *Kluyveromyces lactis* (De Louvencourt et al., J. Bacteriol. 154:737 (1983); Van den Berg et al., Bio/Technology 8:135 (1990)); *Pichia guillerimondii* (Kunze et al., J. Basic Microbiol. 25:141 (1985)); *Pichia pastoris* (Cregg et al., Mol. Cell. Biol. 5:3376 (1985); expired U.S. Pat. Nos. 4,837,148 and 4,929,555); *Saccharomyces cerevisiae* (Hinnen et al., Proc. Natl. Acad. Sci. USA 75:1929 (1978); Ito et al., J. Bacteriol. 153:163 (1983)); *Schizosaccharomyces pombe* (Beach and Nurse, Nature 300:706 (1981)); and *Yarrowia lipolytica* (Davidow, et al., Curr. Genet. 10:380471 (1985); and Gaillardin et al., Curr. Genet. 10:49 (1985)).

Methods of introducing exogenous nucleic acids into yeast hosts are well-known, and typically include either the transformation of spheroplasts or of intact yeast cells treated with alkali cations. Transformation procedures usually vary with the yeast species to be transformed. See e.g., Kurtz et al., Mol. Cell. Biol. 6:142 (1986); Kunze et al., J. Basic Microbiol. 25:141 (1985) for *Candida*. See, e.g., Gleeson et al., J. Gen. Microbiol. 132:3459 (1986); Roggenkamp et al., Mol. Gen. Genet. 202:302 (1986) for *Hansenula*. See, e.g., Das et al., J. Bacteriol. 158:1165 (1984); De Louvencourt et al., J. Bacteriol. 154:1165 (1983); Van den Berg et al., Bio/Technology 8:135 (1990) for *Kluyveromyces*. See, e.g., Cregg et al., Mol. Cell. Biol. 5:3376 (1985); Kunze et al., J. Basic Microbiol. 25:141 (1985); expired U.S. Pat. Nos. 4,837,148 and 4,929,555 for *Pichia*. See, e.g., Hinnen et al., Proc. Natl. Acad. Sci. USA 75:1929 (1978); Ito et al., J. Bacteriol. 153:163 (1983) for *Saccharomyces*. See, e.g., Beach and Nurse, Nature 300:706 (1981) for *Schizosaccharomyces*. See, e.g., Davidow et al., Curr. Genet. 10:39 (1985); Gaillardin et al., Curr. Genet. 10:49 (1985) for *Yarrowia*.

In order to obtain exemplary expression polypeptides or proteins of interest, host cells derived from the transformants are incubated under conditions which allow expression of the recombinant polypeptide-encoding sequence. These conditions will vary, dependent upon the host cell selected. However, the conditions are readily ascertainable to those of ordinary skill and knowledge in the art.

Detection of polypeptides expressed in the transformed cell may be performed by several methods. For example, a polypeptide or protein may be detected by its immunological reactivity with antibodies.

Polypeptides or proteins of the present disclosure may be isolated from the cell by lysis, if formed intracellularly, or isolated from the culture medium, if secreted, by conventional methods.

2. Mammalian Vectors and Transformed Mammalian Cells

The present disclosure also relates to mammalian vectors comprising embodiments of an isolated nucleic acid. The present disclosure also relates to a mammalian cell comprising an embodiment of a mammalian vector of the present disclosure.

Exemplary embodiments of mammalian vectors may be any vector which can be conveniently subjected to recombinant DNA procedures. Many vectors are available for this purpose, and a suitable vector is one that is compatible with the desired function (e.g., transient expression, long term expression, integration, replication, amplification) and in which the control elements are compatible with the host cell. The control elements are those non-translated regions of the vector—promoters, enhancers, 5' and 3' untranslated regions—which interact with host cellular proteins to carry out transcription and translation.

Exemplary vectors suitable for replication in mammalian cells may include viral replicons, or sequences that ensure integration of an embodiment of the isolated nucleic acid of the present disclosure into the host genome. Suitable vectors may include, for example, those derived from simian virus SV40, retroviruses, bovine papilloma virus, vaccinia virus, and adenovirus. The components of the vectors, e.g. replicons, selection genes, enhancers, promoters, and the like, may be obtained from natural sources or synthesized by known procedures. (See, Kaufman et al, J. Mol. Biol., 159:511-521 (1982); and Kaufman, Proc. Natl. Acad. Sci., USA, 82:689-693 (1985)).

An exemplary vector may be one derived from vaccinia viruses. In this case, an embodiment of the isolated nucleic acid of the present disclosure is inserted into the vaccinia genome. Techniques for the insertion of foreign DNA into the vaccinia virus genome are known in the art, and utilize, for example, homologous recombination. The insertion of the foreign DNA is generally into a gene which is non-essential in nature, for example, the thymidine kinase gene (tk), which also provides a selectable marker. Plasmid shuttle vectors that greatly facilitate the vectorion of recombinant viruses have been described (see, for example, Mackett et al, J. Virol. 49: 857 (1984); Chakrabarti et al., Mol. Cell. Biol. 5: 3403 (1985); Moss, In: Gene Transfer Vectors For Mammalian Cells (Miller and Calos, eds., Cold Spring Harbor Laboratory, N.Y., p. 10, (1987)). Expression of proteins encoded by an embodiment of the isolated nucleic acid of the present disclosure then occurs in cells or animals which are infected with the live recombinant vaccinia virus.

Exemplary vectors, such as mammalian expression vectors, may contain one or more eukaryotic control elements that are capable of expression in mammalian cells. The control element is comprised of at least a promoter to mediate transcription of foreign DNA sequences. Suitable promoters for mammalian cells are known in the art and include viral promoters such as that from simian virus 40 (SV40), cytomegalovirus (CMV), Rous sarcoma virus (RSV), adenovirus (ADV), and bovine papilloma virus (BPV).

In addition, the control element may also be comprised of a termination sequence and poly(A) addition sequences which are operably linked to an embodiment of the isolated nucleic acid of the present disclosure. The control element may also be comprised of an enhancer sequence which increases the expression of a protein encoded by an embodiment of the isolated nucleic acid of the present disclosure.

Furthermore, the control element may also be comprised of an enhancer, which is any regulatory DNA sequence that can stimulate transcription up to 1000-fold or more when linked to endogenous or heterologous promoters, with synthesis beginning at the normal mRNA start site. Enhancers may also be active when they are placed upstream or downstream from the transcription initiation site, in either normal or flipped orientation, or at a distance of more than 1000 nucleotides from the promoter (Maniatis et al. Science, 236:1237 (1987); Alberts et al., Molecular Biology of the Cell, 2nd ed. (1989)). Enhancers derived from viruses may be particularly useful, because they typically have a broader host range. Examples include the SV40 early gene enhancer (Dijkema et al, EMBO J., 4:761 (1985)) and the enhancer/promoters derived from the long terminal repeat (LTR) of the Rous Sarcoma Virus (Gorman et al., Proc. Natl. Acad. Sci. 79:6777 (1982b)) and from human cytomegalovirus (Boshart et al., Cell, 41:521 (1985)). Additionally, some enhancers are regulatable and become active only in the presence of an inducer, such as a hormone or metal ion (Sassone-Corsi and Borelli, Trends Genet. 2:215 (1986); Maniatis et al. Science, 236:1237 (1987)).

Where selection is intended, sequences which encode selectable markers may also be included in the vector. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

For homologous recombination, exemplary vectors can be prepared where the amplifiable gene will be flanked, normally on both sides with DNA homologous with the DNA of the target region. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

Embodiments of integrating vectors may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like. Usually during the preparation of a vector where various fragments are joined, the fragments, intermediate vectors and vectors will be carried on a cloning vector comprising a replication system functional in a prokaryotic host, e.g., E. coli, and a marker for selection, e.g., biocide resistance, complementation to an auxotrophic host, etc. Other functional sequences may also be present, such as polylinkers, for ease of introduction and excision of the vector or portions thereof, or the like. A large number of cloning vectors are available such as pBR322, the pUC series, etc. These vectors may then be used for integration into the primary mammalian host.

The mammalian vectors described herein may be synthesized by techniques well known to those skilled in this art. Other appropriate expression vectors of which numerous types are known in the art for mammalian expression can also be used for this purpose.

Mammalian cell lines available as host cells are known in the art and include many immortalized cell lines available from the American Type Culture Collection (ATCC). Exemplary mammalian host cells include primate cell lines and rodent cell lines, including transformed cell lines. Suitable cell lines include, but are not limited to, Chinese hamster ovary (CHO) cells, HeLa cells, baby hamster kidney (BHK) cells, monkey kidney cells (COS-1), human hepatocellular carcinoma cells (e.g., Hep G2), human adenovirus transformed 293 cells, mouse L-929 cells, HaK hamster cell lines, murine 3T3 cells derived from Swiss, Balb-c or NIH mice and a number of other cell lines.

The DNA can be introduced into the host cell by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming mammalian cells are well known (see Keown et al., Methods Enzymol. (1989), Keown et al., Methods Enzymol. 185:527-537 (1990); Mansour et al., Nature 336:348-352, (1988)).

3. Insect Vectors and Transformed Insect Cells

The present disclosure, according to at least one exemplary embodiment, relates to an insect vectors comprising an isolated nucleic acid. The present disclosure also relates to an insect cell comprising an insect recombinant vector.

The choice of a vector will depend on the compatibility of the vector with the insect host cell into which the vector is to be introduced. In addition, the insect vector may be an expression vector. An embodiment of the isolated nucleic acid may be suitably inserted into a vector for expression in the insect cell under a suitable promoter for insect cells. Many vectors are available for this purpose, and selection of the appropriate vector will depend mainly on the size of the nucleic acid molecule to be inserted into the vector and the particular host cell to be transformed with the vector. Each vector contains various components depending on its function (amplification of DNA or expression of DNA) and the particular host cell with which it is compatible. The vector components for insect cell transformation generally include, but not limited to, one or more of the following: a signal sequence, and origin of replication, one or more marker genes, and an inducible promoter.

The insect vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the insect cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the insect host. The additional nucleic acid sequences enable the vector to be integrated into the host cell genome at a precise location(s) in the chromosome(s). To increase the likelihood of integration at a precise location, in at least one embodiment there may be two nucleic acid sequences which individually contain a sufficient number of nucleic acids, such as 400 bp to 1500 bp, or 800 bp to 1000 bp, which are highly homologous with the corresponding target sequence to enhance the probability of homologous recombination. These nucleic acid sequences may be any sequence that is homologous with a target sequence in the genome of the insect host cell, and, furthermore, may be non-encoding or encoding sequences.

Baculovirus expression vectors (BEVs) have become important tools for the expression of foreign genes, both for basic research and for the production of proteins with direct clinical applications in human and veterinary medicine (Doerfler, Curr. Top. Microbiol. Immunol. 131: 51-68 (1968); Luckow and Summers, Bio/Technology 6: 47-55 (1988a); Miller, Annual Review of Microbiol. 42: 177-199 (1988); Summers, Curr. Comm. Molecular Biology, Cold Spring Harbor Press, Cold Spring Harbor, N.Y. (1988); all of which are herein incorporated by reference in their entirety). BEVs are recombinant insect viruses in which the coding sequence for a chosen foreign gene has been inserted behind a baculovirus promoter in place of the viral gene, e.g., polyhedrin.

The use of baculovirus vectors relies upon the host cells being derived from Lepidopteran insects such as *Spodoptera frugiperda* or *Trichoplusia ni*. The preferred *Spodoptera frugiperda* cell line is the cell line Sf9. The *Spodoptera frugiperda* Sf9 cell line was obtained from American Type Culture Collection (Manassas, Va.) and is assigned accession number ATCC CRL 1711 (Summers and Smith, A Manual of Methods for Baculovirus Vectors and Insect Cell Culture Procedures, Texas Ag. Exper. Station Bulletin No. 1555 (1988), herein incorporated by reference in its entirety). Other insect cell systems, such as the silkworm *B. mori* may also be used.

The proteins expressed by the BEVs are, therefore, synthesized, modified and transported in host cells derived from Lepidopteran insects. Most of the genes that have been inserted and produced in the baculovirus expression vector system have been derived from vertebrate species. Other baculovirus genes in addition to the polyhedrin promoter may be employed to advantage in a baculovirus expression system. These include immediate-early (alpha), delayed-early (beta), late (gamma), or very late (delta), according to the phase of the viral infection during which they are expressed. The expression of these genes occurs sequentially, probably as the result of a "cascade" mechanism of transcriptional regulation. (Guarino and Summers, J. Virol. 57:563-571 (1986); Guarino and Summers, J. Virol. 61:2091-2099 (1987); Guarino and Summers, Virol. 162:444-451 (1988); all of which are herein incorporated by reference in their entirety).

Insect recombinant vectors are useful as intermediates for the infection or transformation of insect cell systems. For example, an insect recombinant vector containing a nucleic acid molecule encoding a baculovirus transcriptional promoter followed downstream by an insect signal DNA sequence is capable of directing the secretion of the desired biologically active protein (encoded by the isolated nucleic acid) from the insect cell. The exemplary vector may utilize a baculovirus transcriptional promoter region derived from any of the over 500 baculoviruses generally infecting insects, such as for example the Orders Lepidoptera, Diptera, Orthoptera, Coleoptera and Hymenoptera, including for example but not limited to the viral DNAs of *Autographa californica* MNPV, *Bombyx mori* NPV, *Trichoplusia ni* MNPV, *Rachiplusia ou* MNPV or *Galleria mellonella* MNPV, wherein said baculovirus transcriptional promoter is a baculovirus immediate-early gene IE1 or IEN promoter; an immediate-early gene in combination with a baculovirus delayed-early gene promoter region selected from the group consisting of 39K and a HindIII-k fragment delayed-early gene; or a baculovirus late gene promoter. The immediate-early or delayed-early promoters can be enhanced with transcriptional enhancer elements. The insect signal DNA sequence may code for a signal peptide of a *Lepidopteran adipokinetic* hormone precursor or a signal peptide of the *Manduca sexta* adipokinetic hormone precursor. Other insect signal DNA sequences include a signal peptide of the Orthoptera *Schistocerca gregaria* locust adipokinetic hormone precurser and the *Drosophila melanogaster* cuticle genes CP1, CP2, CP3 or CP4 or for an insect signal peptide having substantially a similar chemical composition and function.

Recombinant protein expression in insect cells may be achieved by viral infection or stable transformation. For viral infection, the desired gene may be cloned into baculovirus at the site of the wild-type polyhedron gene. The polyhedron gene is a component of a protein coat in occlusions which encapsulate virus particles. Deletion or insertion in the polyhedron gene results the failure to form occlusion bodies. Occlusion negative viruses are morphologically different from occlusion positive viruses and enable one skilled in the art to identify and purify recombinant viruses.

According to at least one embodiment, vectors of the present disclosure may contain one or more selectable markers which permit easy selection of transformed cells. A selectable marker is a gene the product of which provides, for example biocide or viral resistance, resistance to heavy metals, prototrophy to auxotrophs, and the like. Selection may be accomplished by co-transformation, e.g., as described in WO 91/17243, a nucleic acid sequence of the present disclosure may be operably linked to a suitable promoter sequence. The promoter sequence is a nucleic acid sequence which is recognized by the insect host cell for expression of the nucleic acid sequence. The promoter sequence contains transcription and translation control sequences which mediate the expression of the protein or fragment thereof. The promoter may be any nucleic acid sequence which shows transcriptional activity in the insect host cell of choice and may be obtained from genes encoding polypeptides either homologous or heterologous to the host cell.

For example, an embodiment of the isolated nucleic acid of the present disclosure may also be operably linked to a suitable leader sequence. A leader sequence is a non-translated region of an mRNA which is important for translation by the insect host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the insect host cell of choice may be used in the present disclosure.

A polyadenylation sequence may also be operably linked to the 3' terminus of the nucleic acid sequence of the present disclosure. The polyadenylation sequence is a sequence which when transcribed is recognized by the insect host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present disclosure.

Standard methods of insect cell culture, co-transfection and preparation of vectors are set forth in Summers and Smith (Summers and Smith, A Manual of Methods for Baculovirus Vectors and Insect Cell Culture Procedures, Texas Agricultural Experiment Station Bulletin No. 1555, Texas A&M University (1987)). Procedures for the cultivation of viruses and cells are described in Volkman and Summers, J. Virol 19: 820-832 (1975) and Volkman et al., J. Virol 19: 820-832 (1976); both of which are herein incorporated by reference in their entirety.

E. Methods of In Vivo Production of APPA-Containing Peptides

Methods for the production of APPA-containing peptides are described herein using embodiments of vectors and transformed cells as described above. The APPA-containing peptides may, in an exemplary embodiment, be a rhizocticin, such as rhizocticin B, or a plumbemycin, such as plumbemycin A. An embodiment of production of an APPA-containing peptide is described in Example 2.

According to at least one embodiment of a method for producing an APPA-containing peptide of the present disclosure, the method comprises the steps of transforming a host cell with a nucleic acid comprising a nucleotide sequence encoding a polypeptide having a sequence identity of 70 percent or greater to an amino acid sequence selected from the group consisting of SEQ ID NOS. 2-13, and 15-23, and growing the transformed host cell under conditions to produce an APPA-containing peptide. Further, according to at least one embodiment of the method, the untransformed host cell is not capable of producing the APPA-containing peptide. Moreover, the APPA-containing peptide, according to at least one embodiment, is a rhizocticin, or a plumbemycin. Optionally, the method for producing an APPA-containing peptide, according to an exemplary embodiment, may further comprise the step of purifying the APPA-containing peptide from the transformed host cell or the supernatant from the transformed host cell. Once purified, the APPA-containing peptide may, according to an exemplary embodiment, be chemically altered using standard techniques to replace the attached amino acid(s) attached to APPA to any other amino acid.

According to an exemplary embodiment, a transformed cell comprises the vector having the isolated nucleic acid, wherein the transformed cell is capable of producing an APPA-containing peptide. In at least one exemplary embodiment, an APPA-containing peptide may be any peptide comprising APPA as described above. Further, the transformed cell may be any one of those previously described above.

F. Rhizocticin Biosynthetic Pathway.

Figure 5:
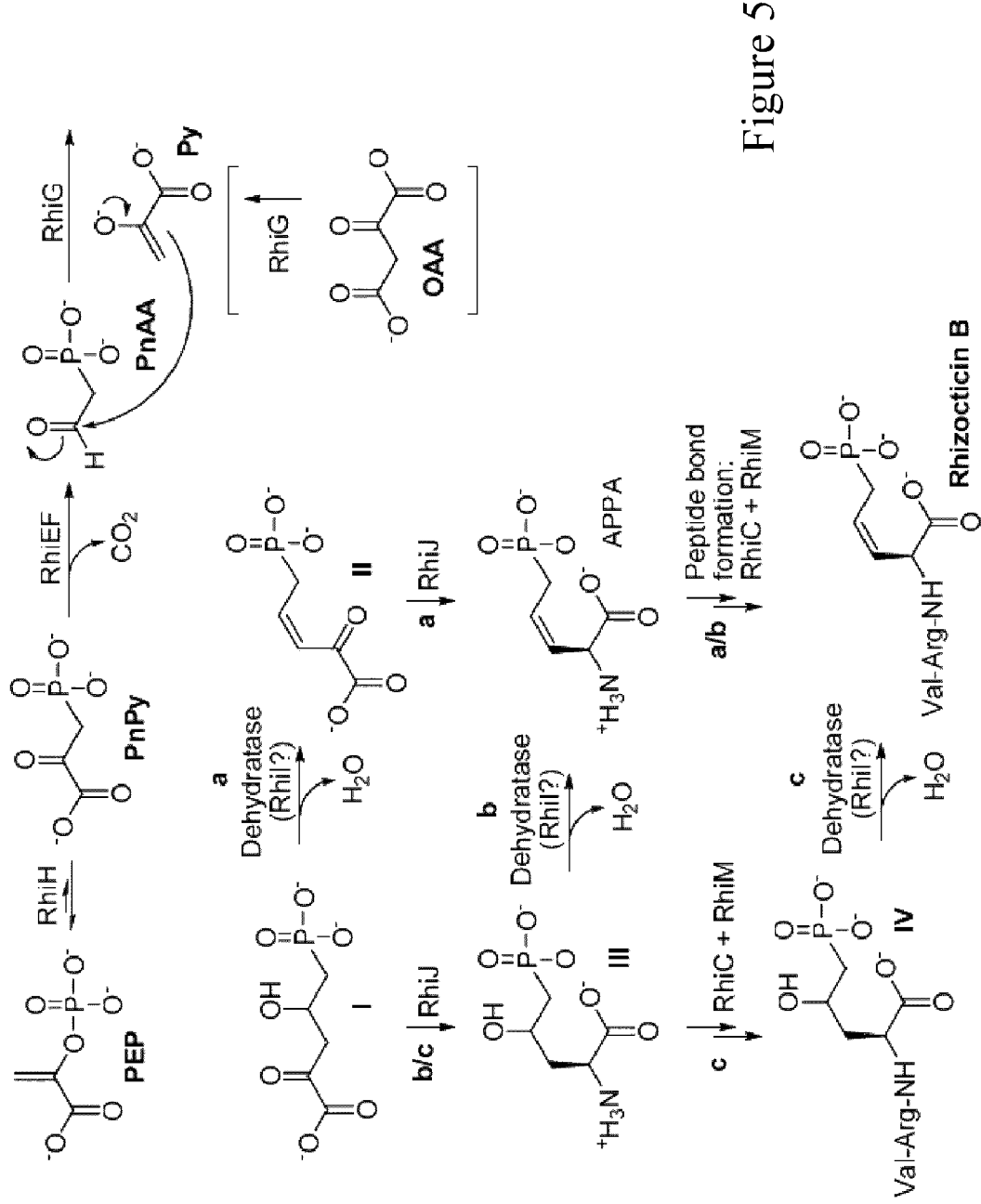
FIG. 5 shows the pathway for the biosynthesis of rhizocticins according to at least one embodiment of the present disclosure.

Based on the amino acid sequence homology of Rhi proteins to enzymes with known activities and previous knowledge of phosphonate biosynthetic pathways, an exemplary biosynthetic pathway for rhizocticins is shown in FIG. 5. According to an exemplary embodiment, PEP is first converted to PnPy by the action of the PEP mutase RhiH. PnPy then undergoes decarboxylation catalyzed by PnPy decarboxylase RhiE/RhiF to yield PnAA. The subsequent step is a novel transformation, an aldol reaction between PnAA and pyruvate (Py) catalyzed by the aldolase homolog RhiG.

A minimum of two steps, dehydration and aminotransfer, may be required to convert the putative RhiG product I to APPA. The aminotransferase RhiJ is responsible for the introduction of the amino group at C-2. RhiJ may catalyze a PLP-dependent γ-elimination of water in tandem with aminotransfer, single-handedly converting I to APPA. Another possibility is the activation of the hydroxyl leaving group via phosphorylation by the action of the kinase homolog RhiI Elimination could then be achieved by a yet unknown activity of RhiI (e.g. via acid-base catalysis) or by the action of RhiJ. Alternatively, RhiG could be responsible for aldol addition followed by dehydration. Regardless of the order in which dehydration and aminotransfer happen (path a vs. b), the APPA product may then be decorated at its N-terminus with Arg and Val (or Leu/Ile) by the action of carboxylate-amine ligases, such as RhiC and RhiM.

The timing of dehydration may also be later in the pathway. Namely, once intermediate I is converted by RhiJ to amino acid III, III may be incorporated by RhiC and RhiM into di- or tri-peptide precursor(s) IV of rhizocticins. In this case, the dehydration would commence on a peptide intermediate(s) IV. In this scenario, no α-amino group would be available for RhiJ-catalyzed PLP-dependent chemistry and at least one another enzyme must be involved. This path (c) is particularly appealing as it avoids the presence of toxic APPA as an intermediate.

In at least one embodiment, and although unusual for secondary metabolite biosynthesis, the glutaredoxin homolog RhiK may be involved in maintaining a reduced active state for specific proteins of the pathway, and RhiL and/or RhiN may be involved in a dehydration sequence.

EXAMPLES

Example 1

Fosmid Library Analysis

With the genome sequence available, the fosmid library of *B. subtilis* ATCC6633 was screened as described above using two sets of sequence-specific primers designed to amplify short sequences upstream of the putative rhizocticin cluster (within orf6 and within rhiM). Fosmid 2-11E was identified, and sequenced via the Sanger protocol using transposon insertions. The sequence of the insert of 2-11E originating from *B. subtilis* ATCC6633 DNA was identical to that of the corresponding fragment obtained through 454 sequencing of the genome with the exception of a single base pair mismatch located outside of the putative rhizocticin gene cluster.

*B. subtilis* ATCC6633 possesses a high degree of nucleotide sequence homology to *B. subtilis* 168. The putative rhizocticin gene cluster is a single site insertion of approximately 13 kb into the genome of *B. subtilis* 168. Although the genes of the rhizocticin cluster have no homologs within the *B. subtilis* 168 genome, the nucleotide sequences outside of the cluster are approximately 90% identical. Interestingly, *B. subtilis* 168 contains a gene cluster (ski) located near the "insertion site" of the rhizocticin gene cluster (star in FIG. 2, *B. subtilis* 168 operon). This gene cluster is absent from *B. subtilis* ATCC6633 (its corresponding location is shown as a star, FIG. 2, *B. subtilis* ATCC6633 operon). The skf gene cluster is responsible for the biosynthesis and export of and the immunity to sporulation killing factor. This peptide antibiotic produced by sporulating *B. subtilis* 168 causes lysis of non-sporulating sibling *B. subtilis* 168 cells. Thus, the rhi and skf gene clusters occupy essentially the same locus on the genomic DNA of related species, as commonly seen for the genes involved in secondary metabolism.

Example 2

Catalytic Activity of the PEP Mutase RhiH

The rhiH gene encoding putative PEP mutase was expressed in *E. coli* as a fusion protein with an N-terminal hexahistidine tag. Recombinant RhiH-N-His was purified to near homogeneity using metal affinity chromatography. The reversible reaction catalyzed by PEP mutase favors the formation of PEP. Subsequent decarboxylation of PnPy to PnAA catalyzed by PnPy decarboxylase provides the necessary driving force in many phosphonate pathways. Therefore, the enzymatic activity of RhiH-N-His was tested using a coupled assay with PnPy decarboxylase from *Bacteroides fragilis* prepared as a C-terminally His-tagged protein (Ppd-Bf-His).

Assay conditions were based on published procedures and are described in detail in the Methods. Briefly, the assay mixture containing PEP, catalytic TPP cofactor, and $Mg^{2+}$ was incubated with RhiH-N-His and Ppd-Bf-His. The extent of the reaction was analyzed using $^{31}P$ NMR spectroscopy. Upon incubation, PEP (δ −0.2 ppm) was converted to PnAA as demonstrated by the appearance of a new peak at δ 9.9 ppm in the $^{31}P$ NMR spectrum. Upon prolonged storage, PnAA undergoes a non-enzymatic degradation as attested by the appearance of a broad peak at δ 15.4 ppm in the $^{31}P$ NMR spectrum consistent with previously reported behavior. Accordingly, the PEP mutase activity of RhiH-N-His was shown.

RhiH-N-His, together with Ppd-Bf-His, were used for the enzymatic preparation of PnAA. Due to labile nature of PnAA, the enzyme-free reaction mixture was used as a source of PnAA without further purification.

Example 3

RhiG Catalytic Activity

To confirm the function of RhiG, the RhiG-catalyzed reaction was reconstituted in vitro and its product was characterized. The product of RhiG obtained via an enzymatic reaction can be used as the substrate for biochemical investigation of subsequent biosynthetic steps. RhiG was purified as a C-terminal fusion with a hexahistidine tag, RhiG-C-His (MW 38.7 kDa), using metal affinity chromatography. The purified protein contained no chromophore as attested by a UV-vis spectrum transparent above 300 nm. Native RhiG-C-His is a homodimer (native MW 75 kDa) as determined by size-exclusion chromatography.

Figure 6:
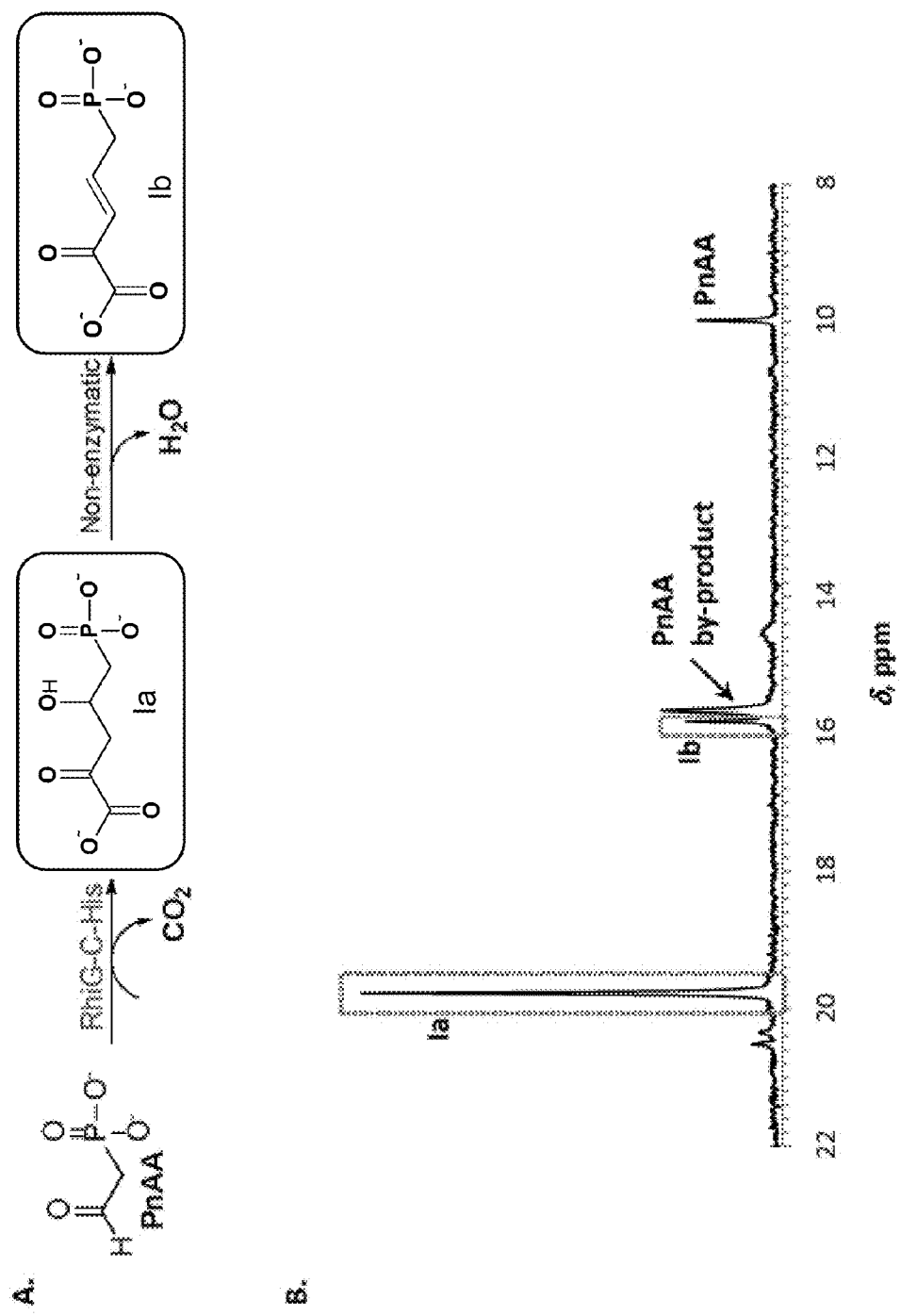
FIG. 6 shows (A) the scheme of the reaction catalyzed by RhiG-C-His, and (B) $^{31}$P NMR spectrum of the RhiG-C-His assay with unlabeled substrates, according to at least one embodiment of the present disclosure.

As seen for other class II aldolases, the activity of RhiG is dependent on a divalent metal cation, such as $Mg^{2+}$ or $Mn^{2+}$. Since the PnAA solution prepared with RhiH-N-His and Ppd-Bf-His already contains $Mg^{2+}$, no additional metals were supplied to the reaction. Incubation of a PnAA solution with pyruvate and RhiG-C-His did not produce new phosphonate compounds when examined by $^{31}P$ NMR spectroscopy. OAA was then evaluated as substrate for the aldol reaction with PnAA. Indeed, incubation of PnAA with OAA and RhiG-C-His resulted in the formation of a new compound, denoted Ia, as demonstrated by the appearance of a new peak (δ 19.8 ppm) in the $^{31}P$ NMR spectrum (FIG. 6B). Approximately 80% of the PnAA was converted to Ia, as estimated by integration of the $^{31}P$ NMR signals. The product Ia was observed only when OAA and RhiG-C-His were both added to the assay. No new phosphonates were detected when 2-ketoglutaric acid was used in place of OAA. Upon storage of the enzyme-free assay mixture, a slow conversion occurred of the phosphonate Ia to another phosphonate-containing compound (δ 15.8 ppm), denoted Ib. Degradation of Ia and its highly polar nature complicated its purification by HPLC. Therefore, the structures of compounds Ia and Ib were determined using spectroscopic analyses of a crude assay mixture.

Figure 7A:
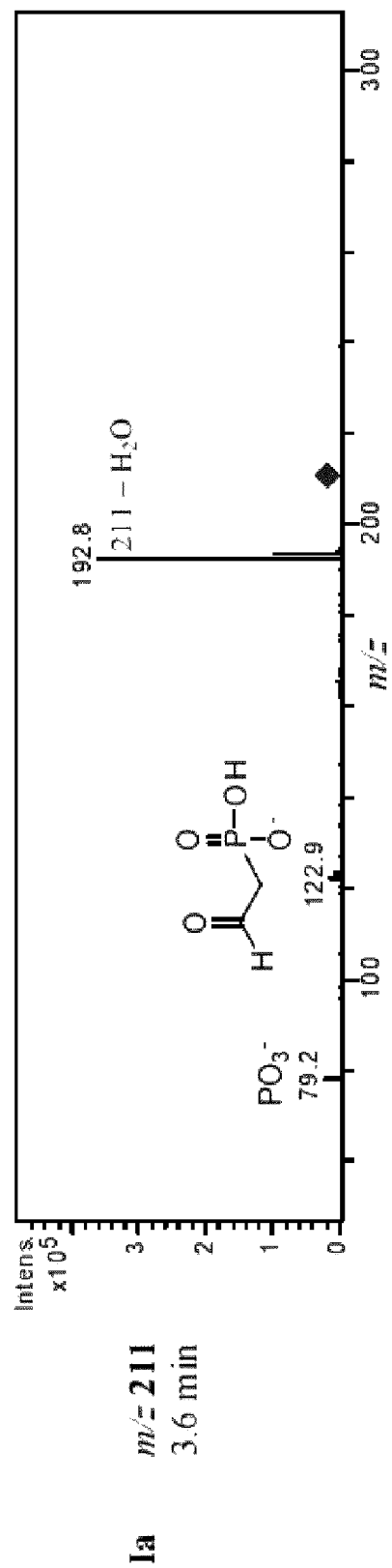
FIG. 7 shows a graphical representation of MS fragmentation data for Ia', Ia', and Ia", according to an embodiment of the present disclosure.
Figure 7B:
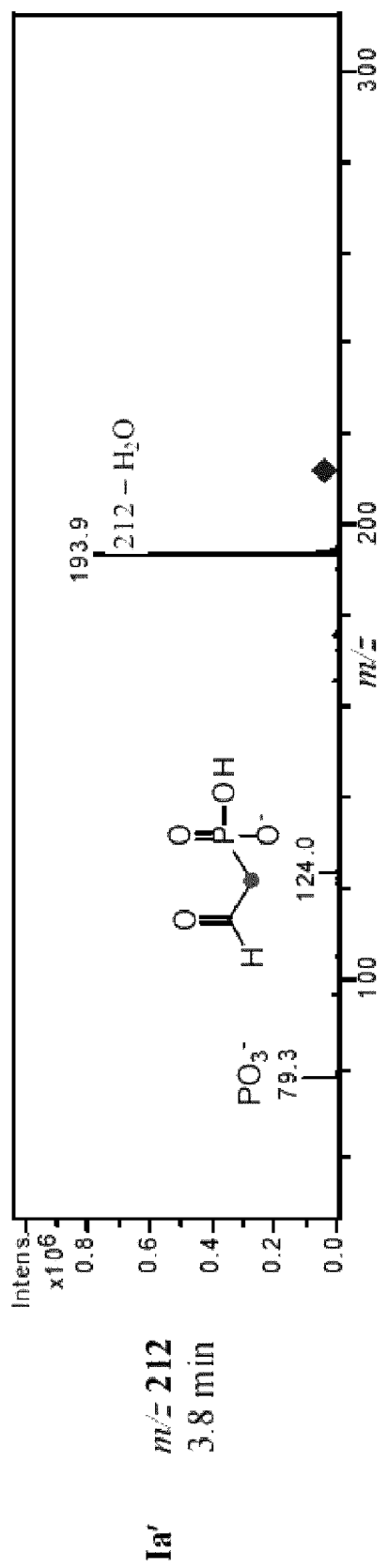
Figure 7C:
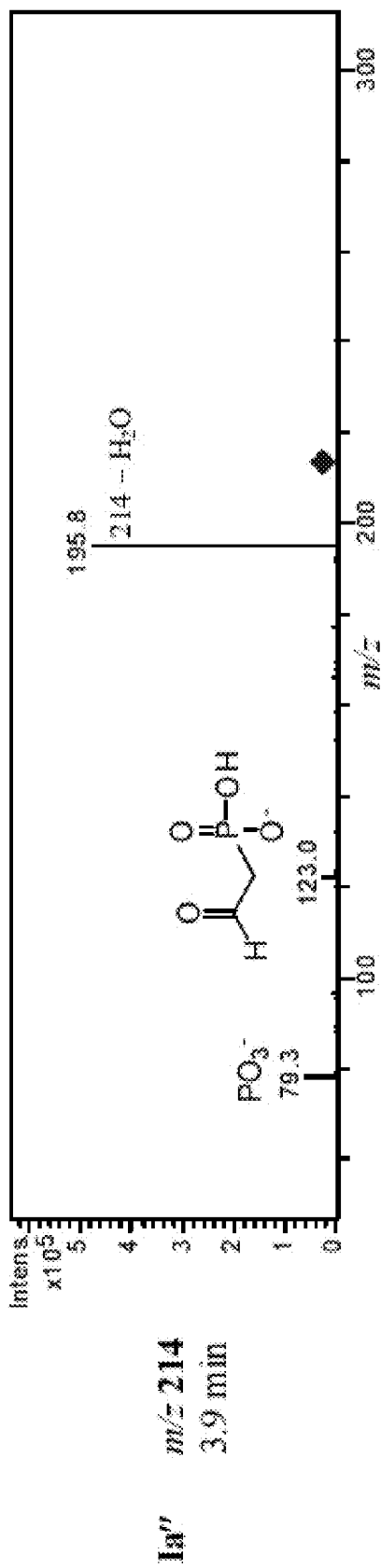
Figure 8:
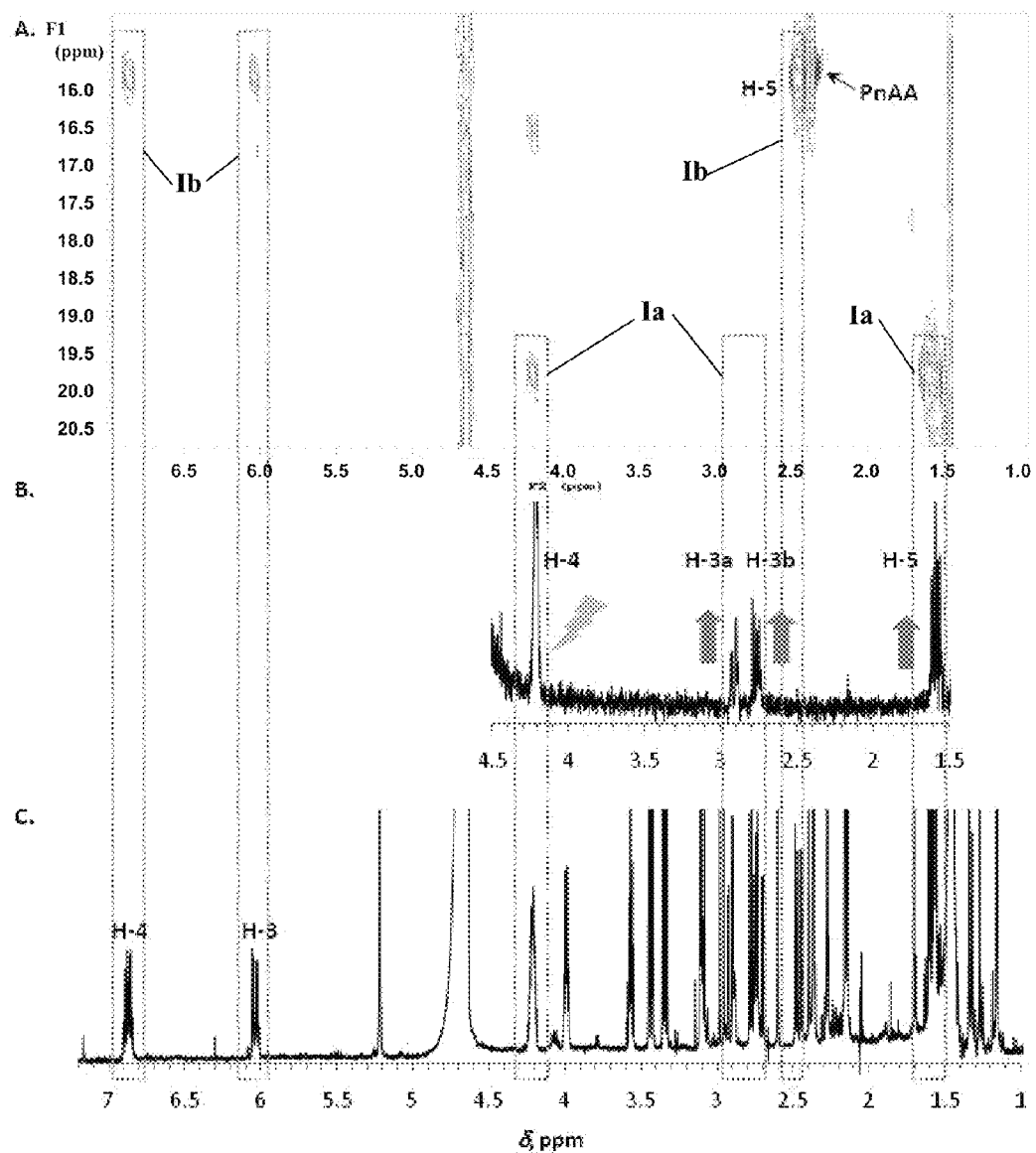
FIG. 8 shows NMR spectroscopic characterization of RhiG-C-His products Ia and Ib, according to at least one embodiment of the present disclosure.
Figure 9:
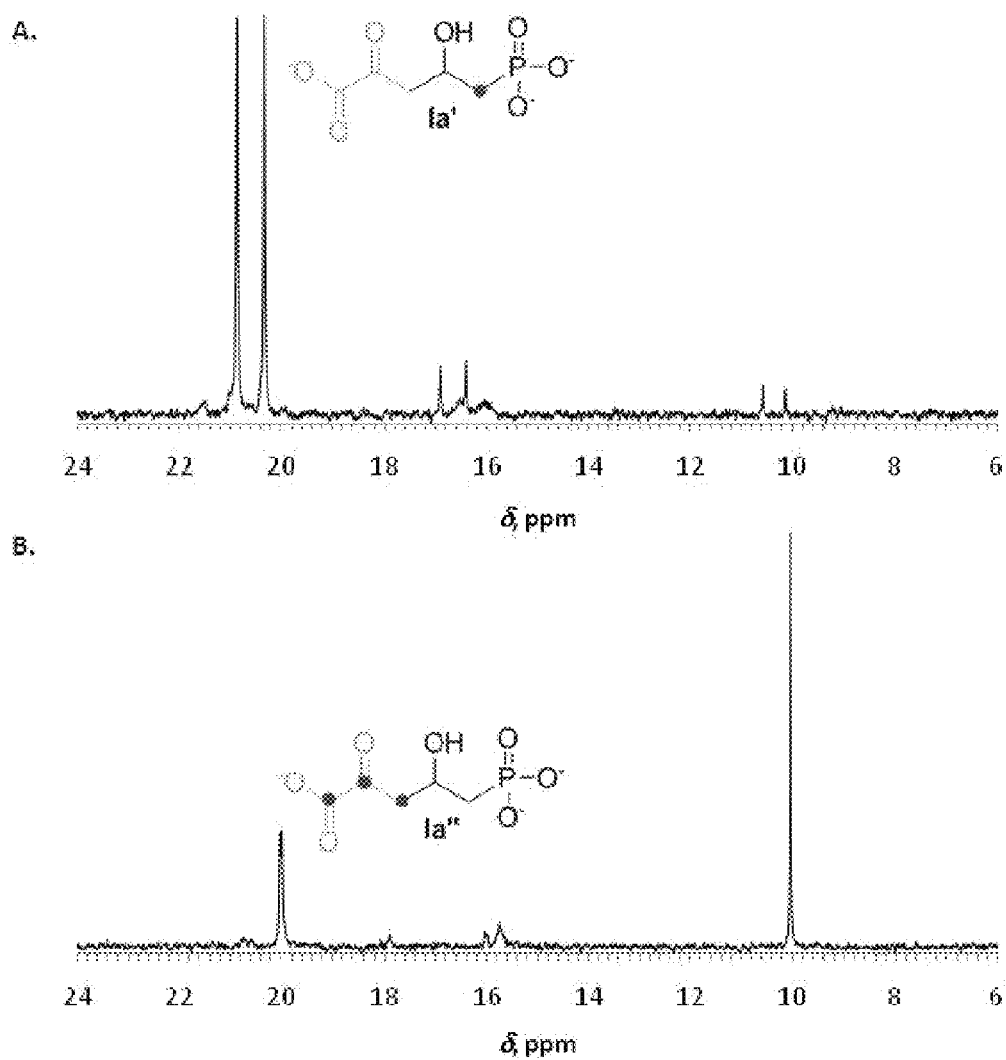
FIG. 9 shows the $^{31}$P NMR spectroscopic characterization of $^{13}$C-labeled analogs of Ia, according to at least one embodiment of the present disclosure.

A comprehensive NMR analysis of the RhiG-C-His reaction mixtures prepared with unlabeled and $^{13}C$-labeled PEP and OAA substrates (FIGS. 8 and 9) allowed for the unequivocal assignment of the structures Ia and Ib (FIG. 6A). The structure of Ia was further supported by LC-MS analysis (FIG. 7). In FIG. 7, parent ion and LC retention time are listed for each compound. Parent ion is denoted with diamond in mass spectrum. The trans configuration of the double bond in Ib, and not a cis double bond as seen in APPA, indicates non-enzymatic formation of Ib with anti-elimination of water from Ia resulting in a trans-isomer.

It has also been established that RhiG-C-His can catalyze the formation of pyruvate from OAA in the absence of PnAA. This conversion was complete after incubation with RhiG-C-His at room temperature for 15 minutes, whereas only 13% of OAA was converted to pyruvate in the absence of enzyme due to non-enzymatic decarboxylation of OAA.

Example 4

Characterization of Compounds Ia, Ib, Ia', Ia" and Ib' by NMR Spectroscopy

First, the presence of the phosphonates was determined using a routine proton-decoupled $^{31}P$ NMR spectroscopy experiment (FIG. 6B). The phosphorus chemical shifts for the phosphonates generally have characteristic values above 10 ppm and are usually in the range from 10 to 40 ppm. The $^1H$ NMR spectra were routinely taken and proton resonances were assigned based on the values of the chemical shifts (δ, ppm) and the coupling constants (J, Hz) for the proton signals, $^1H$-$^1H$ COSY NMR spectra, and with the help of correlation spectroscopy techniques described below. The $^{13}C$ NMR spectra were taken for $^{13}C$ labeled compounds. Cacodylate buffer produced a singlet (δ 1.5) in $^1H$ NMR spectra and a singlet (δ 17.5) in $^{13}C$ NMR spectra.

The phosphorus resonance was correlated to proton signals via gradient two-dimensional heteronuclear correlation $^1H$-$^{31}P$ gHMBC experiments optimized for multiple-bond couplings with $^nJ$=18 Hz. The phosphorus resonance of Ia was correlated to two proton signals (δ 4.2 and 1.6) by a $^1H$-$^{31}P$ gHMBC experiment (FIG. 8A). In FIG. 8A, identification of the protons coupled to the phosphorus of phosphonates Ia and Ib using $^1H$-$^{31}P$ gHMBC experiment is shown. The signals corresponding to Ia and Ib are outlined in dashed boxes (see FIGS. 8A-C). Analysis of the $^1H$ NMR spectrum further established that one of the signals (δ 1.6 ppm) is comprised of two resonances of an ABX system connected to phosphorus (δ 1.60 and 1.54 ppm).

The spin systems connected to the phosphorus were completed using a one-dimensional TOCSY1D experiment with a mixing time of 80 ms. Thus, for Ia, the selective irradiation of the protons H-5b (δ 1.6) or H-4 (δ 4.2) showed that both are coupled to H-3a (δ 2.9), H-3b (δ 2.8), and H-5 (δ 1.6) (FIG. 8B). In FIG. 8B, the resonance indicated with a lightning bolt was irradiated resulting in an increase of the peaks labeled with an arrow.

The signals identified above were related to $^1H$ (FIG. 8C) and $^1H$-$^1H$ COSY NMR spectra (not shown). Two-dimensional heteronuclear correlation NMR experiments $^1H$-$^{13}C$ gHSQC (optimized for $^1J$=140 Hz) and $^1H$-$^{13}C$ gHMBC ($^nJ$=8 Hz) were used to identify the corresponding carbon resonances. However, the signal corresponding to C-5 of Ia was not observed in either $^1H$-$^{13}C$ gHSQC or $^1H$-$^{13}C$ gHMBC spectra, either due to its splitting by the phosphorus nucleus resulting in lower intensity, or because of interference with the cacodylate buffer at δ 1.5 ppm ($^1H$). Also, C-1 of Ia was not identified in the $^1H$-$^{13}C$ gHMBC experiment. To determine the missing carbon chemical shifts for compound Ia, $^{13}C$ labels were incorporated as described above.

Spectral Data for Ia $^{31}P$ NMR (20% $D_2O$, 242.9 MHz, $^1H$ decoupled) δ (ppm): 19.8 (s); $^{31}P$ NMR (20% $D_2O$, 242.9 MHz, $^1H$ coupled) δ (ppm): 19.8 (m)

| Position | $^{13}C$ δ, ppm$^a$ | $^1H$ δ, ppm | Multiplicity and coupling constants |
|---|---|---|---|
| 1 | ND$^b$ | — | — |
| 2 | 204.2 | — | — |
| 3a | 47.2 | 2.91 | dd, $^3J_{H2-H3a}$ = 3.6 Hz, $^2J_{H3a-H3b}$ = 17.4 Hz |
| 3b | 47.2 | 2.77 | dd, $^3J_{H2-H3b}$ = 8.4 Hz, $^2J_{H3a-H3b}$ = 17.4 Hz |
| 4 | 64.0 | 4.21 | m |
| 5a | ND | 1.60 | ddd$^c$, $^3J_{H4-H5a}$ = 7.8 Hz, $^2J_{H5a-H5b}$ = 14.4 Hz, $^2J_{H5a-P}$ = 15.0 Hz |
| 5b | ND | 1.54 | ddd$^c$, $^3J_{H4-H5b}$ = 5.4 Hz, $^2J_{H5a-H5b}$ = 14.4 Hz, $^2J_{H5b-P}$ = 16.8 Hz |

$^a$Determined from $^1H$-$^{13}C$ gHSQC and or $^1H$-$^{13}C$ gHMBC experiments.
$^b$Not determined.
$^c$Coupling constant for H-5a and H-5b were determined in HEPES-buffered assay, and were supported by simulation using WINDNMR software.

Spectral Data for Ia' (5-$^{13}C$-2-keto-4-hydroxy-5-phosphonopentanoic acid)

The proton-decoupled $^{31}P$ NMR spectrum of the reaction mixture prepared using 3-$^{13}C$-PEP contained sets of doublets replacing previously observed singlets for Ia' and Ib' (FIG. 9A), indicating an incorporation of $^{13}C$ at the C-5 position.

The corresponding C-5 signals for Ia' and Ib' were now easily identifiable in the $^{13}$C NMR spectrum. $^1$H decoupled $^{31}$P and $^{13}$C NMR spectra were collected.

| Position | δ, ppm | Multiplicity and coupling constants |
|---|---|---|
| C-5 | 35.9 | d, $^1J_{C5\text{-}P}$ = 129 Hz |
| P | 20.6 | d, $^1J_{C5\text{-}P}$ = 129 Hz |

Spectral Data for Ia" (1,2,3-$^{13}$C$_3$-2-keto-4-hydroxy-5-phosphonopentanoic acid)

The proton-decoupled $^{31}$P NMR spectrum of the reaction mixture prepared using U-$^{13}$C$_4$-Asp contained a doublet at δ 20.0 ppm confirming the formation of labeled Ia" albeit in reduced yield (approximately 30% from PnAA, FIG. 9B). The major labeled component was pyruvate, which could be generated from OAA via spontaneous decarboxylation. The signal corresponding to the labeled bicarbonate was also present. The second major labeled component was Ia" with $^{13}$C resonances matching those determined from $^1$H-$^{13}$C gHSQC and $^1$H-$^{13}$C gHMBC experiments. Additionally, a signal for C-1 was identified. $^1$H decoupled $^{31}$P and $^{13}$C NMR spectra were collected.

| Position | δ, ppm | Multiplicity and coupling constants |
|---|---|---|
| C-1 | 169.6 | dd, $^2J_{C1\text{-}C3}$ = 12 Hz, $^1J_{C1\text{-}C2}$ = 62 Hz |
| C-2 | 204.0 | dd, $^1J_{C2\text{-}C3}$ = 39 Hz, $^1J_{C1\text{-}C2}$ = 62 Hz |
| C-3 | 47.2 | ddd, $^3J_{C3\text{-}P}$ = 10.7 Hz, $^2J_{C1\text{-}C3}$ = 12 Hz, $^1J_{C2\text{-}C3}$ = 39 Hz |
| P | 20.0 | d, $^3J_{C3\text{-}P}$ = 10.4 Hz |

Spectral Data for Ib

The phosphorus resonance of the breakdown product Ib was correlated to three proton signals (δ 6.87, 6.04, and 2.46 ppm, FIG. 8A). TOCSY1D spectra obtained by the selective irradiation of the proton H-4 (δ 6.9) revealed the couplings to H-3 (δ 6.0) and H-5 (δ 2.5) (data not shown). Additional NMR data from $^1$H, $^1$H-$^1$H COSY, $^1$H-$^{13}$C gHSQC, and $^1$H-$^{13}$C gHMBC experiments confirmed the structure of compound Ib as that shown in FIG. 6A.

$^{31}$P NMR (20% D$_2$O, 242.9 MHz, $^1$H decoupled) δ (ppm): 15.8 (s); $^{31}$P NMR (20% D$_2$O, 242.9 MHz, $^1$H coupled) δ (ppm): 15.8 (t, ~20 Hz))

| Position | $^{13}$C δ, ppm[a] | $^1$H δ, ppm | Multiplicity and coupling constants |
|---|---|---|---|
| 1 | 173 | — | — |
| 2 | 197 | — | — |
| 3 | 128 | 6.04 | dd, $^4J_{H3\text{-}P}$ = 4.2 Hz, $^3J_{H3\text{-}H4}$ = 15.6 Hz |
| 4 | 152.5 | 6.87 | dtd, $^3J_{H4\text{-}P}$ = 6.0 Hz, $^3J_{H4\text{-}H5}$ = 8.4 Hz, $^3J_{H3\text{-}H4}$ = 15.6 Hz |
| 5a, 5b | 36 | 2.46 | dd, $^3J_{H4\text{-}H5}$ = 8.4 Hz, $^2J_{H5\text{-}P}$ = 21.6 Hz |

[a]Determined from $^1$H-$^{13}$C gHSQC and or $^1$H-$^{13}$C gHMBC experiments.

Spectral Data for Ib' (5-$^{13}$C-2-keto-4-hydroxy-5-phosphono-3-pentenoic acid)

$^1$H decoupled $^{31}$P and $^{13}$C NMR spectra were collected.

| Position | δ, ppm | Multiplicity and coupling constants |
|---|---|---|
| C-5 | 35.4 | d, $^1J_{C5\text{-}P}$ = 121 Hz |
| P | 16.7 | d, $^1J_{C5\text{-}P}$ = 121 Hz |

Mass Spectroscopy Fragmentation Data for Ia, Ia, and Ia".

LC-MS analysis of RhiG-C-His reaction mixtures was performed using Agilent LC/MSD Trap XCT Plus instrument with ESI in negative mode. Compounds were eluted from Synergi 4 μm Fusion-RP HPLC column (4.6×100 mm, Phenomenex, Inc., Torrance, Calif.) with 10% acetonitrile in 15 mM ammonium formate at 0.3 mL/min. Compounds Ia, Ia', and Ia" eluted at 3.6, 3.8, and 3.9 min respectively. Observed MSn spectra for Ia, Ia', and Ia" and fragment assignments are shown in FIG. 7.

Example 5

The RhiG Reaction

Figure 10:
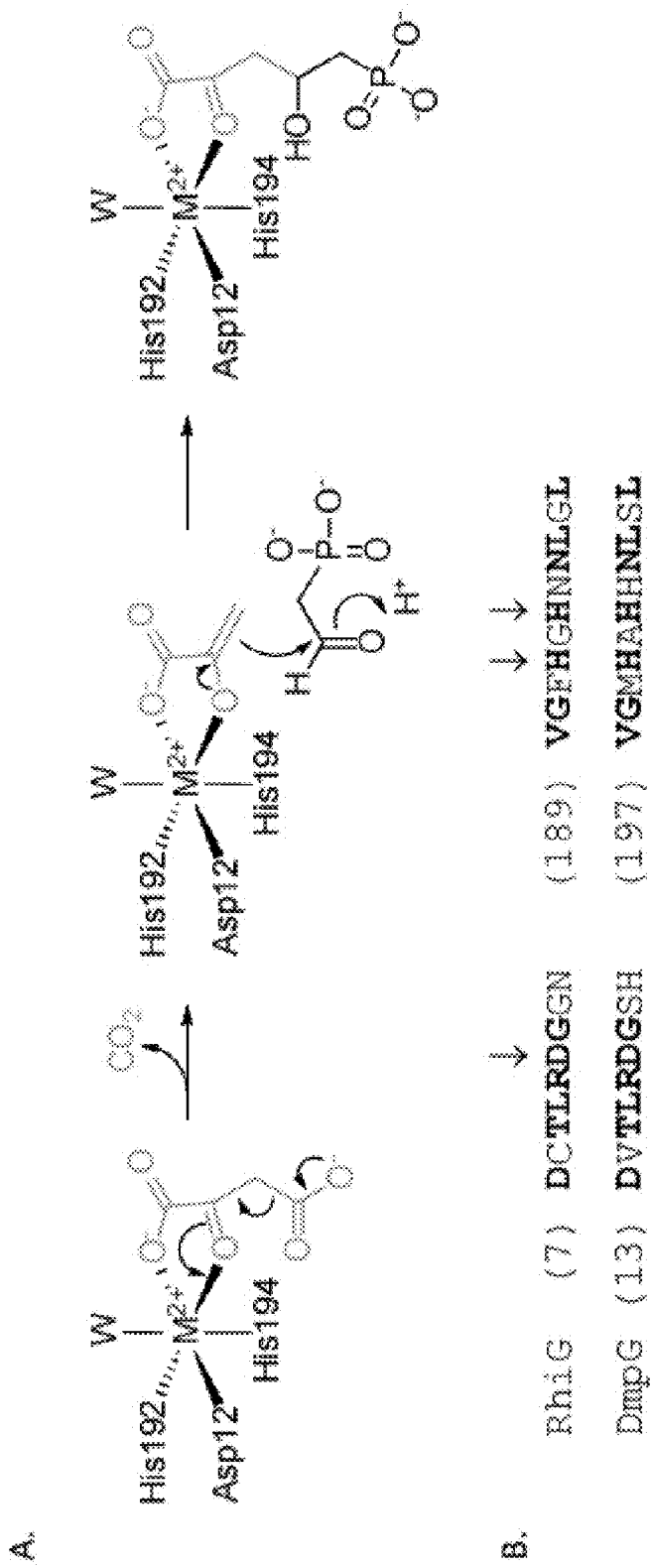
FIG. 10 shows the mechanism for the RhiG catalyzed transformation according to at least one embodiment of the present disclosure.

RhiG catalyzes the formation of 2-keto-4-hydroxy-5-phosphonopentanoic acid from PnAA and OAA. OAA serves as a surrogate of pyruvate and the corresponding three-carbon moiety is incorporated into the final product. OAA coordinates to a divalent metal cation (Mg$^{2+}$ in our assay) via its 1-carboxylate and 2-ketone moieties and undergoes decarboxylation to produce the enolate form of pyruvate. The enolate is stabilized by the divalent cation acting as an electron sink. Subsequent attack of the enolate on the electrophilic carbonyl moiety of PnAA furnishes the carbon-carbon bond of I (FIG. 10A). In FIG. 10, amino acid residues coordinating divalent metal cation (panel A, RhiG numbering, W denotes water) are based on the alignment with the homolog DmpG shown in panel B (conserved residues are in bold, ligands to M$^{2+}$ are labeled with arrows).

The RhiG mechanism is supported by the homology of RhiG to 4-hydroxy-2-oxovalerate aldolase DmpG. Particularly, the residues comprising Mn$^{2+}$ ligands in DmpG are also conserved in RhiG (FIG. 10B). A crystal structure of DmpG contains either pyruvate (a product) or oxalate (a structural analog of pyruvate enolate) as an equatorial bidentate ligand to Mn$^{2+}$. An analogous position could be occupied by OAA in RhiG as depicted in FIG. 10A.

The first step in this mechanistic model, decarboxylation of OAA, is analogous to that catalyzed by macrophomate synthase from the fungus *Macrophoma commelinae*. The pyruvate enolate generated by macrophomate synthase is stabilized by coordination to Mg$^{2-}$ and carries out either a Diels-Alder or Michael-type aldol reaction.

Example 6

Heterologous Production of Rhizocticin B

Figure 11:
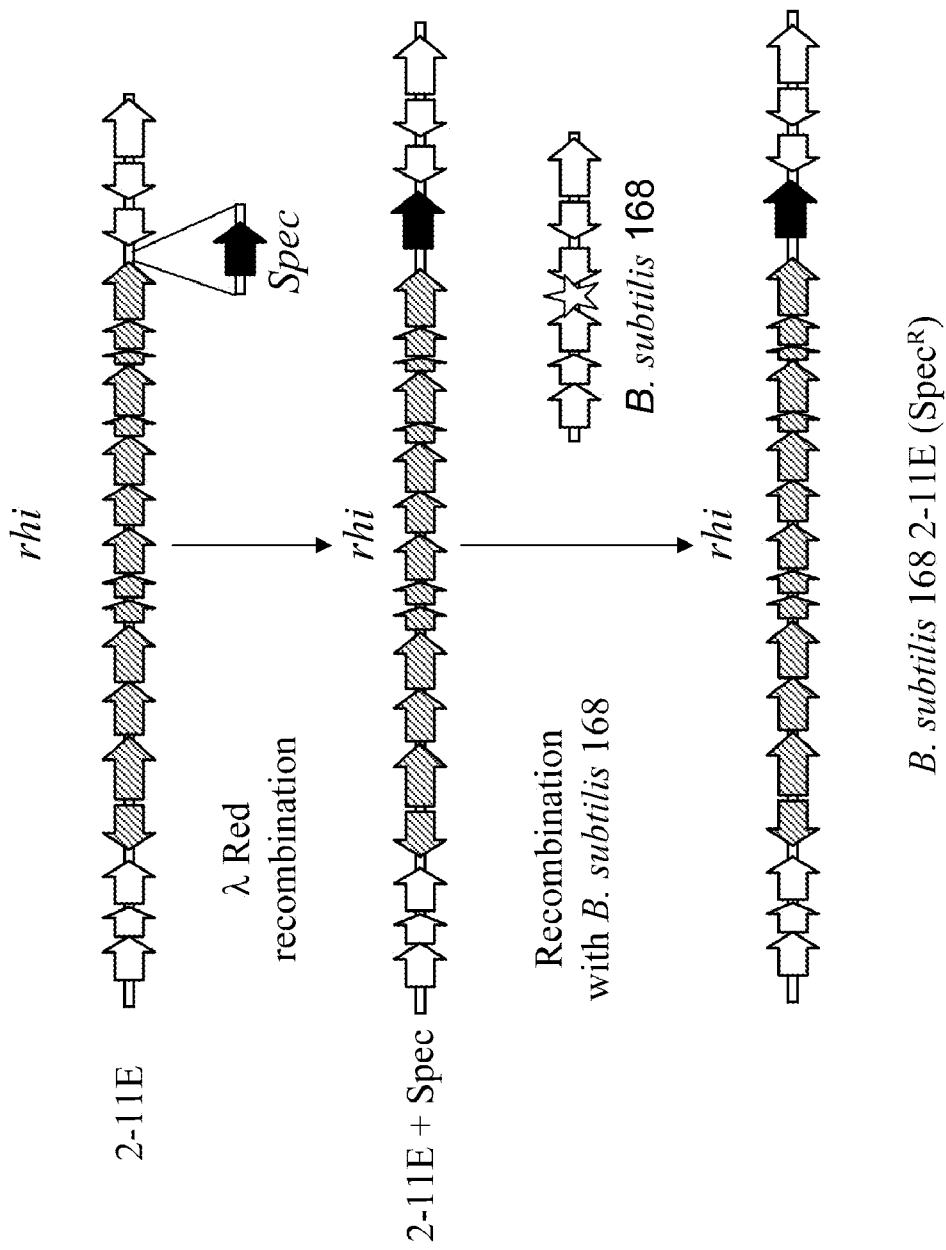
FIG. 11 shows an outline of the experimental design for the preparation of the rhizocticin heterologous producer *B. subtilis* MMG272, according to at least one embodiment of the present disclosure.

To confirm that the identified gene cluster is responsible for the biosynthesis of rhizocticins in *B. subtilis* ATCC6633, the rhi cluster was introduced in the *B. subtilis* 168 genome through homologous recombination (see Methods and FIG. 11 for details). To do this, a spectinomycin resistance cassette (Spec) was introduced into fosmid 2-11E downstream of the rhi cluster using λ Red recombinase-mediated recombination. The resulting fosmid 2-11E+Spec was linearized by restriction digestion and used for the transformation of *B. subtilis* 168. The level of homology between the DNA sequence immediately outside of the rhi cluster in *B. subtilis* ATCC6633 and the corresponding sequence of *B. subtilis* 168 (over 90% identity on the nucleotide level) was sufficiently high for the homologous recombination to occur. The resulting recombinant *B. subtilis* 168 colonies selected on spectinomycin-containing medium contained the rhi cluster as verified by PCR amplification of rhiC and rhiM genes.

Figure 12A:
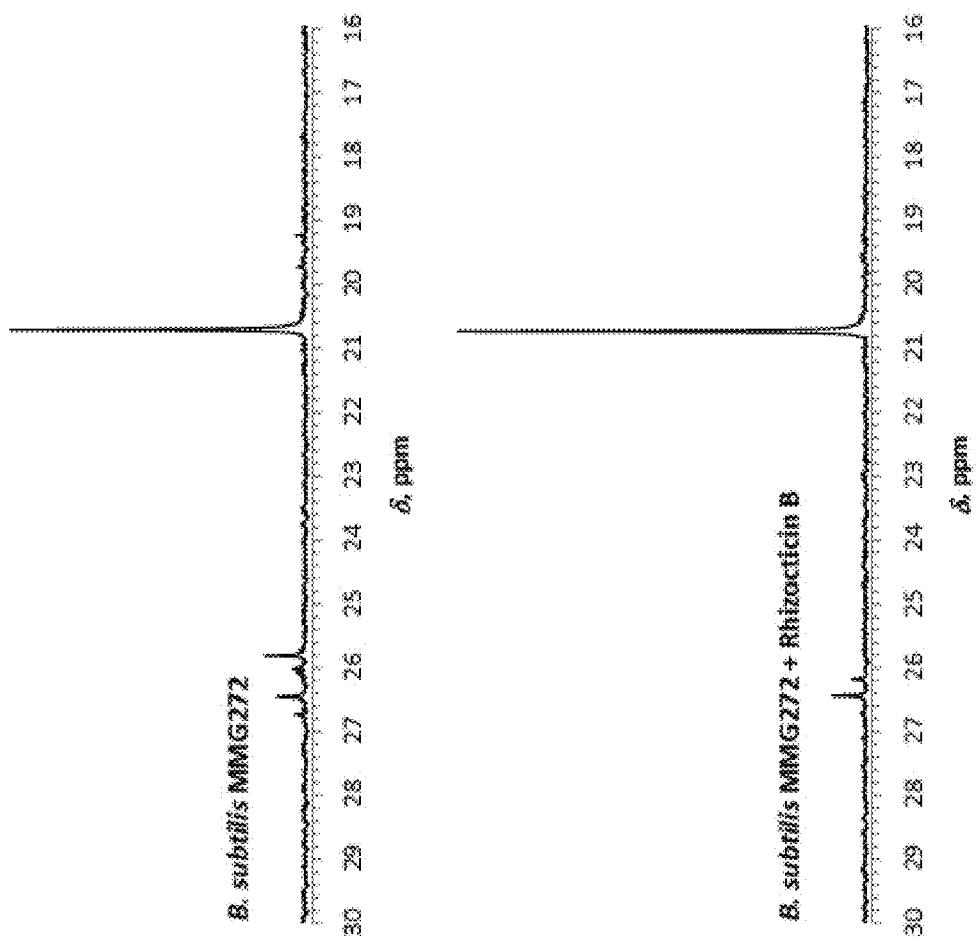
FIG. 12 shows the analysis of rhizocticin B production by *B. subtilis* MMG272 through (A) $^{31}$P NMR spectra, and (B) LC-MS analysis of partially purified spent medium of *B. subtilis* MMG272, according to at least one embodiment of the present disclosure.
Figure 12B:
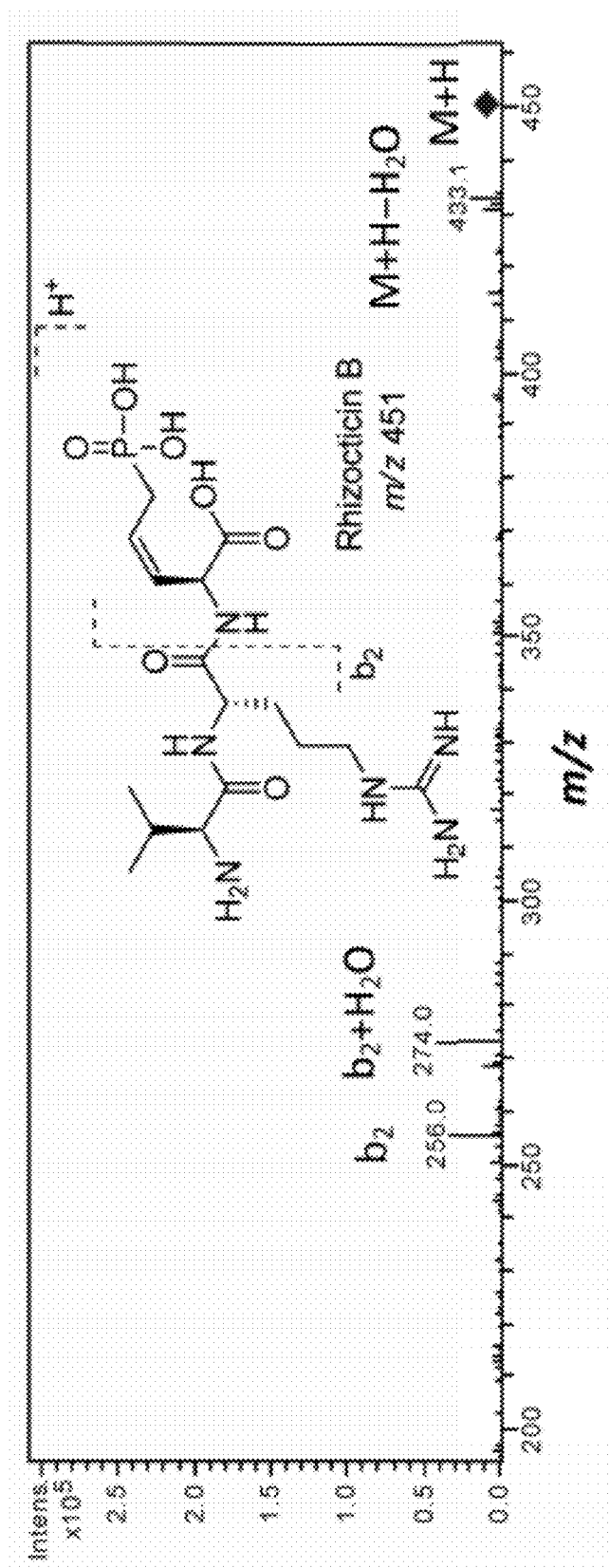

One of the recombinant strains, *B. subtilis* MMG272, was grown for the production of rhizocticins, and its clarified spent medium was partially purified and fractionated as described in the Methods. Samples were analyzed by phosphorus ($^{31}$P) NMR spectroscopy for the presence of phosphonates. One of the fractions produced a major phosphonate peak with a characteristic chemical shift (δ) of 20.7 ppm in the $^{31}$P NMR spectrum (FIG. 12). Addition of purified rhizocticin B to the sample resulted in an increase in intensity of the δ 20.7 ppm peak and no new peaks in the $^{31}$P NMR spectrum (FIG. 12A), indicating that the major phosphonate product is rhizocticin B. The concentrations of components in the sample *B. subtilis* MMG272+rhizocticin B are the same as in the individual sample of *B. subtilis* MMG272. Both spectra were collected for 400 transients and adjusted to the same absolute vertical scale. Analysis of the sample by liquid chromatography-mass spectrometry (LC-MS) further supported the presence of rhizocticin B (see FIG. 12B and Methods for details). The fragmentation of the rhizocticin B parent ion is shown and the peaks corresponding to the characteristic fragments are labeled. No phosphonates were produced in a control experiment with the parent *B. subtilis* 168 strain (data not shown). Taken together, these results confirm that *B. subtilis* MMG272 produces rhizocticin B and that the rhi gene cluster is responsible for its biosynthesis.

While various embodiments' compositions and methods for the production of APPA-containing peptides have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the spirit and scope of the present disclosure.

Methods

The bacteria and oligonucleotides used herein are listed in Tables 2 and 3, respectively, below.

TABLE 2

Microorganisms and plasmids used in this work

| Strain or plasmid | Relevant characteristics | Source or reference |
|---|---|---|
| *Escherichia coli* | | |
| WM4489 | *E. coli* DH10B derivative: mcrA Δ(mrr hsdRMS mcrBC) φ80(ΔlacM15) ΔlacX74 endA1 recA1 deoR Δ(ara-leu)7697 araD139 galU galK nupG rpsL λattB::pAE12(PrhaB::trfA33 ΔoriR6K-cat::frt5) | (Eliot et al., 2008) |
| DH5 α λpir | λpir/φ80dlacZΔM15 Δ(lacZYA-argF)U169 recA1 hsdR17 deoR thi-1 supE44 gyrA96 relA1 | (Grant et al., 1990) |
| MMG194 | Derivative of WM4489 containing 2-11E fosmid | This work |
| MMG273 | Derivative of WM4489 containing 2-11E+Spec fosmid | This work |
| BL21(DE3) | F$^-$ ompT gal dcm lon hsdS$_B$(r$_B^-$ m$_B^-$) λ(DE3 [lacI lacUV5-T7 gene 1 ind1 sam7 nin5]) | Novagen |
| *Bacillus subtilis* | | |
| ATCC6633 168 | Wild type rhizocticin producer | ATCC$^a$ University of Illinois Culture Collection |
| MMG272 | *B. subtilis* 168 containing rhi cluster | This work |
| Plasmids | | |
| pJK050 | oriV, oriS, copy-control cosvector, Cm$^R$ | (Eliot et al., 2008) |
| pAE5 | Source of mini-Mu transposon | (Eliot et al., 2008) |
| fosmid 2-11E | *B. subtilis* 6633 genomic DNA cloned into pJK050; contains rhizocticin biosynthesis genes | This work |
| pAIN750 | Source of spectinomycin resistance cassette (Spec) | (Guerout-Fleury et al., 1996)$^b$ |
| pKD46 | λ Red recombinase expression plasmid | (Datsenko and Wanner, 2000) |
| 2-11E+Spec | Derivative of fosmid 2-11E with Spec inserted downstream of rhi cluster | This work |
| pET26b | Kan$^R$ *E. coli* T7 based histidine-tag fusion expression vector | Novagen |
| pET28a | Kan$^R$ *E. coli* T7 based histidine-tag fusion expression vector | Novagen |
| pRhiG-C-His | rhiG cloned in pET26b vector | This work |
| pRhiH-N-His | rhiH cloned in pET28a vector | This work |
| pPpd-Bf-His | ppd of Bacteroides fragilis cloned in pET24a vector | H. Zhao, UIUC |

$^a$ATCC, American Type Culture Collection, Manassas, VA.

TABLE 3

Oligonucleotides used in this study

| Oligonucleotide | DNA sequence$^a$ |
|---|---|
| CHIpepmutF1 | CGCCGGCGTCTGCNTNGARGAYAA |
| CHIpepmutR2 | GGCGCGCATCATGTGRTTNGCVYA |
| seqAETnR | TAGGAACTTCGGGATCCGTT |

TABLE 3-continued

Oligonucleotides used in this study

| Oligonucleotide | DNA sequence[a] |
|---|---|
| seqAETnL | TCGCCTTCTTGACGAGTTCT |
| Bs-screen-A1 | TATGGAAAGTCCTAAAAGTC |
| Bs-screen-A2 | TTATACGTGACATACTGCTG |
| Bs-screen-C1 | GCTCCTATTTTGGGATAGCCGGGCC |
| Bs-screen-C2 | CCGGGACCGTCTGTGATACGAAACG |
| Spec-red-fwd2 | TGTTCATATGTTTTAGGGCTTCACTTGAATGTAGCTGTTGTCTAAGAGAT<br>GTCGTTCGTGAATACATGTT[b] |
| Spec-red-rev2 | GTAGCTGCGGTAATGCCGGTGTCTGCGATAGCGATCACTCGAGCTGCTTG<br>AGCAAGGGTTTATTGTTTTC[b] |
| ORF7-fwd-Nde | GCGCCATATGAAAATGCAATTAATAG[c] |
| ORF7-rev-Hind-C-His | GCCGAAGCTTTGCACTCTCCTGTCTAAA[c] |
| rhiH-fwd-Nde | GGCGCGCCCATATGAAAGCTAAAAAATTACG[c] |
| rhiH-rev-Hind-stop | GGCGCGCCAAGCTTATTTGATAGTACTGATG[c] |

[a]Standard abbreviations are used: R = A or G, Y = C or T, and V = A or C or G.
[b]Sequences homologous to 2-11E are underlined.
[c]NdeI and HindIII sites are underlined.

454 Sequencing of *B. subtilis* ATCC6633 Genome

The genomic DNA of *B. subtilis* ATCC6633 was subjected to high-throughput sequencing using the Roche 454 GS-FLX system. A total of 677,801 reads with an average read length of 196 bases per read provided ~30× coverage of the genome. The sequence reads were assembled into 37 contigs totaling 3,978,576 base pairs using 454 Newbler Assembler.

Construction and Screening of *B. subtilis* 6633 Genomic Library

Approximately 5 μg of *B. subtilis* 6633 genomic DNA was partially digested with Sau3AI (New England Biolabs, Ipswich, Mass.) to yield fragments of ~30-50 kb, which were then treated with shrimp alkaline phosphatase (Roche Diagnostics, Indianapolis, Ind.) and ligated into BamHI- and NheI-digested pJK050. This vector was treated with shrimp alkaline phosphatase between the NheI and BamHI digests to prevent formation of vector concatamers. The ligated DNA was purified by ethanol precipitation and packaged into lambda phage using the MaxPlax packaging extract (Epicentre, Madison, Wis.) according to the manufacturer's instructions. *E. coli* WM4489 cells were transfected with the packaged library and plated on LB agar+12 μg/mL Cm.

A fraction of the *E. coli* fosmid library (960 clones) was screened by PCR for clones containing the PEP mutase gene sequence. Each reaction consisted of 1 μL culture broth, 500 nM of each primer (CHIpepmutF1 and CHIpepmutR2), and Taq polymerase in Failsafe buffer J (Epicentre, Madison, Wis.), and the annealing temperature was 52° C. No positive clones were detected using this set of primers even with various PCR conditions tested.

Two sets of sequence-specific primers were used to screen the genomic library. Primers Bs-screen-A1 and Bs-screen-A2 amplify a 517 bp sequence of orf6 and primers Bs-screen-C1 and Bs-screen-C2 amplify a 520 bp sequence within rhiM. Fosmid 2-11E produced expected PCR fragments with both sets of primers. Fosmid DNA was isolated from the positive clone (MMG 194) grown overnight in 100 mL LB+12 μg/mL Cm+15 mM rhamnose using a Qiagen Maxiprep kit (Qiagen Inc., Valencia, Calif.) and sequenced using transposon mutagenesis as described below.

Sanger Sequencing of Fosmid 2-11E

A library of transposon insertions was generated using the mini-Mu transposon encoded in pAE5. Transposition reactions of BglII-digested pAE5 (mini-MuAE5 transposon) and fosmid 2-11E (target DNA) were conducted in vitro using MuA transposase (MJ Research, Waltham, Mass.) according to the manufacturer's instructions. *E. coli* WM4489 was transformed with the reaction products, and successful insertions were selected on LB+25 μg/mL Kan. Fosmid DNA was isolated from 192 colonies that were individually picked into 2 mL LB+20 mM rhamnose+12 μg/mL Cm+25 μg/mL Kan and incubated overnight at 37° C. (in 96-well plate format). The fosmid DNA was sequenced using the primers seqA-ETnR and seqAETnL. The sequence was assembled using Sequencher (Gene Codes Corp., Ann Arbor, Mich.) and the remaining gaps were filled in by obtaining further sequence using specifically designed primers. The sequence of the insert in fosmid 2-11E containing rhizocticin biosynthetic gene cluster has been deposited in GenBank under accession number FJ935779, which is incorporated herein by reference.

NMR Spectroscopy Instrumentation.

The presence of phosphonates was detected using $^1$H decoupled $^{31}$P NMR spectroscopy. All of the spectra were collected in $H_2O$ supplemented with 20% $D_2O$ as a lock solvent. The $^{31}$P NMR spectra were externally referenced to an 85% phosphoric acid standard (0 ppm). Spectra were acquired at room temperature on a Varian Unitiy Inova-600 spectrometer. The spectrometer was equipped with a 5-mm Varian 600DB AutoX probe with ProTune accessory for the collection of the $^{31}$P, $^1$H-$^{31}$P gHMBC, and $^{13}$C spectra. The probe was tuned for either phosphorus at 242.789 MHz or carbon at 150.828 MHz. The $^1$H, TOCSY1D, gCOSY, $^1$H-$^{13}$C gHSQC, and $^1$H-$^{13}$C gHMBC spectra were acquired on the same instrument but using a 5-mm Varian $^1$H{$^{13}$C/$^{15}$N}XYZ PFG triple resonance probe tuned to proton at 599.764 MHz.

Preparation of Rhizocticin Heterologous Producer *B. subtilis* MMG272.

The spectinomycin cassette was incorporated into 2-11E fosmid using λ Red mediated recombination with modifications as described below. A spectinomycin resistance cassette was amplified by PCR using primers Spec-red-fwd2 and Spec-red-rev2 using pAIN750 as a template. The primers were designed to contain 51 bp regions of homology to the sequences flanking the site of Spec insertion in fosmid 2-11E. The PCR product (Spec fragment, 1247 nt) was digested with DpnI and purified from an agarose gel. Electrocompetent *E. coli* MMG194 was transformed with pKD46, plated on LB agar containing 12 µg/mL chloramphenicol (Cm) and 100 µg/mL ampicillin (Amp), and grown at 30° C. overnight. One of the transformants was picked and grown overnight at 30° C. in LB-Cm, Amp. The culture was then diluted 100-fold into SOB medium containing Cm, Amp, and 2 mM arabinose (to induce λ recombinase) and grown to $OD_{600}$~0.6 at 30° C. The cells were made electrocompetent by extensive washing with ice-cold 10% glycerol and concentrated 100-fold. These cells (50 µL aliquot) were transformed with the PCR fragment (35 ng) via electroporation, recovered in SOC medium at 37° C. for 2 h, and plated on LB agar containing 7 µg/mL Cm and 100 µg/mL spectinomycin (Spec). Several colonies were inoculated into LB-Cm, Spec and grown overnight at 37° C. The fosmid DNA was isolated using QIAprep kit and analyzed by PCR amplification of the rhiC, rhiM genes and Spec fragment. The amplification of the DNA fragments of the desired size confirmed the incorporation of Spec into 2-11E and formation of fosmid 2-11E+Spec.

The fosmid DNA 2-11E+Spec was used to transform *E. coli* WM4489 to yield *E. coli* MMG273 strain. This strain was grown in the presence of 10 mM rhamnose to induce a high copy number for the fosmid 2-11E+Spec and the fosmid DNA was re-isolated. The 2-11E+Spec DNA was digested by restriction endonuclease NotI, purified by ethanol precipitation, and used to transform *B. subtilis* 168 following a published protocol (Henner, Methods Enzymol. 185, 223-228; 1990). Recombinants were selected on LB agar plates containing 100 µg/mL Spec. The recombination was confirmed by culture PCR of selected recombinant strains as described above for verification of the fosmid 2-11E+Spec. One of the strains, *B. subtilis* MMG272, was chosen for rhizocticin production analysis as described below.

Rhizocticin B Purification from *B. subtilis* 6633.

Published protocols for the production and purification of rhizocticins were followed with minor modifications as described below (Kugler et al., Arch. Microbiol. 153, 276-281, 1990; Rapp et al., Liebigs Ann. Chem., 655-661, 1988). *B. subtilis* 6633 was cultured at 30° C. on nHA plates (Kugler, et al., 1990) (10 cm diameter) for 3 days. The cells were scraped from the surface, re-suspended in sterile water and 0.5 mL of the resulting suspension was used to inoculate 100 mL of LB media. The cells were incubated with shaking at 30° C. for 11 days and the entire starter culture was used to inoculate 10 L of PL media (Kugler, et al., 1990) in a BIOFLO 110 fermentor (New Brunswick Scientific, Edison, N.J.). The PL culture was incubated with stirring (300 rpm) and aeration (5 L/min air) at 60° C. for 3 h followed by incubation at 30° C. for 3 days. The culture was brought to pH 2.5 using 6 M HCl and the supernatant was clarified by centrifugation.

Cell-free supernatant was reduced to 100 mL by evaporation under reduced pressure and lyophilized to dryness. The yellowish solids were re-suspended in 300 mL of 70% ethanol and incubated at 4° C. overnight. The precipitate was filtered, the filtrate was evaporated to dryness, and the solid residue was dissolved in 300 mL of water and incubated with 30 mL of Amberlite XAD-16 resin. Upon removal of Amberlite XAD-16, the supernatant was reduced to 30 mL and the formed precipitate was removed by centrifugation. This crude supernatant was analyzed by $^{31}P$ NMR spectroscopy at this point, however, the identification of the phosphorus-containing components was impossible due to extreme peak broadening ($W_{1/2}$~2000 Hz for phosphate ester signals) and low signal-to-noise level in the NMR spectra presumably resulting from the high salt concentration. The crude sample was therefore subjected to further column purification using Biogel P2.

Aliquots of 4 mL of the crude sample were applied onto a size-exclusion Biogel P2 column (1.5×100 cm, equilibrated with water), compounds were eluted with water at 0.15 mL/min, and 10-mL fractions were collected and analyzed by LC-MS for the presence of rhizocticins A-D. LC-MS was performed on an Agilent 1200 series quad pump system equipped with a diode array detector (DAD) and a mass spectrometer with a multimode-electrospray/atmospheric pressure chemical ionization (MM-ES+APCI) source. Small portions of P2 fractions (20-80 µL) were injected onto a ZIC®-pHILIC HPLC column (5 µm, 2.1×150 mm, Merck SeQuant AB, Umeå, Sweden) and eluted isocratically with 30% 20 mM ammonium acetate/70% acetonitrile at 0.3 mL/min. The DAD was set to detect the absorbance at 220 nm and MS detector was set to ESI in positive mode. A 7.7 min peak with absorbance at 220 nm and producing a m/z 451 ion was attributed to rhizocticin B (exact molecular mass 450.1992). Two additional peaks eluting at 7.1 and 8.4 min had lower intensity at 220 nm and produced m/z 465 ion, suggesting that they might contain minor amounts of rhizocticins C and D (estimated less than 10% of the rhizocticin B present). No rhizocticin A was detected in the fractions. P2 fractions were pooled based on the presence of rhizocticin B signal (via LC-MS analysis), evaporated to dryness, dissolved in 20% $D_2O$ and analyzed by $^{31}P$ NMR spectroscopy. The phosphonate signal at 20.7 ppm was produced by P2 fractions eluting between 80 and 110 mL. The $^1H$ NMR spectra of this sample was compared to that previously published for rhizocticin B and APPA (Fredenhagen et al., 1995; Rapp et al., 1988). It contained several peaks assigned to APPA and Arg moieties of rhizocticins but also other signals preventing full characterization of the compound(s). Several batches of the crude sample post-Amberlite step were purified on P2 column and analyzed by LC-MS as described above. The rhizocticin B consistently eluted with the same volume of eluent.

Partially purified samples from the P2 column were subjected to further purification by ion-exchange chromatography on CM Sephadex C-25 as previously described (Rapp et al., 1988). Fractions were analyzed by LC-MS as described above and pooled based on the presence of rhizocticin B $^{31}P$ NMR signals. The solvent and ammonium acetate of the elution buffer were removed by several rounds of lyophilization from water and samples were analyzed by $^{31}P$ and $^1H$ NMR spectroscopy (Fredenhagen et al., 1995; Rapp et al., 1988). NMR analysis confirmed that rhizocticin B was successfully purified to estimated 80-90% purity. Approximately 100 mg of rhizocticin B were obtained from a 3 L culture. LC-MS analysis on an Agilent LC/MSD Trap XCT Plus instrument (ESI+/ion trap): the $[M+H]^+$ ion detected at m/z 451.5 produced MSn fragments at m/z 433.2 ($[M-H_2O+H]^+$), 416.1 ($[M-H_2O-NH_3+H]^+$), 274.1 ($[b2+H_2O]^+$), 256.1 ($[b2]^+$), 239.1 ($[b2-NH_3]^+$). This sample was used as an authentic standard of rhizocticin B for LC-MS and NMR characterization of phosphonates.

Rhizocticin B Production in *B. subtilis* MMG272, and Analysis by $^{31}$P NMR Spectroscopy and LC-MS.

The heterologous producer *B. subtilis* MMG272 was grown for metabolite production as described for *B. subtilis* ATCC6633 with several exceptions. Spectinomycin was added to all of the media at 100 μg/mL. Additionally, PL medium was supplemented with tryptophan at 50 μg/mL and the fermentation culture volume was 2 L. The cell-free supernatant was taken through the same purification steps through Biogel P2 fractionation as described for rhizocticin purification. The P2 fractions corresponding to the rhizocticin B elution volume were analyzed by $^{31}$P NMR spectroscopy and compared to an authentic standard. Several phosphonates with chemical shifts in the range 17-27 ppm were detected; fractions eluted from the column with 90-100 mL of water (B7-8) contained a major phosphonate with a chemical shift of 20.7 ppm. The NMR sample of B7-8 was supplemented with 8 mM rhizocticin B and re-analyzed by $^{31}$P NMR spectroscopy. Sample B7-8 was analyzed by LC-MS as described for rhizocticin B analysis and its retention time and fragmentation pattern were consistent with the presence of rhizocticin B (FIG. 12B).

Preparation of Recombinant RhiG-C-His.

The rhiG gene was amplified by PCR using primers ORF7-fwd-Nde and ORF7-rev-Hind-C-His and fosmid 2-11E as a template. After digestion with appropriate restriction endonucleases, the PCR fragment (1017 bp) was cloned into the NdeI, HindIII sites of a pET26b vector. The expression plasmid pRhiG-C-His was used to transform *E. coli* BL21 (DE3). *E. coli* BL21/pRhiG-C-His was grown in LB media containing 50 μg/mL Kan to $OD_{600}$=0.6 followed by induction of protein over-expression with 0.2 mM IPTG at 18° C. overnight. Cells were pelletted by centrifugation and stored at −80° C.

The cell pellet (from 2 L culture) was thawed and re-suspended in 45 mL of lysis buffer (50 mM sodium phosphate, 300 mM NaCl, 10% glycerol, 10 mM imidazole, pH 8.0). Lysozyme was added to a concentration of 1 mg/mL, and the resulting suspension was incubated on ice for 30 min. The cells were disrupted by 2 passes through a French press (20,000 psi) and cell debris was removed by centrifugation (35,000 g, 4° C., 35 min). The resulting supernatant was slowly agitated with 6 mL (bed volume of resin) of Ni-NTA resin (QIAgen, Valencia, Calif.) pre-washed with lysis buffer at 4° C. for 3 h. The suspension was loaded into the column and the flow-through fraction was collected. The resin was washed with lysis buffer containing 20 mM imidazole until the concentration of proteins in eluent decreased substantially as judged by visual test with Bradford reagent. The bound protein was eluted with a buffer containing 250 mM imidazole. The desired fractions, as detected by SDS-PAGE, were pooled and concentrated using an Amicon Ultra YM-30 centrifugal filter unit (Millipore, Billerica, Mass.). The protein sample was loaded onto a PD-10 desalting column (GE Healthcare, Piscataway, N.J.) and eluted with 50 mM sodium phosphate, 200 mM NaCl, pH 7.5 as per the column manufacturer's instructions.

The purified RhiG-C-His protein (38.7 kDa) was concentrated to approximately 2 mL (precipitated particles removed by centrifugation), aliquotted, flash frozen with liquid nitrogen, and stored at −80° C. Typical yields of purified RhiG-C-His were approximately 20 mg/L of culture. The UV-vis spectrum of purified RhiG-C-His was transparent above 300 nm.

The native molecular weight of RhiG-C-His was determined using an ÄKTApurifier FPLC system equipped with a Superdex 200 10/300 GL column (GE Healthcare, Piscataway, N.J.). Standards and samples were isocratically eluted using 50 mM HEPES, 0.2 M KCl, 10% glycerol, pH 7.5 at 0.5 mL/min. The following protein standards (250 μL each, Sigma MW-GF-200) were used to built a molecular weight calibration curve: cytochrome c (12.4 kDa, 4 mg/mL), carbonic anhydrase (29 kDa, 6 mg/mL), bovine serum albumin (BSA, 66 kDa, 10 mg/mL), alcohol dehydrogenase (150 kDa, 10 mg/mL), and β-amylase (200 kDa, 8 mg/mL). Blue dextran (2000 kDa, 250 μL of 2 mg/mL) was used to determine the void volume of the column. RhiG-C-His was injected at a concentration of 5 mg/mL (250 μL). The elution volume of RhiG-C-His corresponded to a native molecular weight of approximately 75 kDa, indicating that RhiG exists as a homodimer.

RhiG Activity Assays.

A stock of 100 mM oxaloacetic acid was freshly prepared in 100 mM sodium cacodylate buffer pH 7.5. It was added to the PnAA sample to a final OAA concentration of 12 mM. The reaction was initiated by the addition of RhiG-C-His (45 μM) and the assay mixture was incubated at 30° C. for 1 h. A precipitate that formed during incubation was removed by centrifugation, and soluble proteins were removed by filtration through a Microcon YM-30 unit. Addition of OAA and RhiG without prior removal of RhiH-N-His and Ppd-Bf-His, or even simultaneously with PnAA formation, reduced the amount of the PnAA degradation product formed. Therefore, the samples intended for extensive NMR characterization were prepared in this manner to reduce the processing time. The Microcon units were sequentially rinsed with 0.1 M sodium hydroxide, water, and finally reaction buffer prior to use to eliminate trace amounts of glycerol because it produced $^1$H NMR signals in the region of interest. The enzymatic preparation of $^{13}$C-labeled compounds and the spectroscopic characterization of compounds Ia, Ib, Ia', Ia" and Ib' are described above.

Oxaloacetate Decarboxylation by RhiG-C-His.

The 650 μL assay mixture consisted of 10 mM oxaloacetate, 7.7 mM $MgCl_2$ and 23% $D_2O$ in 75 mM sodium cacodylate buffer (pH 7.5). The reaction was initiated by the addition of RhiG-C-His (42 μM). Equal amount of buffer (50 mM sodium phosphate, 200 mM NaCl, pH 7.5) was used in place of the enzyme in the control reaction. The reaction progress was monitored using 400 MHz $^1$H NMR spectroscopy as a conversion of OAA (H-3 signal at 3.45 ppm) to pyruvate (H-3 signal at 2.14 ppm). All of the OAA was converted to pyruvate in the presence of RhiG-C-His after 15 min incubation at room temperature. In the absence of enzyme, only 13% of OAA was converted to pyruvate under the same conditions as estimated by integration of proton signals for these compounds.

Preparation of Recombinant Proteins RhiH-N-His and Ppd-Bf-His.

The rhiH gene was amplified by PCR using primers rhiH-fwd-Nde and rhiH-rev-Hind-stop and fosmid 2-11E as a template. After digestion with appropriate restriction endonucleases, a PCR fragment (898 bp) was cloned into the NdeI, HindIII sites of a pET28a vector. The expression plasmid pRhiH-N-His was used to transform *E. coli* BL21 (DE3). *E. coli* BL21/pRhiH-N-His was grown in LB-Kan media. RhiH-N-His (34.7 kDa) was expressed and purified in the same manner as described above for expression and purification of RhiG-C-His.

Ppd-Bf-His protein, a phosphonopyruvate decarboxylase from *Bacteroides fragilis* with a C-terminal hexahistidine tag, was expressed and purified in the same manner as described above using plasmid pPpd-Bf-His.

Preparation of PnAA Substrate for RhiG Activity Assay.

The PnAA substrate was prepared either in situ or immediately prior to use in the downstream assays following a modified published procedure (Blodgett et al., Nat. Chem. Biol. 3, 480-485, 2007). The typical assay contained 100 mM sodium cacodylate, pH 7.5, 10 mM $MgCl_2$, 10 mM phosphoenolpyruvic acid monopotassium salt (PEP), and 1 mM thiamine pyrophosphate chloride (TPP). The reaction was initiated by the addition of RhiH-N-His and Ppd-Bf-His enzyme stocks at 2% (v/v) of the assay total volume. After incubation at 30° C. for 45 min, the proteins were removed using Microcon YM-30 centrifugal filter units and the filtrate was used without further purification as an approximately 10 mM stock of PnAA. Buffers containing 100 mM sodium phosphate, pH 7.5 or 50 mM HEPES, pH 7.5 were used in place of cacodylate buffer when needed. The total volume of the assay reaction was usually 500 μL and the entire sample (plus $D_2O$ added) was used for NMR analysis without further concentration or dilution.

To assess the extent of PnAA formation, $D_2O$ (20%) was added to enzyme-free assay and the sample was subjected to analysis by $^{31}P$ NMR spectroscopy. The conversion of PEP (−0.2 ppm) to PnAA (9.9 ppm) was observed when the reaction was run in HEPES or cacodylate buffers. In addition to signals from phosphate of enzyme stocks (2.6 ppm) and TPP cofactor (a doublet at −5.4 ppm and a doublet at −9.5 ppm), a broad signal at 15.4 ppm was also observed. The intensity of this signal increased upon prolonged incubation or storage of enzyme-free sample. This peak presumably corresponds to a product of PnAA degradation.

Preparation of the $^{13}C$-Labeled Compounds using the RhiG-C-His Assay.

Compound Ia' (Ia labeled with $^{13}C$ at C-5) was prepared by running the RhiG-C-His reaction as described in Methods with the exception that 3-$^{13}C$-phosphoenolpyruvic acid potassium salt was used in place of PEP for 2-$^{13}C$-PnAA preparation. Compound Ib' (Ib labeled with $^{13}C$ at C-5) was also detected in the assay mixture and characterized by NMR spectroscopy.

Compound Ia" (Ia labeled with $^{13}C$ at positions C-1, C-2, and C-3) was prepared using unlabeled PEP and uniformly labeled L-Asp as described below. The assay mixture (500 μL) contained 100 mM sodium cacodylate, pH 7.5, 10 mM $MgCl_2$, 10 mM PEP, 1 mM TPP, 10 mM U-$^{13}C$-L-Asp, and 10 mM 2-ketoglutaric acid sodium salt. The reaction was initiated by the addition of RhiH-N-His, Ppd-Bf-His, and AspAT (1 U/μL, Sigma G7005) enzyme stocks at 2% (v/v) and 26 μM RhiG-C-His and incubated at 30° C. for 45 min. Insoluble materials were removed by centrifugation and soluble proteins were removed by filtration through a pre-rinsed Microcon YM-30 unit. Samples were analyzed by $^{31}P$ and $^{13}C$ NMR spectroscopy and LC-MS/MS.

SEQUENCE SUMMARY

SEQ ID NO: 1 NUCLEOTIDE SEQUENCE OF rhi OPERON
SEQ ID NO: 2 AMINO ACID SEQUENCE OF RhiA
SEQ ID NO: 3 AMINO ACID SEQUENCE OF RhiB
SEQ ID NO: 4 AMINO ACID SEQUENCE OF RhiD
SEQ ID NO: 5 AMINO ACID SEQUENCE OF RhiE
SEQ ID NO: 6 AMINO ACID SEQUENCE OF RhiF
SEQ ID NO: 7 AMINO ACID SEQUENCE OF RhiG
SEQ ID NO: 8 AMINO ACID SEQUENCE OF RhiH
SEQ ID NO: 9 AMINO ACID SEQUENCE OF RhiI
SEQ ID NO: 10 AMINO ACID SEQUENCE OF RhiN
SEQ ID NO: 11 AMINO ACID SEQUENCE OF RhiJ
SEQ ID NO: 12 AMINO ACID SEQUENCE OF RhiK
SEQ ID NO: 13 AMINO ACID SEQUENCE OF RhiL
SEQ ID NO: 14 NUCLEOTIDE SEQUENCE OF plu OPERON
SEQ ID NO: 15 AMINO ACID SEQUENCE OF PluE
SEQ ID NO: 16 AMINO ACID SEQUENCE OF PluF
SEQ ID NO: 17 AMINO ACID SEQUENCE OF PluG
SEQ ID NO: 18 AMINO ACID SEQUENCE OF PluH
SEQ ID NO: 19 AMINO ACID SEQUENCE OF PluI
SEQ ID NO: 20 AMINO ACID SEQUENCE OF PluN
SEQ ID NO: 21 AMINO ACID SEQUENCE OF PluJ
SEQ ID NO: 22 AMINO ACID SEQUENCE OF PluK
SEQ ID NO: 23 AMINO ACID SEQUENCE OF PluL
SEQ ID NO: 24 AMINO ACID SEQUENCE OF Plu-AT-Pgrasp38
SEQ ID NO: 25 AMINO ACID SEQUENCE OF Plu-AT-Pgrasp37

The invention claimed is:

1. An isolated nucleic acid comprising a first nucleotide sequence encoding a first polypeptide having a first sequence identity of at least 70 percent to an amino acid sequence selected from the group consisting of SEQ ID NOS: 2-3 and 5-13, or having a first sequence identity of at least 71 percent to an amino acid sequence of SEQ ID NO: 4.

2. The isolated nucleic acid of claim 1, wherein the first sequence identity is at least 71% to an amino acid sequence of SEQ ID NOS: 2-13.

3. The isolated nucleic acid of claim 1, wherein the first sequence identity is at least 70 percent to SEQ ID NO: 7.

4. The isolated nucleic acid of claim 3, further comprising a second nucleotide sequence encoding a second polypeptide having a second sequence identity of 70 percent or greater to SEQ ID NO: 8.

5. The isolated nucleic acid of claim 4, further comprising a third nucleotide sequence encoding a third polypeptide having a third sequence identity of at least 70 percent to a third amino acid selected from the group consisting of SEQ ID NOS: 2-6 and 9-13.

6. A vector comprising an isolated nucleic acid comprising a first nucleotide sequence encoding a first polypeptide having a first sequence identity of 70 percent or greater to an amino acid sequence selected from the group consisting of SEQ ID NOS: 2-3 and 5-13, or having a first sequence identity of 71 percent or greater to an amino acid sequence of SEQ ID NO. 4.

7. The vector of claim 6, wherein the vector is capable of integration into it host cell genome.

8. The vector of claim 6, wherein the vector is selected from the group consisting of a bacterial vector, a mammalian vector, an insect vector, and a yeast vector.

9. A transformed cell comprising: a vector comprising an isolated nucleic acid comprising a nucleotide sequence encoding a polypeptide having a sequence identity of 70 percent or greater to an amino acid sequence selected from the group consisting of SEQ ID NOS: 2-3 and 5-13, or a sequence identity of 71 percent or greater to an amino acid sequence of SEQ ID NO. 4;
wherein the transformed cell is capable of producing an APPA-containing peptide.

10. The transformed cell of claim 9, wherein the APPA-containing peptide is a rhizocticin.

11. The transformed cell of claim 10, wherein the rhizocticin is rhizocticin B.

12. The transformed cell of claim 9, wherein the transformed cell is selected from a group consisting of a Gram negative organism, a Gram positive organism, a mammalian cell, an insect cell, and a yeast cell.

13. The transformed cell of claim 9, wherein the transformed cell is a member of the genus *Bacillus*.

14. The transformed cell of claim 9, wherein the transformed cell is a member of the genus *Streptomyces*.

15. A method for producing an APPA-containing peptide, the method comprises the steps of:
transforming a host cell with an isolated nucleic acid comprising a nucleotide sequence encoding a polypeptide having a sequence identity of 70 percent or greater to an amino acid sequence selected from the group consisting of SEQ ID NOS: 2-3 and 5-13, or a sequence identity of 71 percent or greater to an amino acid sequence of SEQ ID NO. 4; and
growing the transformed host cell under conditions to produce an APPA-containing peptide.

16. The method of claim 15, wherein the untransformed host cell is not capable producing the APPA-containing peptide.

17. The method of claim 15, wherein the APPA-containing peptide is a rhizocticin.

18. The method of claim 15, further comprising the step of isolating the APPA-containing peptide from the transformed host cell or from the supernatant of the transformed cell.

19. The method of claim 18, further comprising the step of replacing at least one amino acid of the isolated APPA-containing peptide.

* * * * *

UNITED STATES PATENT AND TRADEMARK OFFICE
CERTIFICATE OF CORRECTION

PATENT NO. : 8,372,601 B2
APPLICATION NO. : 13/011075
DATED : February 12, 2013
INVENTOR(S) : William W. Metcalf et al.

Page 1 of 1

It is certified that error appears in the above-identified patent and that said Letters Patent is hereby corrected as shown below:

Title page, item [75] should read as follows:

Inventor: Junkai Zhang, Urbana, IL (US)

Signed and Sealed this
Nineteenth Day of March, 2013

Teresa Stanek Rea
*Acting Director of the United States Patent and Trademark Office*